United States Patent [19]

Powell et al.

[11] Patent Number: 5,550,149
[45] Date of Patent: Aug. 27, 1996

[54] MDR REVERSAL AGENTS

[75] Inventors: Dennis Powell, Peekskill, N.Y.; Rolf Paul, River Vale, N.J.; William A. Hallett, New City, N.Y.; Dan M. Berger, Orangeburg, N.Y.; Minu D. Dutia, West Nyack, N.Y.

[73] Assignee: American Cyanamid Company, Madison, N.J.

[21] Appl. No.: 328,643

[22] Filed: Oct. 25, 1994

Related U.S. Application Data

[62] Division of Ser. No. 92,653, Jul. 16, 1993, Pat. No. 5,387,685.

[51] Int. Cl.⁶ .................... C07D 209/44; A61K 31/40
[52] U.S. Cl. ............................ 514/416; 548/470
[58] Field of Search ................ 548/470; 514/416

[56] References Cited

U.S. PATENT DOCUMENTS 2,969,362  1/1961  Twelt et al. .................. 544/315
4,792,559  12/1988  Regnier et al. ................ 514/311

OTHER PUBLICATIONS

Mukaiyama, T. et al., Chem. Lett., 11:1177–80 (1976).
Windholz, M., Editor, The Merck Index, Ninth Edition #3300, 3302, 4146, 5985, 7115, 7711, 8933, 9047 (1976).

Primary Examiner—C. Warren Ivy
Assistant Examiner—D. Margaret M. Mach
Attorney, Agent, or Firm—Arnold S. Milowsky

[57] ABSTRACT

Compounds of the general formula:

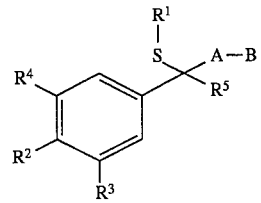

wherein $R_1$, $R_2$, $R_3$, $R_4$ and $R_5$ are herein described, A is a straight or branched ($C_2$–$C_{12}$)alkyl or a phenyl moiety and B is a moiety of the formula:

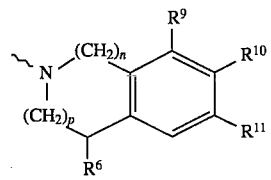

The compounds are effective in potentiating the activity of chemotherapeutic anti-cancer agents by increasing the sensitivity of multi-drug resistant cells to such chemotherapeutic agents.

13 Claims, No Drawings

MDR REVERSAL AGENTS

This is a divisional of application Ser. No. 08/092,653 filed on Jul. 16, 1993 now U.S. Pat. No. 5,387,685.

FIELD OF THE INVENTION

The present invention describes various bicyclic amines that are effective in resensitizing multiple drug resistant cells to chemotherapeutic agents such as doxorubicin, vincristine and bisantrene. This resensitization has the effect of reducing the amount of chemotherapeutic agent necessary to kill those cells. In addition this potentiation of activity of the chemotherapeutic agent with the compounds of this invention makes it possible to treat multi-drug resistant tumors in animals.

An object of this invention is to provide a method for increasing the sensitivity of multi-drug resistant cells by the use of compounds of this invention.

An additional object of this invention is to provide a method for treating tumors that are either intrinsically or extrinsically multi-drug resistant in warm blooded animals by the administration of a therapeutically effective dose of a compound of this invention prior to, concurrent or after the administration of a therapeutically effective dose of an antitumor chemotherapeutic agent.

BACKGROUND OF THE INVENTION

Resistance of tumor cells to chemotherapeutic drugs is an important problem in the clinical management of cancer. One type of resistance is characterized by the cross resistance to a wide variety of chemotherapeutic agents with no major structural similarities or similar modes of action. This phenomenon is termed multiple drug resistance. The evidence suggests that this form of resistance is due to the presence in tumor cells of a 170 kD transmembrane protein that is termed P-glycoprotein. It is thought that resistance is conferred by the ability of P-glycoprotein to actively transport chemotherapeutic agents out of the cells and thereby lower the intracellular concentrations of such drugs to non-toxic levels. Clinically this translates into a reduction of the therapeutic index of such drugs to an ineffective level. It has been shown that MDR1 mRNA levels are elevated in untreated, intrinsically drug resistant tumors including those derived from the colon, kidney, adrenal gland, liver and pancreas as well as some cancers at relapse after chemotherapy including breast cancer, neuroblastoma, ALL and nodular poorly differentiated lymphoma.

Chemotherapeutic agents in clinical use to which multi-drug resistance has been observed include doxorubicin, vinblastine, vincristine, taxol, duanomycin, etopiside, teniposide and actinomycin D.

In the early 1980's it was discovered that multiple drug resistance tumor cells could be resensitized to chemotherapeutic agents with the antihypertensive, verapamil. Since this time verapamil, and several other agents including R-verapamil and trifluoroperizine have been used as resensitizing agents for the treatment of cancer in the clinic. Their activity has been limited by toxic side effects.

The present invention describes various bicyclic amines that are effective in resensitizing multiple drug resistant cells to chemotherapeutic agents such as doxorubicin, vincristine and bisantrene. This resensitization has the effect of reducing the amount of chemotherapeutic agent necessary to kill those cells. In addition this potentiation of activity of the chemotherapeutic agent with the compounds of this invention makes it possible to treat mu! ti-drug resistant tumors in warm blooded animals.

An object of this invention is provide a method for increasing the sensitivity of multi-drug resistant cells by the use of-compounds in this invention.

An additional object of this invention is to provide a method for treating tumors that are either intrinsically or extrinsically multi-drug resistant in warm blooded animals by the administration of a therapeutically effective dose of a compound of this invention prior to, concurrent or after the administration of a therapeutically effective dose of an antitumor chemotherapeutic agent.

SUMMARY OF THE INVENTION

This invention is concerned with new compounds of the formula:

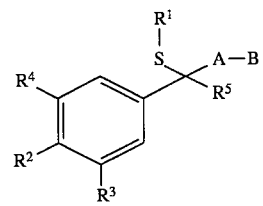

wherein $R^2$ is H, OH, O-alkyl($C_1$–$C_4$), F, Br, Cl, I, $NO_2$, $OCF_3$, alkyl ($C_1$–$C_6$), or N $(R^{12})_2$;

$R^3$ is H, OH, O-alkyl($C_1$–$C_3$), straight or branched OSi—($C_1$–$C_4$) alkyl, F, Br, $C_1$, I, $NO_2$, alkyl($C_1$–$C_6$), $OCH_2CH_2Cl$, O-alkyl ($C_2$–$C_5$) -heterocycle, O-alkyl($C_2$–$C_5$)N($R^{12}$)$_2$, $OSO_2CF_3$, $OCF_3$, or N($R^{12}$)$_2$;

or R and R taken together are methylenedioxy or ethylenedioxy;

$R^4$ is H, OH, O-alkyl($C_1$–$C_4$), F, Br, Cl, I, or alkyl($C_1$–$C_3$);

$R^5$ is H, CN, $CH_2$ OH, $CO_2$ ($C_1$–$C_3$) alkyl, $CH_2NH_2$, $CH_2N(R^{12})_2$ or alkyl ($C_1$–$C_3$);

$R^1$ is straight or branched ($C_1$–$C_{12}$)alkyl, cycloalkyl ($C_3$–$C_7$), bicycloalkyl ($C_6$–$C_{10}$), tricycloalkyl($C_6$–$C_{10}$), a heterocycle or

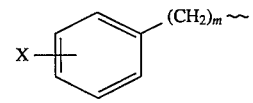

m is an integer 0–3;

X is H, straight or branched ($C_1$–$C_4$)alkyl, I, Cl, Br, F, $NO_2$, or N($R^{12}$)$_2$;

A is straight or branched ($C_2$–$C_{12}$)alkyl,

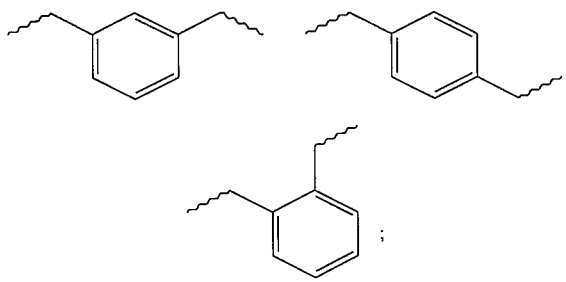

B is

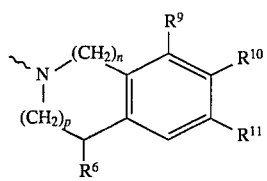

n and p are integers with n=0–2, p=0–2;
$R^6$ is H, alkyl($C_1$–$C_4$), or

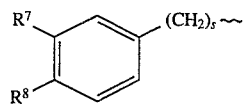

s is an integer with s=1–3,
$R^7$ and $R^8$ are independently H, alkyl($C_1$–$C_4$), or O-alkyl($C_1$–$C_4$);
$R^9$ is H, O-alkyl($C_1$–$C_4$), F, Br, Cl, I, or alkyl($C_1$–$C_3$);
$R^{10}$ is H, O-alkyl($C_1$–$C_3$), OH, F, Br, Cl, I, alkyl($C_1$–$C_3$), $OCH_2CH_2Cl$, O-alkyl ($C_2$–$C_5$)-heterocycle, S-alkyl($C_1$–$C_4$), $OSO_2CF_3$, $OCF_3$, $OCH_2$-phenyl, $NO_2$ or $N(R^{12})_2$;
$R^{11}$ is H O-alkyl($C_1$–$C_4$), S-alkyl($C_1$–$C_4$), OH, F, Br, Cl, I, $OCF_3$, $OCH_2$-phenyl, alkyl ($C_1$–$C_3$) or O-alkyl ($C_2$–$C_5$)-heterocycle;
$R^{12}$ is alkyl($C_1$–$C_4$); and
the pharmaceutically acceptable salts thereof.
A preferred class of compounds of the formula:

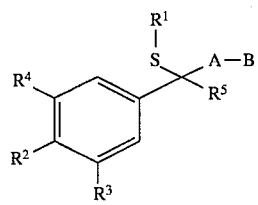

wherein
$R^2$ is H, O-alkyl($C_1$–$C_4$), F, Br, Cl, I, $OCF_3$, or alkyl ($C_1$–$C_6$);
$R^3$ is H, O-alkyl($C_1$–$C_3$), straight or branched OSi—($C_1$–$C_4$)alkyl, F, Br, Cl, I, $NO_2$, alkyl($C_1$–$C_6$), $OCH_2CH_2Cl$, O-alkyl ($C_2$–$C_5$)-heterocycle, $OSO_2CF_3$, or $OCF_3$; or
$R^2$ and $R^3$ together are methylenedioxy or ethylenedioxy;
$R^4$ is H, O-alkyl($C_1$–$C_4$), F, Br, Cl, I, or alkyl($C_1$–$C_6$);
$R^5$ is H, CN, $CH_2OH$, $CO_2(C_1$–$C_3)$alkyl, or alkyl($C_1$–$C_3$);
$R^1$ is straight or branched ($C_1$–$C_{12}$) alkyl, cycloalkyl ($C_3$–$C_7$), bicycloalkyl ($C_6$–$C_{10}$), tricycloalkyl ($C_6$–$C_{10}$), a heterocycle or

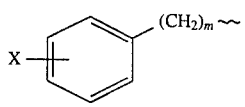

m is an integer 0–3;
X is H, straight or branched($C_1$–$C_4$)alkyl, I, Cl, Br, F, $NO_2$, or $N(R^{12})_2$;

A is straight or branched($C_2$–$C_{12}$)alkyl,

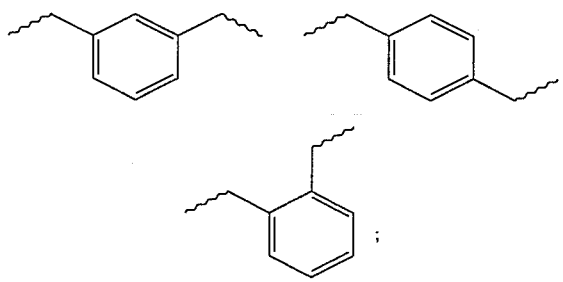

B is

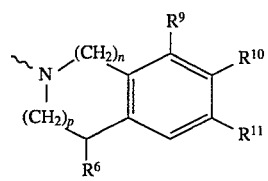

n and p are integers with n=1–2, p=0–1;
$R^6$ is H, alkyl($C_1$–$C_4$), or

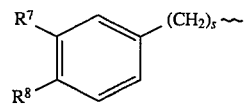

s is an integer with s=1–3;
$R^7$ and $R^8$ are independently H, alkyl ($C_1$–$C_4$), or O-alkyl($C_1$–$C_4$);
$R^9$ is H, O-alkyl($C_1$–$C_4$), F, Br, Cl, I, or alkyl($C_1$–$C_3$);
$R^{10}$ is H, O-alkyl($C_1$–$C_3$), OH, F, Br, Cl, I, alkyl($C_1$–$C_3$), $OCH_2CH_2Cl$, O-alkyl($C_2$–$C_5$)-heterocycle, $OCH_2$-phenyl or $OSO_2CF_3$;
$R^{11}$ is H, O-alkyl($C_1$–$C_4$), OH, O-alkyl($C_2$–$C_5$)-heterocycle, F, Br, Cl, I or alkyl($C_1$–$C_3$);
$R^{12}$ is alkyl($C_1$–$C_4$); and the pharmaceutically acceptable salts thereof.
An especially preferred class of compounds of the formula:

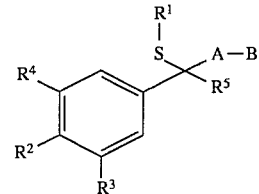

wherein
$R^2$ is H, O-alkyl($C_1$–$C_4$) or alkyl($C_1$–$C_6$);
$R^3$ is H, O-alkyl($C_1$–$C_3$), OSi(t-$C_4H_9$)($CH_3$)$_2$, alkyl($C_1$–$C_6$), $OCH_2CH_2Cl$, $OCH_2CH_2$-N-imidazole or $OSO_2CF_3$; or
$R^2$ and $R^3$ taken together are methylenedioxy or ethylenedioxy;
$R^4$ is H, O-alkyl($C_1$–$C_4$), or alkyl($C_1$–$C_6$);
$R^5$ is H, CN, $CH_2$OH, $CO_2(C_1$–$C_3)$ alkyl, or alkyl($C_1$–$C_3$);
$R^1$ is straight or branched ($C_1$–$C_{12}$)alkyl, cycloalkyl($C_3$–$C_7$), bicycloalkyl($C_6$–$C_{10}$), tricycloalkyl($C_6$–$C_{10}$), a heterocycle or

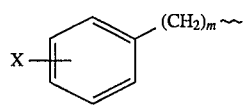

m is an integer 0–3;
X is H, straight or branched $(C_1-C_4)$alkyl;
A is straight or branched $(C_2-C_{12})$alkyl,

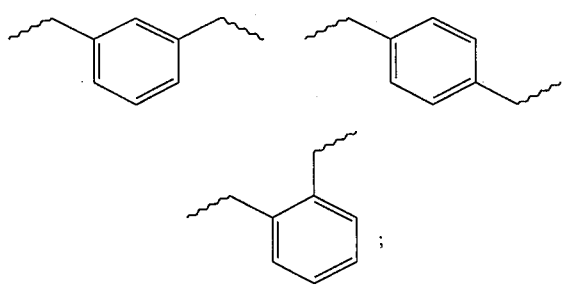

B is

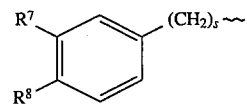

n and p are integers with n=1–2, p=0–1;
$R^6$ is H or alkyl$(C_1-C_4)$;

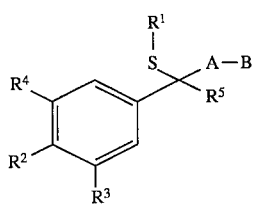

s is an integer with s=1–3;
$R^7$ and $R^8$ are independently H or O-alkyl$(C_1-C_4)$;
$R^9$ is H or O-alkyl$(C_1-C_4)$;
$R^{10}$ is H, O-alkyl$(C_1-C_3)$, OH, F, Br, Cl, I, alkyl$(C_1-C_3)$, $OCH_2CH_2Cl$, $OCH_2CH_2$-N-imidazole, $OCH_2$-phenyl or $OSO_2CF_3$;
$R^{11}$ is H, O-alkyl$(C_1-C_4)$, OH, F, Br, Cl, I or alkyl$(C_1-C_3)$;
$R^{12}$ is alkyl$(C_1-C_4)$; and the pharmaceutically acceptable salts thereof.

A most preferred class of compounds of the formula:

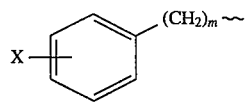

wherein
$R^2$ is H or $0-CH_3$;
$R^3$ is H, $O-CH_3$, $OSi(t-C_4H_9)(CH_3)_2$, $OCH_2CH_2Cl$, $OCH_2CH_2$—N-imidazole or $OSO_2CF_3$;
or $R^2$ and $R^3$ taken together are methylenedioxy or ethylenedioxy;
$R^4$ is H or $O-CH_3$;
$R^5$ is H, CN, $CH_2OH$, $CO_2CH_3$, or alkyl$(C_1-C_3)$;
$R^1$ is straight or branched $(C_4-C_5)$alkyl, cycloalkyl$(C_5-C_6)$, adamantyl 2-pyridyl or

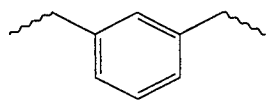

m is an integer 0–1;
X is H, straight or branched $(C_1-C_4)$ alkyl;
A is straight or branched $(C_2-C_{12})$alkyl,

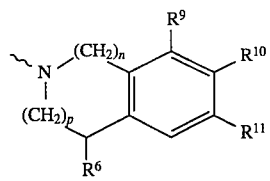

B is

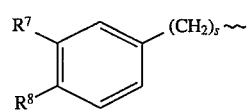

n and p are integers with n=1–2, p=0–1;
$R^6$ is H or $CH_3$;

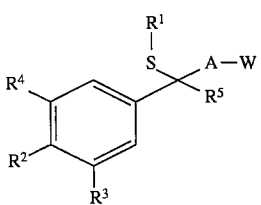

s=1;
$R^7$ and $R^8$ are independently H or O—$CH_3$;
$R^9$ is H or O-alkyl$(C_1-C_4)$;
$R^{10}$ is H, O—$CH_3$, OH, Cl, $OCH_2CH_2Cl$, $OCH_2CH_2$—N-imidazole, $OCH_2$-phenyl or $OSO_2CF_3$;
$R^{11}$ is H, O—$CH_3$, OH, Cl;
$R^{12}$ is alkyl$(C_1-C_4)$; and the pharmaceutically acceptable salts thereof.

A heterocycle is a 5–6membered ring containing from 1 to 4 heteroatoms selected from the group consisting of nitrogen, sulfur and oxygen atoms. Representative heterocycles are imidazole, pyrrole, 1,2,4-triazole, oxazole, isoxazole, furan, thiophene, pyridine, pyrimidine and thiazole.

Also included in the present invention are compounds useful as intermediates for producing the compounds of the present invention. Such intermediate compounds include those of formula:

wherein
$R^2$ is H, OH, O-alkyl$(C_1-C_4)$, F, Br, Cl, I, $NO_2$, $OCF_3$, alkyl$(C_1-C_6)$, or $N(R^{12})_2$;
$R^3$ is H, OH, O-alkyl$(C_1-C_3)$, straight or branched OSi—$(C_1-C_4)$alkyl, F, Br, Cl, I, $NO_2$, alkyl$(C_1-C_6)$, $OCH_2CH_2Cl$, O-alkyl$(C_2-C_5)$-heterocycle, O-alkyl$(C_2-C_5)N(R^{12})_2$, $OCF_3$, or $N(R^{12})_2$;

or R and R taken together are methylenedioxy or ethylenedioxy;

$R^4$ is H, OH, O-alkyl($C_1$-$C_4$), F, Br, Cl, I, or alkyl($C_1$-$C_3$);

$R^5$ is H, CN, $CH_2OH$, $CO_2$($C_{12}$-$C_3$)alkyl or alkyl($C_1$-$C_3$);

$R^1$ is straight or branched ($C_1$-$C_{12}$) alkyl, cycloalkyl($C_3$-$C_7$), bicycloalkyl($C_6$-$C_{10}$), tricycloalkyl($C_6$-$C_{10}$), $$X-\underset{}{\underline{\phantom{XX}}}-(CH_2)_m\sim$$

m is an integer 0–3,

X is H, straight or branched ($C_1$-$C_4$) alkyl, I, Cl, Br, F, $NO_2$, or $N(R^{12})_2$;

or $R^1$ is a heterocycle with the proviso that the heterocycle cannot be $$(CH_2)_r\diagdown \underset{N}{\overset{N}{\diagup}}\diagdown$$

where r is an integer 1–4;

A is straight or branched ($C_2$-$C_{12}$)alkyl,

W is Br, Cl, I, $NH_2$, $OSO_2$alkyl($C_1$-$C_3$), $OSO_2CF_3$, $OSO_2$-phenyl, $OSO_2$-p-tolyl, with the proviso that when A is —$CH_2CH_2CH_2$—, W cannot be OH or Cl, Br, F or I;

$R^{12}$ is alkyl($C_1$-$C_4$); and the pharmaceutically acceptable salts thereof.

A heterocycle is a 5–6 membered ring containing from 1 to 4 heteroatoms selected from the group consisting of nitrogen, sulfur and oxygen atoms. Representative heterocycles are imidazole, pyrrole, 1,2,4-triazole, oxazole, isoxazole, furan, thiophene, pyridine, pyrimidine and thiazole.

This invention is concerned with the use of the compounds of this invention with anticancer chemotherapeutic agents in the treatment of multi-drug resistant tumors and the treatment of cancer.

It has been discovered that the compounds of the present invention have the ability to resensitize multi-drug resistant cells to antitumor chemotherapeutic agents such as vincristine, doxrubicin, and bisantrene. Further it has been discovered that compounds of the present invention have the ability to potentiate the ability of antitumor therapeutic agents such as doxorubicin to reduce the tumor size in animals bearing multi-drug resistant tumors. Due to these properties the compounds of the present invention are expected to have a major clinical use in the treatment of multi-drug resistant tumors.

DESCRIPTION OF THE PREFERRED EMBODIMENT

The compounds of this invention may be prepared according to one or more of the following reaction schemes:

Scheme A

In accordance with Scheme A, compounds of the formula:

wherein $R^2$ is H, OH, O-alkyl($C_1$-$C_4$), F, Br, Cl, I, $NO_2$, $OCF_3$, alkyl($C_1$-$C_6$), or $N(R^{12})_2$;

$R^3$ is H, OH, O-alkyl($C_1$-$C_3$), straight or branched OSi—($C_1$-$C_4$)alkyl, F, Br, Cl, I, $NO_2$, alkyl($C_1$-$C_6$), $OCF_3$, O-alkyl($C_2$-$C_5$)-heterocycle, or O-alkyl($C_2$-$C_5$)$N(R^{12})_2$, or $R^2$ and $R^3$ taken together are methylenedioxy or ethylenedioxy;

$R^4$ is H, OH, O-alkyl($C_1$-$C_4$), F, Br, Cl, I, or alkyl($C_1$-$C_3$);

$R^5$ is H, CN, $CO_2$($C_1$-$C_3$)alkyl, alkyl($C_1$-$C_3$), $CH_2NH_2$, or $CH_2N$ $(R^{12})_2$;

$R^1$ is straight or branched ($C_1$-$C_{12}$) alkyl, cycloalkyl($C_3$-$C_7$), bicycloalkyl($C_6$-$C_{10}$), tricycloalkyl($C_6$-$C_{10}$), a heterocycle or

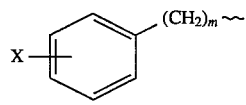

m is an integer 0–3,
X is H, straight or branched $(C_1-C_4)$alkyl, I, Cl, Br, F, $NO_2$, or $N(R^{12})_2$;
A is straight or branched $(C_2-C_{12})$alkyl,

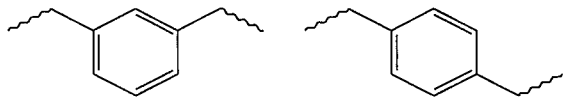

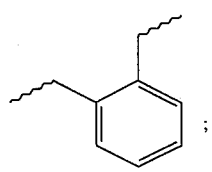

;

B is

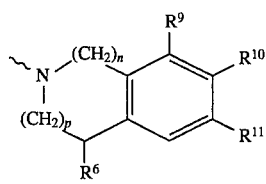

n and p are integers with n=0–2, p=0–2;
$R^6$ is H or alkyl$(C_1-C_4)$;

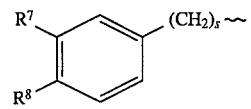

s is an integer with s=1–3;
$R^7$ and $R^8$ are independently H, alkyl$(C_1-C_4)$, or O-alkyl$(C_1-C_4)$;
$R^9$ is H, O-alkyl$(C_1-C_4)$, F, Br, Cl, I, or alkyl$(C_1-C_3)$;
$R^{10}$ is H, O-alkyl$(C_1-C_3)$, OH, S-alkyl$(C_1-C_4)$, F, Br, Cl, I, alkyl$(C_1-C_3)$, $OCH_2CH_2Cl$, O-alkyl$(C_2-C_5)$-heterocycle, $OSO_2CF_3$, $OCF_3$, $OCH_2$-phenyl, $NO_2$ or N $(R^{12})_2$;
$R^{11}$ is H, O-alkyl$(C_1-C_4)$, S-alkyl$(C_1-C_4)$, OH, F, Br, Cl, I, $OCF_3$, $OCH_2$-phenyl, alkyl$(C_1-C_3)$ or O-alkyl$(C_2-C_5)$-heterocycle;
$R^{12}$ is alkyl$(C_1-C_4)$;
may be prepared in the following manner:

the arylchloroacetonitrile, 3, may be prepared from the aryl aldehyde, 1, via 2 as described in U.S. Pat. No. 4,833,162. The intermediate 4 may be prepared from 3, by reaction of 3 with $R^1SH$, wherein $R^1$ is as defined hereinabove, and a base in polar solvents such as acetonitrile at elevated temperatures. Deprotonation of 4 with a strong base such as sodium hydride in an aprotic solvent such as dimethylsulfoxide and reacting with X-A-Y, wherein A is as defined hereinabove and X and Y are independently chlorine, bromine or iodine, affords intermediate 5. Reaction of 5 with HB, wherein B is as defined hereinabove, in a polar solvent such as N,N-dimethylformamide and a tertiary amine or alkali carbonate such as potassium carbonate at elevated temperatures affords 6. Alternatively intermediate 7 can be prepared by treatment of compound 7 with a strong base such as lithium hexamethyldisilazide in an ethereal solvent such as tetrahydrofuran and then with a disulfide, $R^1SSR^1$ wherein $R^1$ is as defined hereinabove. Intermediate 4, wherein $R^5$=H, can also be prepared by reaction of intermediate 8, wherein X is as defined hereinabove, with $R^1SH$, wherein $R^1$ is as defined hereinabove, by the method of Freudenberg, Carrara, and Cohn, Ann., 446, 94 (1925). Compound 6 can be simply elaborated further by known methods, eg. $R^3$=OH to $OCH_2CH_2Cl$ to $OCH_2CH_2$—N-imidazole.

Scheme B

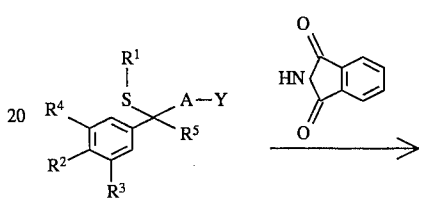

In accordance with Scheme B, wherein $R^1$–$R^{12}$, A, B, X, Y, and n are as defined for scheme A, treatment of compound 5 with potassium pthalimide in a polar solvent such as N,N-dimethylformamide affords compound 9. Treatment of compound 9 with hydrazine hydrate in an alcoholic solvent affords the amine, compound 10. Reaction of compound 10 with compound 11 in the presence of base affords compound 6.

Scheme C

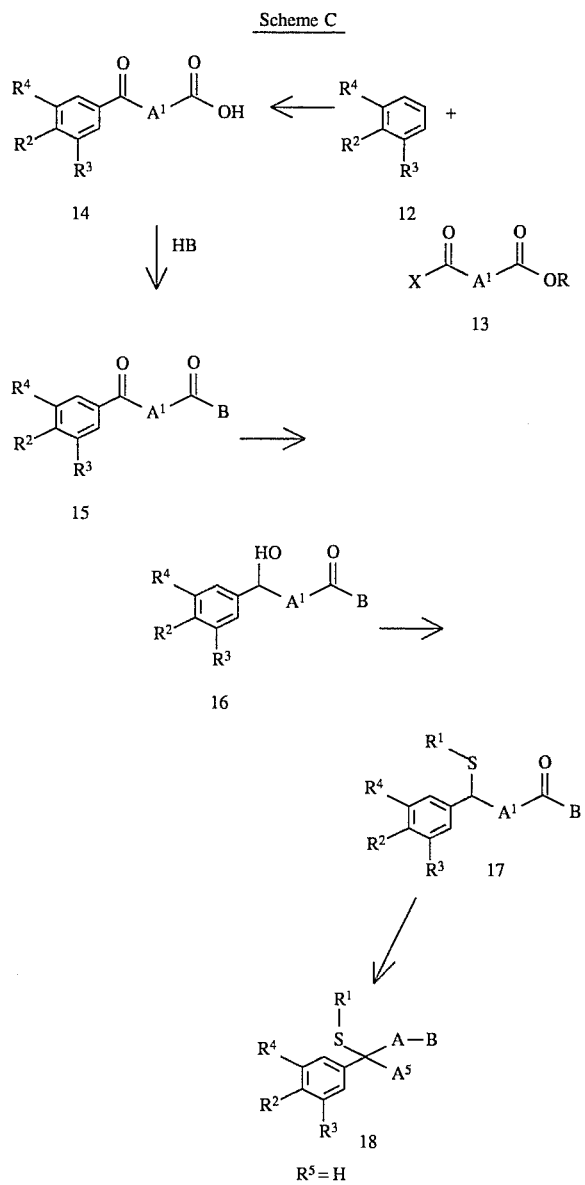

In accordance with Scheme C, compounds of the formula:

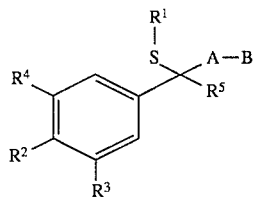

wherein
$R^2$ is H, O-alkyl($C_1$–$C_4$), F, Br, Cl, I, or alkyl($C_1$–$C_6$);
$R^3$ is H, O-alkyl($C_1$–$C_3$), F, Br, Cl, I, or alkyl($C_1$–$C_6$);
or $R^2$ and $R^3$ taken together are methylenedioxy or ethylenedioxy;
$R^4$ is H, O-alkyl($C_1$–$C_4$), F, Br, Cl, I, or alkyl($C_1$–$C_3$);
$R^5$ is H;
$R^1$ is straight or branched ($C_1$–$C_{12}$)alkyl, cycloalkyl($C_3$–$C_7$), bicycloalkyl($C_6$–$C_{10}$), a heterocycle or

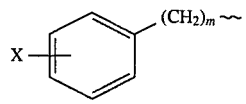

m is an integer 0–3,
X is H, straight or branched ($C_1$–$C_4$)alkyl, I, Cl, Br, F, $NO_2$, or $N(R^{12})_2$;
A is straight or branched ($C_2$–$C_{12}$)alkyl;

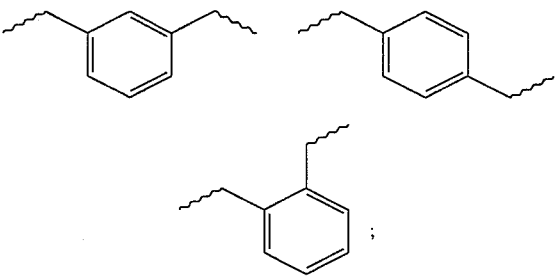

B is

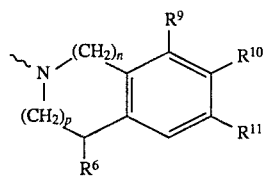

n and p are integers with n=0–2, p=0–2;
$R^6$ is H, alkyl($C_1$–$C_4$), or

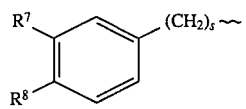

s is an integer with s=1–3,
$R^7$ and $R^8$ are independently H, alkyl($C_1$–$C_4$), or O-alkyl($C_1$–$C_4$);
$R^9$ is H, O-alkyl($C_1$–$C_4$), F, Br, Cl, I, or alkyl($C_1$–$C_3$);
$R^{10}$ is H, O-alkyl($C_1$–$C_3$), OH, S-alkyl($C_1$–$C_4$), F, Br, Cl, I, alkyl($C_1$–$C$ ), $OCF_3$, $OSO_2CF_3$, $OCH_2$-phenyl, $NO_2$ or N ($R^{12}$)$_2$;
$R^{11}$ is H, O-alkyl($C_1$–$C_4$), S-alkyl($C_1$–$C_4$), OH, F, Br, Cl, I, $OCF_3$, $OCH_2$-phenyl or alkyl($C_1$–$C_3$);
$R^{12}$ is alkyl($C_1$–$C_4$);
may be prepared in the following manner:

Friedal Crafts acylation of compound 12 with compound 13 with a Lewis acid such as aluminum chloride in a solvent such as methlene chloride affords compound 14 after saponification with a base such as sodium hydroxide in alcohol water mixtures. Acylation of compound 14 with BH, wherein B is as defined hereinabove, by activation of 14 with reagents such as diethylcyanophosphonate in solvents such as N,N-dimethylformamide in the presence of tertiary amine bases affords compound 15. Reduction of compound 15 with reagents such as sodium borohydride in alcoholic solvents affords compound 16. Treatment of 16 with a Lewis acid such as zinc iodide in the presence of $R^1$SH, wherein $R^1$ is as defined hereinabove, in a halogenated solvent such as 1,2-dichloroethane affords 17. Reduction of 17 with a reducing agent such as borane-methyl sulfide in a solvent such as tetrahydrofuran affords 18. Compounds 18 can be simply elaborated further by known methods, eg. $R^{10}$=OH to $OCH_2CH_2Cl$ to $OCH_2CH_2$—N-imidazole.

BIOLOGICAL ACTIVITY

In vitro Testing Cells

A subpopulation of human ovarian carcinoma cells (OVCAR-3, also known as HTB-161) is obtained by selecting cells for high expression of the B72.3 antigen. Such cells are sorted by a fluorescent activated cell sorter (FACS; Beeton Dickinson Model 440). A clone (S1) from this population is isolated and then subjected to step-wise increasing amounts of bisantrene over a period of 12–16 weeks. The most resistant cell line, designated S1-B1-20, denotes the S1 clone, the first independently-isolated bisantrene-selected cell line (B1), and the maintenance concentration in micromolar (20 μM). The bisantrene-selected cells used in this study are chronically maintained in 20 μM drug (the limit of solubility of bisantrene).

Screening Assay for Reversal Agents

Cells, prepared by trypsinization, are plated at 20,000 cells/well in media with and without bisantrene. Then, test agents at varying concentrations are added to the cells. The test agents are solubilized in 100% dimethylsulfoxide; the final dimethylsulfoxide concentration in the seeded plates does not exceed 0.1%. Completed plates are incubated for 3 days at 37° C. in a moisturized 7% $CO_2$ atmosphere. Cell survival is estimated by the sulforodoamine B assay (Skehan et al., 1990). Dye content/well is read at 540 nm in a microtiter reader. Values are electronically processed, % cell survival compared to untreated cells is computed, and the results are expressed as the difference between these values. Experiments are run in the presence of the test agent alone and the test agent in combination with 20 μM bisantrene. The Difference Score between those two experiments is reported below for 3 different concentrations of test agent.

TABLE 1

| Example # | Difference Score at 1 microM | Difference Score at 10 microM | Difference Score at 20 microM |
|---|---|---|---|
| Verapamil | 4 | 39 | 54 |
| 4 | 72 | 85 | 59 |
| 6 | — | 55 | — |
| 9 | 8 | 85 | 71 |
| 11 | 72 | 87 | 89 |
| 12 | 45 | 84 | 72 |
| 14 | 47 | 47 | 14 |
| 16 | 28 | 73 | 14 |
| 17 | 77 | 65 | 29 |
| 20 | 81 | 51 | 15 |
| 21 | 23 | 72 | 56 |
| 22 | 33 | 55 | 32 |
| 26 | 54 | 85 | 48 |
| 28 | 95 | 68 | 17 |
| 29 | 0 | 40 | 47 |
| 30 | 6 | 90 | 62 |
| 31 | 0 | 31 | 5 |
| 32 | 79 | 68 | 35 |
| 33 | 62 | 71 | 21 |
| 34 | 22 | 77 | 34 |
| 35 | 63 | 90 | 67 |
| 37 | 86 | 67 | 25 |
| 39 | 49 | 82 | 69 |
| 41 | 82 | 71 | 39 |

TABLE 1-continued

| Example # | Difference Score at 1 microM | Difference Score at 10 microM | Difference Score at 20 microM |
|---|---|---|---|
| 45 | 23 | 67 | 51 |
| 46 | 16 | 61 | 45 |
| 47 | 0 | 20 | 39 |
| 49 | 24 | 84 | 40 |
| 50 | 55 | 64 | 23 |
| 53 | 0 | 15 | 39 |
| 54 | 6 | 50 | 30 |
| 55 | 69 | 67 | 66 |
| 61 | 56 | 85 | 34 |
| 62 | 69 | 76 | 19 |
| 64 | 29 | 80 | 35 |
| 66 | 8 | 73 | 69 |
| 67 | 63 | 67 | 18 |
| 71 | 3 | 52 | 79 |
| 72 | 54 | 76 | 4 |
| 74 | 76 | 25 | 0 |
| 75 | 91 | 20 | 1 |
| 78 | 44 | 49 | 20 |
| 81 | 2 | 62 | 78 |
| 86 | 83 | 77 | 29 |
| 89 | 62 | 71 | 57 |
| 92 | 37 | 68 | 43 |
| 95 | 28 | 71 | 57 |
| 97 | 66 | 58 | 48 |
| 102 | 30 | 82 | 82 |
| 110 | 89 | 34 | 3 |
| 124 | 64 | 39 | 26 |
| 120 | 83 | 59 | 1 |
| 27 | 87 | 54 | 13 |

In vivo Evaluation of MDR-1 Reversal Agents Against the Vincristine Resistant Murine Leukemia P388/VCR Implanted IP in CDF1 Mice (Table 2)

The vincristine resistant murine leukemia P388/VCR is propagated by intraperitoneal (IP) injection of $1 \times 10^6$ tumor cells into syngeneic DBA/2 mice (Charles River Laboratories, Inc.). Tumor cell ascites are harvested 5–7 days later. For drug testing, groups of 10–15 CDF1 mice (DBA/2× Balb/cF1 hybrids; Charles River Laboratories, Inc) are injected IP with 0.5 ml of diluted ascitic fluid containing $1 \times 10^6$ viable P388/VCR tumor cells. All mice are of one sex, weighing a minimum of 18 g, and all with in a 3 g weight range per test. Drugs are administered once daily, by the IP, intravenous (IV) or oral route, starting one day after tumor implantation and using a variety of treatment schedules. Mice are weighed periodically, survival is recorded for 30 days post tumor implantation, and Mean survival times are calculated for all groups of mice. Statistical analysis of Mean survival times is carried out using the Student t-test. Positive MDR-1 drug resistance reversal activity is evidenced by a statistically significant ($p \leq 0.05$) increase in Mean survival time for groups of mice treated with vincristine plus MDR-1 compound, compared to groups of mice treated with an equivalent dose of vincristine alone.

TABLE 2

IN VIVO EVALUATION OF MDR-1 REVERSAL AGENTS AGAINST THE MURINE VINCRISTINE RESISTANT P388 LEUKEMIA (P388/VCR)

| DRUG[a] | MG/KG Dose | Treat. Sched. (Days) | Route | MST (Days) | % ILS[b] | Student t-TEST[c] (p-value) |
|---|---|---|---|---|---|---|
| Placebo | 0.5 | 1–3 | IP | 9.4 | — | — |
| Vincristine | 0.4 | 1–3 | IP | 14.2 | — | — |
| Vincr. + Ex-3 | 0.4 + 50.0 | 1–3 | IP | 16.3 | +15 | <0.01 |
| | 0.4 + 25.0 | 1–3 | IP | 15.6 | +10 | <0.01 |
| Placebo | 0.5 | 1–7 | ORAL | 9.4 | — | — |
| Vincristine | 0.2 | 1–7 | IP | 13.7 | — | — |
| Vincr. + Ex-3 | 0.2 + 200 | 1–7 | ORAL | 16.4 | +20 | <0.01 |
| | 0.2 + 100 | 1–7 | ORAL | 15.8 | +15 | <0.01 |
| Placebo | 0.5 | 1–7 | IP | 9.9 | — | — |
| Vincristine | 0.2 | 1–7 | IP | 13.8 | — | — |
| Vincr. + Ex-3 | 0.2 + 75 | 1–7 | IP | 16.7 | +21 | 0.04 |
| Placebo | 0.5 | 1–7 | IP | 8.9 | — | — |
| Vincristine | 0.2 | 1–7 | IP | 14.9 | — | — |
| Vincr. + Ex-9 | 0.2 + 12.5 | 1–7 | IP | 16.8 | +13 | <0.01 |
| | 0.2 + 6.3 | 1–7 | IP | 16.4 | +10 | <0.03 |
| Placebo | 0.5 | 1–7 | IP | 13.2 | — | — |
| Vincristine | 0.2 | 1–7 | IP | 15.1 | — | — |
| Vincr. + Ex-16 | 0.2 + 25 | 1–7 | IP | 16.8 | +11 | <0.01 |
| | 0.2 + 12.5 | 1–7 | IP | 16.2 | +7 | 0.02 |
| Placebo | 0.5 | 1–7 | IP | 13.3 | — | — |
| Vincristine | 0.2 | 1–7 | IP | 14.3 | — | — |
| Vincr. + Ex-11 | 0.2 + 12.5 | 1–7 | IP | 16.3 | +14 | <0.01 |
| Placebo | 0.5 | 1–7 | IP | 13.4 | — | — |
| Vincristine | 0.2 | 1–7 | IP | 15.1 | — | — |
| Vincr. + Ex-12 | 0.2 + 50 | 1–7 | IP | 16.7 | +11 | <0.01 |
| | 0.2 + 25 | 1–7 | IP | 16.5 | +9 | <0.01 |
| Placebo | 0.5 | 1–7 | IP | 10.1 | — | — |
| Vincristine | 0.2 | 1–7 | IP | 12.5 | — | — |
| Vincr. + Ex-20 | 0.2 + 6.3 | 1–7 | IP | 13.5 | +8 | 0.03 |
| Placebo | 0.5 | 1–7 | IP | 10.1 | — | — |
| Vincristine | 0.2 | 1–7 | IP | 12.5 | — | — |
| Vincr. + Ex-21 | 0.2 + 25 | 1–7 | IP | 14.5 | +16 | <0.01 |
| | 0.2 + 12.5 | 1–7 | IP | 13.5 | +8 | 0.02 |
| Placebo | 0.5 | 1–7 | IP | 10.1 | — | — |
| Vincristine | 0.2 | 1–7 | IP | 12.7 | — | — |
| Vincr. + Ex-22 | 0.2 + 12.5 | 1–7 | IP | 15.8 | +24 | <0.01 |
| | 0.2 + 6.3 | 1–7 | IP | 15.2 | +20 | <0.01 |
| Placebo | 0.5 | 1–7 | IP | 8.7 | — | — |
| Vincristine | 0.2 | 1–7 | IP | 13.8 | — | — |
| Vincr. + Ex-17 | 0.2 + 50 | 1–5 | IP | 16.1 | +17 | 0.03 |
| | 0.2 + 25 | 1–5 | IP | 16.8 | +22 | <0.01 |
| Placebo | 0.5 | 1–7 | IP | 9.8 | — | — |
| Vincristine | 0.2 | 1–7 | IP | 14.1 | — | — |
| Vincr. + Ex-17 | 0.2 + 25 | 1–7 | IP | 20.3 | +44 | <0.01 |
| Placebo | 0.5 | 1–7 | IP | 9.3 | — | — |
| Vincristine | 0.2 | 1–7 | IP | 14.9 | — | — |
| Vincr. + Ex-17 | 0.2 + 12.5 | 1–7 | IP | 17.6 | +18 | <0.01 |
| | 0.2 + 6.3 | 1–7 | IP | 17.5 | +17 | <0.01 |
| | 0.2 + 3.1 | 1–7 | IP | 17.6 | +18 | <0.01 |
| Placebo | 0.5 | 1–7 | IP | 13.2 | — | — |
| Vincristine | 0.2 | 1–7 | IP | 15.1 | — | — |
| Vincr. + Ex-17 | 0.2 + 12.5 | 1–7 | IP | 16.8 | +11 | <0.01 |
| Placebo | 0.5 | 1–7 | IP | 10.3 | — | — |
| Vincristine | 0.2 | 1–7 | IP | 12.5 | — | — |
| Vincr. + Ex-17 | 0.2 + 6.3 | 1–7 | IP | 15.3 | +22 | <0.01 |
| Placebo | 0.5 | 1–3,6,7 | IP | 11.8 | — | — |
| Vincristine | 0.4 | 1–3,6,7 | IV | 11.4 | — | — |
| Vincr. + Ex-17 | 0.4 + 50 | 1–3,6,7 | IV | 13.4 | +18 | 0.02 |
| | 0.4 + 25 | 1–3,6,7 | IV | 13.3 | +17 | 0.01 |
| | 0.4 + 12.5 | 1–3,6,7 | IV | 12.9 | +15 | <0.01 |
| Placebo | 0.5 | 1,2 | IV | 8.4 | — | — |
| Vincristine | 0.8 | 1,2 | IV | 9.8 | — | — |
| Vincr. + Ex-17 | 0.8 + 25 | 1,2 | IV | 11.1 | +13 | <0.01 |
| Placebo | 0.5 | 1,2 | IV | 8.4 | — | — |
| Vincristine | 0.6 | 1,2 | IV | 9.6 | — | — |
| Vincr. + Ex-17 | 0.6 + 50 | 1,2 | IV | 11.1 | +16 | <0.01 |
| | 0.6 + 25 | 1,2 | IV | 10.1 | +5 | <0.03 |
| Placebo | 0.5 | 1–7 | IP | 10.1 | — | — |
| Vincristine | 0.2 | 1–7 | IP | 12.5 | — | — |
| Vincr. + Ex-17 | 0.2 + 12.5 | 1–7 | IP | 13.7 | +10 | 0.01 |
| Placebo | 0.5 | 1–7 | IP | 11.6 | — | — |
| Vincristine | 0.2 | 1–7 | IP | 12.5 | — | — |
| Vincr. + Ex-17 | 0.2 + 12.5 | 1–7 | IP | 14.7 | +18 | <0.01 |

TABLE 2-continued

IN VIVO EVALUATION OF MDR-1 REVERSAL AGENTS AGAINST THE
MURINE VINCRISTINE RESISTANT P388 LEUKEMIA (P388/VCR)

| DRUG[a] | MG/KG Dose | Treat. Sched. (Days) | Route | MST (Days) | % ILS[b] | Student t-TEST[c] (p-value) |
|---|---|---|---|---|---|---|
| Placebo | 0.5 | 1–7 | IP | 11.2 | — | — |
| Vincristine | 0.2 | 1–7 | IP | 12.3 | — | — |
| Vincr. + Ex-17 | 0.2 + 12.5 | 1–7 | IP | 15.8 | +28 | <0.01 |
| Placebo | 0.5 | 1–7 | IP | 9.2 | — | — |
| Vincristine | 0.2 | 1–7 | IP | 12.6 | — | — |
| Vincr. + Ex-17 | 0.2 + 25 | 1–7 | IP | 14.7 | +16 | <0.03 |
| | 0.2 + 12.5 | 1–7 | IP | 16.8 | +33 | <0.01 |
| | 0.2 + 6.3 | 1–7 | IP | 14.9 | +18 | <0.01 |
| | 0.2 + 3.1 | 1–7 | IP | 13.8 | +10 | <0.03 |
| Placebo | 0.5 | 1,5,9 | IP | 9.3 | — | — |
| Vincristine | 0.6 | 1,5,9 | IP | 11.5 | — | — |
| Vincr. + Ex-17 | 0.6 + 25 | 1,5,9 | IP | 15.8 | +38 | <0.01 |
| | 0.6 + 12.5 | 1,5,9 | IP | 14.1 | +23 | <0.01 |
| | 0.6 + 6.3 | 1,5,9 | IP | 12.9 | +12 | <0.01 |
| Placebo | 0.5 | 1–7 | IP | 13.2 | — | — |
| Vincristine | 0.2 | 1–7 | IP | 14.7 | — | — |
| Vincr. + Ex-37 | 0.2 + 6.3 | 1–7 | IP | 15.7 | +7 | 0.04 |
| Placebo | 0.5 | 1–7 | IP | 10.3 | — | — |
| Vincristine | 0.2 | 1–7 | IP | 12.5 | — | — |
| Vincr. + Ex-37 | 0.2 + 12.5 | 1–7 | IP | 16.1 | +29 | <0.01 |
| | 0.2 + 6.3 | 1–7 | IP | 14.6 | +17 | 0.02 |
| Placebo | 0.5 | 1–7 | IP | 9.2 | — | — |
| Vincristine | 0.2 | 1–7 | IP | 12.6 | — | — |
| Vincr. + Ex-37 | 0.2 + 25 | 1–7 | IP | 14.7 | +17 | 0.01 |
| | 0.2 + 12.5 | 1–7 | IP | 15.5 | +23 | <0.01 |
| | 0.2 + 6.3 | 1–7 | IP | 13.8 | +10 | <0.02 |
| | 0.2 + 3.1 | 1–7 | IP | 14.1 | +12 | <0.01 |
| Placebo | 0.5 | 1–7 | IP | 9.8 | — | — |
| Vincristine | 0.2 | 1–7 | IP | 12.7 | — | — |
| Vincr. + Ex-37 | 0.2 + 12.5 | 1–7 | IP | 15.0 | +18 | <0.01 |
| | 0.2 + 3.1 | 1–7 | IP | 14.2 | +12 | <0.01 |
| Placebo | 0.5 | 1–7 | IP | 11.4 | — | — |
| Vincristine | 0.2 | 1–7 | IP | 16.0 | — | — |
| Vincr. + Ex-37 | 0.2 + 12.5 | 1–7 | IP | 17.9 | +12 | 0.01 |
| Placebo | 0.5 | 1–7 | IP | 10.3 | — | — |
| Vincristine | 0.2 | 1–7 | IP | 15.4 | — | — |
| Vincr. + Ex-37 | 0.2 + 12.5 | 1–7 | IP | 18.1 | +18 | <0.01 |
| Placebo | 0.5 | 1–7 | IP | 9.3 | — | — |
| Vincristine | 0.2 | 1–7 | IP | 14.9 | — | — |
| Vincr. + Ex-37 | 0.2 + 12.5 | 1–7 | IP | 19.1 | +28 | <0.01 |
| | 0.2 + 6.3 | 1–7 | IP | 17.7 | +19 | <0.01 |
| | 0.2 + 3.1 | 1–7 | IP | 16.6 | +11 | 0.03 |
| Placebo | 0.5 | 1–7 | IP | 13.2 | — | — |
| Vincristine | 0.2 | 1–7 | IP | 15.1 | — | — |
| Vincr. + Ex-37 | 0.2 + 12.5 | 1–7 | IP | 17.1 | +13 | <0.01 |
| Placebo | 0.5 | 1–7 | IP | 10.3 | — | — |
| Vincristine | 0.2 | 1–7 | IP | 12.5 | — | — |
| Vincr. + Ex-1 | 0.2 + 6.3 | 1–7 | IP | 14.1 | +13 | 0.02 |
| Placebo | 0.5 | 1–7 | IP | 11.2 | — | — |
| Vincristine | 0.2 | 1–7 | IP | 12.3 | — | — |
| Vincr. + Ex-46 | 0.2 + 25 | 1–7 | IP | 16.7 | +36 | <0.01 |
| | 0.2 + 12.5 | 1–7 | IP | 14.7 | +20 | <0.01 |
| Placebo | 0.5 | 1–7 | IP | 10.1 | — | — |
| Vincristine | 0.2 | 1–7 | IP | 12.5 | — | — |
| Vincr. + Ex-14 | 0.2 + 6.3 | 1–7 | IP | 14.3 | +14 | <0.01 |
| Placebo | 0.5 | 1–7 | IP | 9.7 | — | — |
| Vincristine | 0.2 | 1–7 | IP | 11.2 | — | — |
| Vincr. + Ex-26 | 0.2 + 25 | 1–7 | IP | 15.8 | 441 | <0.01 |
| | 0.2 + 12.5 | 1–7 | IP | 15.0 | +34 | <0.01 |
| | 0.2 + 6.3 | 1–7 | IP | 13.8 | +23 | <0.01 |
| Placebo | 0.5 | 1–7 | IP | 9.7 | — | — |
| Vincristine | 0.2 | 1–7 | IP | 11.2 | — | — |
| Vincr. + Ex-112 | 0.2 + 50 | 1–7 | IP | 14.2 | +26 | 0.02 |
| | 0.2 + 25 | 1–7 | IP | 16.3 | +45 | <0.01 |
| | 0.2 + 12.5 | 1–7 | IP | 16.2 | +45 | <0.01 |
| Placebo | 0.5 | 1–7 | IP | 9.7 | — | — |
| Vincristine | 0.2 | 1–7 | IP | 11.2 | — | — |
| Vincr. + Ex-33 | 0.2 + 50 | 1–7 | IP | 16.6 | +48 | <0.01 |
| | 0.2 + 25 | 1–7 | IP | 15.6 | +39 | <0.01 |
| | 0.2 + 12.5 | 1–7 | IP | 15.1 | +35 | <0.01 |

[a]Drugs were administered IP, IV or ORAL on days indicated relative to tumor implatation.
[b]% ILS-Percent Increase in Life Span relative to Vincristine treatment alone.

TABLE 2-continued

IN VIVO EVALUATION OF MDR-1 REVERSAL AGENTS AGAINST THE MURINE VINCRISTINE RESISTANT P388 LEUKEMIA (P388/VCR)

| DRUG[a] | MG/KG Dose | Treat. Sched. (Days) | Route | MST (Days) | % ILS[b] | Student t-TEST[c] (p-value) |
|---|---|---|---|---|---|---|

[c]Indicates significant increase (p ≤ .05) in Mean Survival Time, compared to Vincristine treatment alone.
Vincr. = Vincristine
Ex = Example Number

In vivo Evaluation of MDR-1 Reversal Agents Against the Human Epidermoid Carcinoma KB/8.5 Implanted SC in Athymic "Nude" Mice (Table 3)

The multiple drug resistant human epidermoid carcinoma KB/8.5 is propagated in medium containing colchicine (10 nanograms/ml) to maintain drug resistance. Colchicine is removed from the medium, for two cell passages, prior to subcutaneous (SC) implant of $8 \times 10^6$ KBy8.5 tumor cells into athymic "nude" mice (Harlan Sprague Dawley). Approximately 7–10 days post tumor implant, the SC tumors attained a mass of 100–300 mgs. At this time (Day 0 of the test period) mice are allocated to treatment groups of 5–10 mice per group, so that the groups have a mean tumor mass as closely comparable as possible. Drug treatment is administered one day later, according to the following treatment protocol: doxorubicin is administered as a single intravenous dose (8 mg/kg), and either placebo (normal saline) or MDR-1 reversal compound is administered in two subcutaneous doses (12.5–200 mg/kg/dose) given 2 hours before and again at 2 hours after the single IV dose of doxorubicin. Individual mouse tumor mass and mean tumor mass for each treatment group is determined on Day+14 and Day+21 of the test period. For each treatment group, the Relative Tumor Growth, RTG, is calculated as follows:

$$RTG = \text{Mean Tumor Mass on Day +14 or +Day/Mean Tumor Mass on Day 0}$$

Statistical analysis of Log Relative Tumor Growth is carried out using the Student t-test. Transformation of the data from absolute mean tumor mass (rags tumor mass) to Log Relative Tumor Growth prior to statistical analysis has two beneficial effects:

1) it corrects the data for differences in mean tumor mass of the different treatment groups at the start of the test period (Day 0); and 2) the Log transformation of the data more adequately reflects the exponential growth pattern of the SC tumors and makes the use of the Student t-test more appropriate. Positive MDR-1 drug activity is indicated by a statistically significant (p≦0.05) reduction in Relative Tumor Growth for groups treated with doxorubicin plus MDR-1 compound, compared to control groups treated with an equivalent dose of doxorubicin alone.

TABLE 3

IN VIVO EVALUATION OF MDR-1 REVERSAL AGENTS AGAINST THE HUMAN EPIDERMOID CARCINOMA KB/8.5 IMPLANTED SC IN ATHYMIC 'NUDE' MICE RELATIVE TUMOR GROWTH

| Drug Treatment[a] (Mg/Kg/Dose) | Relative[b] Tumor Growth Day 14 | Statistics[c] (p-value) | Relative Tumor Growth Day 21 | Statistics (p-value) |
|---|---|---|---|---|
| Saline | 8.78 | — | 11.42 | — |
| Doxorubicin (8) | 6.30 | — | 10.26 | — |
| Dox (8) + Ex-26 (100) | 3.87 | <0.01 | 6.69 | <0.01 |
| Dox (8) + Ex-26 (50) | 4.83 | 0.01 | 7.87 | 0.03 |
| Dox (8) + Ex-26 (25) | 5.46 | 0.12 | 9.62 | 0.39 |
| Dox (8) + Ex-26 (12.5) | 7.08 | 0.76 | 8.93 | 0.17 |
| Saline | 11.03 | — | 15.23 | — |
| Doxorubicin (8) | 7.44 | — | 12.82 | — |
| Dox (8) + Ex-26 (150) | Toxic | — | Toxic | — |
| Dox (8) + Ex-26 (100) | 3.97 | <0.01 | 6.87 | <0.01 |
| Dox (8) + Ex-26 (50) | 4.8 | <0.01 | 8.31 | 0.01 |
| Dox (8) + Ex-26 (25) | 6.25 | 0.27 | 9.06 | 0.02 |
| Dox (8) + Ex-26 (12.5) | 6.87 | 0.53 | 10.14 | 0.13 |
| Saline | 7.90 | — | 13.54 | — |
| Doxorubicin (8) | 4.59 | — | 8.37 | — |
| Dox (8) + Ex-26 (200) | Toxic | — | Toxic | — |
| Dox (8) + Ex-26 (100) | 2.43 | <0.01 | 3.84 | <0.01 |
| Dox (8) + Ex-26 (50) | 2.82 | <0.01 | 4.62 | <0.01 |
| Dox (8) + Ex-26 (25) | 3.30 | 0.04 | 5.49 | 0.02 |
| Dox (8) + Ex-26 (12.5) | 4.97 | 0.76 | 8.33 | 0.54 |
| Saline | 5.98 | — | 10.34 | — |
| Doxorubicin (8) | 2.88 | — | 5.69 | — |
| Dox (8) + Ex-26 (100) | 0.77 | <0.01 | 1.70 | <0.01 |
| Dox (8) + Ex-26 (75) | 1.75 | 0.01 | 3.49 | <0.01 |
| Dox (8) + Ex-26 (50) | 2.51 | 0.16 | 3.95 | <0.01 |
| Saline | 10.63 | — | 25.28 | — |

TABLE 3-continued

IN VIVO EVALUATION OF MDR-1 REVERSAL AGENTS AGAINST
THE HUMAN EPIDERMOID CARCINOMA KB/8.5 IMPLANTED SC
IN ATHYMIC 'NUDE' MICE
RELATIVE TUMOR GROWTH

| Drug Treatment[a]<br>(Mg/Kg/Dose) | Relative[b]<br>Tumor<br>Growth<br>Day 14 | Statistics[c]<br>(p-value) | Relative<br>Tumor<br>Growth<br>Day 21 | Statistics<br>(p-value) |
|---|---|---|---|---|
| Doxorubicin (8) | 7.30 | — | 16.05 | — |
| Dox (8) + Ex-17 (100) | 4.95 | 0.04 | 10.39 | 0.02 |
| Dox (8) + Ex-17 (75) | 4.04 | <0.01 | 9.18 | <0.01 |
| Dox (8) + Ex-17 (50) | 4.33 | <0.01 | 7.85 | <0.01 |
| Saline | 13.13 | — | 23.44 | — |
| Doxorubicin (8) | 6.73 | — | 10.99 | — |
| Dox (8) + Ex-17 (150) | 2.24 | <0.01 | 3.35 | <0.01 |
| Dox (8) + Ex-17 (100) | 4.53 | <0.01 | 6.22 | <0.01 |
| Dox (8) + Ex-17 (75) | 4.38 | <0.01 | 7.37 | <0.01 |
| Saline | 7.90 | — | 13.54 | — |
| Doxorubicin (8) | 4.59 | — | 8.37 | — |
| Dox (8) + Ex-17 (200) | 2.7 | <0.01 | 5.30 | 0.02 |
| Dox (8) + Ex-17 (100) | 2.85 | <0.01 | 4.99 | 0.01 |
| Dox (8) + Ex-17 (50) | 3.43 | 0.05 | 6.09 | 0.06 |
| Dox (8) + Ex-17 (25) | 5.09 | 0.83 | 9.55 | 0.83 |
| Dox (8) + Ex-17 (12.5) | 3.97 | 0.26 | 8.58 | 0.66 |
| Saline | 9.27 | — | 15.21 | — |
| Doxorubicin (8) | 6.17 | — | 11.13 | — |
| Dox (8) + Ex-33 (200) | 2.20 | <0.01 | 3.98 | <0.01 |
| Dox (8) + Ex-33 (100) | 3.28 | <0.01 | 6.38 | <0.01 |
| Dox (8) + Ex-33 (50) | 3.02 | <0.01 | 6.04 | <0.01 |
| Dox (8) + Ex-33 (25) | 2.85 | <0.01 | 5.20 | <0.01 |
| Dox (8) + Ex-33 (12.5) | 2.41 | <0.01 | 4.09 | <0.01 |
| Saline | 9.51 | — | 18.00 | — |
| Doxorubicin (8) | 5.66 | — | 9.29 | — |
| Dox (8) + Ex-33 (200) | 2.71 | <0.01 | 5.94 | <0.01 |
| DOX (8) + Ex-33 (100) | 3.47 | <0.01 | 5.63 | <0.01 |
| Dox (8) + Ex-33 (50) | 3.85 | <0.01 | 7.55 | 0.13 |
| Dox (8) + Ex-33 (25) | 3.97 | 0.01 | 7.70 | 0.17 |
| Dox (8) + Ex-33 (12.5) | 3.88 | <0.01 | 7.88 | 0.13 |
| Saline | 17.50 | — | 31.38 | — |
| Doxorubicin (8) | 6.83 | — | 15.06 | — |
| Dox (8) + Ex-112 (200) | 4.31 | <0.01 | 8.08 | <0.01 |
| Dox (8) + Ex-112 (100) | 3.20 | <0.01 | 7.26 | <0.01 |
| Dox (8) + Ex-112 (50) | 3.36 | <0.01 | 9.32 | 0.03 |
| Dox (8) + Ex-112 (25) | 4.92 | 0.06 | 9.93 | 0.07 |
| Dox (8) + Ex-112 (12.5) | 4.71 | 0.02 | 11.38 | 0.20 |
| Saline | 9.51 | — | 18.00 | — |
| Doxorubicin (8) | 5.66 | — | 9.29 | — |
| Dox (8) + Ex-112 (200) | 2.75 | <0.01 | 5.97 | <0.01 |
| Dox (8) + Ex-112 (100) | 3.66 | <0.01 | 6.82 | 0.03 |
| Dox (8) + Ex-112 (50) | 4.97 | 0.19 | 6.99 | 0.06 |
| Dox (8) + Ex-112 (25) | 4.99 | 0.26 | 7.34 | 0.08 |
| Dox (8) + Ex-112 (12.5) | 4.33 | 0.06 | 6.47 | 0.01 |
| Saline | 6.49 | — | 10.18 | — |
| Doxorubicin (8) | 4.66 | — | 7.70 | — |
| Dox (8) + Ex-112 (200) | 2.35 | <0.01 | 3.81 | <0.01 |
| Dox (8) + Ex-112 (25) | 4.51 | 0.39 | 7.21 | 0.38 |
| Dox (8) + Ex-112 (12.5) | 4.75 | 0.52 | 6.58 | 0.15 |
| Saline | 17.50 | — | 31.38 | — |
| Doxorubicin (8) | 6.83 | — | 15.06 | — |
| Dox (8) + Ex-3 (200) | 3.34 | <0.01 | 7.34 | <0.01 |
| Dox (8) + Ex-3 (100) | 3.92 | <0.01 | 8.87 | 0.01 |
| Dox (8) + Ex-3 (50) | 4.29 | 0.01 | 8.38 | <0.01 |
| Dox (8) + Ex-3 (25) | 5.31 | 0.09 | 11.29 | 0.12 |
| Dox (8) + Ex-3 (12.5) | 4.39 | <0.01 | 10.68 | 0.10 |
| Saline | 8.31 | — | 12.15 | — |
| Doxorubicin (8) | 4.91 | — | 9.34 | — |
| Dox (8) + Ex-3 (12.5) | 4.37 | 0.23 | 8.19 | 0.14 |
| Saline | 6.49 | — | 10.18 | — |
| Doxorubicin (8) | 4.66 | — | 7.70 | — |
| Dox (8) + Ex-3 (200) | 3.06 | <0.01 | 5.49 | 0.02 |
| Dox (8) + Ex-3 (25) | 5.73 | 0.95 | 8.02 | 0.61 |
| Dox (8) + Ex-3 (12.5) | 5.19 | 0.75 | 7.97 | 0.54 |
| Saline | 17.50 | — | 31.38 | — |
| Doxorubicin (8) | 6.83 | — | 15.06 | — |
| Dox (8) + Ex-14 (200) | 4.59 | 0.02 | 7.84 | <0.01 |
| Dox (8) + Ex-14 (100) | 3.46 | <0.01 | 6.25 | <0.01 |
| Dox (8) + Ex-14 (50) | 4.14 | <0.01 | 10.03 | 0.04 |

TABLE 3-continued

IN VIVO EVALUATION OF MDR-1 REVERSAL AGENTS AGAINST THE HUMAN EPIDERMOID CARCINOMA KB/8.5 IMPLANTED SC IN ATHYMIC 'NUDE' MICE RELATIVE TUMOR GROWTH

| Drug Treatment[a] (Mg/Kg/Dose) | Relative[b] Tumor Growth Day 14 | Statistics[c] (p-value) | Relative Tumor Growth Day 21 | Statistics (p-value) |
|---|---|---|---|---|
| Dox (8) + Ex-14 (25) | 5.56 | 0.19 | 10.97 | 0.16 |
| Saline | 5.98 | — | 10.34 | — |
| Doxorubicin (8) | 2.88 | — | 5.69 | — |
| Dox (8) + Ex-14 (100) | 2.94 | 0.43 | 5.40 | 0.41 |
| Dox (8) + Ex-14 (75) | 2.90 | 0.48 | 5.86 | 0.48 |
| Dox (8) + Ex-14 (50) | 3.08 | 0.64 | 5.90 | 0.64 |
| Dox (8) + Ex-14 (25) | 2.56 | 0.25 | 5.06 | 0.29 |
| Saline | 11.47 | — | 19.96 | — |
| Doxorubicin (8) | 5.15 | — | 10.08 | — |
| Dox (8) + Ex-32 (200) | 2.23 | <0.01 | 3.90 | <0.01 |
| Dox (8) + Ex-32 (100) | 4.59 | 0.32 | 9.20 | 0.44 |
| Dox (8) + Ex-32 (50) | 6.56 | 0.90 | 12.91 | 0.93 |
| Dox (8) + Ex-32 (25) | 5.69 | 0.70 | 11.30 | 0.79 |
| Dox (8) + Ex-32 (12.5) | 9.50 | 1.00 | 19.93 | 1.00 |
| Saline | 11.14 | — | 18.56 | — |
| Doxorubicin (8) | 8.38 | — | 13.55 | — |
| Dox (8) + Ex-32 (200) | 4.32 | <0.01 | 7.33 | <0.01 |
| Dox (8) + Ex-32 (100) | 5.37 | <0.01 | 10.66 | 0.07 |
| Dox (8) + Ex-32 (50) | 6.73 | 0.13 | 12.43 | 0.39 |
| Saline | 9.22 | — | 15.15 | — |
| Doxorubicin (8) | 9.78 | — | 19.57 | — |
| Dox (8) + Ex-47 (200) | 5.60 | 0.04 | 11.04 | 0.16 |
| Dox (8) + Ex-47 (100) | 6.12 | 0.08 | 10.09 | 0.08 |
| Dox (8) + Ex-47 (50) | 7.96 | 0.47 | 16.54 | 0.75 |
| Dox (8) + Ex-47 (25) | 5.09 | 0.02 | 9.73 | 0.05 |
| Dox (8) + Ex-47 (12.5) | 8.79 | 0.39 | 17.53 | 0.57 |
| Saline | 7.90 | — | 13.54 | — |
| Doxorubicin (8) | 4.59 | — | 8.37 | — |
| Dox (8) + Ex-41 (200) | 2.41(tox) | <0.01 | 4.57(tox) | 0.01 |
| Dox (8) + Ex-41 (100) | 3.13 | 0.01 | 6.28 | 0.12 |
| Dox (8) + Ex-41 (50) | 4.21 | 0.38 | 7.10 | 0.27 |
| Dox (8) + Ex-41 (25) | 3.80 | 0.10 | 6.15 | 0.06 |
| Dox (8) + Ex-41 (12.5) | 4.01 | 0.30 | 7.27 | 0.26 |
| Saline | 10.63 | — | 25.28 | — |
| Doxorubicin (8) | 7.30 | — | 16.05 | — |
| Dox (8) + Ex-41 (100) | 5.14 | 0.06 | 10.39 | 0.02 |
| Dox (8) + Ex-41 (75) | 4.64 | <0.01 | 8.54 | <0.01 |
| Dox (8) + Ex-41 (50) | 8.63 | 0.58 | 15.08 | 0.13 |
| Saline | 10.63 | — | 25.28 | — |
| Doxorubicin (8) | 7.30 | — | 16.05 | — |
| Dox (8) + Ex-46 (100) | 4.62 | 0.02 | 10.91 | 0.03 |
| Dox (8) + Ex-46 (75) | 5.18 | 0.05 | 10.23 | 0.01 |
| Dox (80 + Ex-46 (50) | 4.12 | <0.01 | 8.83 | <0.01 |
| Saline | 16.39 | — | 24.75 | — |
| Doxorubicin (8) | 7.34 | — | 12.53 | — |
| Dox (8) + Ex-46 (200) | 4.69 | <0.01 | 8.99 | 0.02 |
| Dox (8) + Ex-46 (25) | 5.79 | 0.08 | 9.65 | 0.08 |
| Saline | 10.64 | — | 19.73 | — |
| Doxorubicin (8) | 4.18 | — | 6.87 | — |
| Dox (8) + Ex-49 (200) | 3.39 | 0.10 | 6.13 | 0.29 |
| Dox (8) + Ex-49 (100) | 2.22 | <0.01 | 3.03 | 0.01 |
| Dox (8) + Ex-49 (50) | 4.11 | 0.48 | 8.28 | 0.73 |
| Dox (8) + Ex-49 (25) | 2.88 | 0.03 | 5.04 | 0.06 |
| Dox (8) + Ex-49 (12.5) | 3.32 | 0.15 | 6.41 | 0.34 |
| Saline | 11.14 | — | 18.56 | — |
| Doxorubicin (8) | 8.38 | — | 13.55 | — |
| Dox (8) + Ex-49 (200) | 3.07 | <0.01 | 4.65 | <0.01 |
| Dox (8) + Ex-49 (100) | 5.00 | <0.01 | 7.47 | <0.01 |
| Dox (8) + Ex-49 (50) | 5.60 | 0.01 | 11.17 | 0.14 |
| Saline | 11.47 | — | 19.96 | — |
| Doxorubicin (8) | 5.15 | — | 10.08 | — |
| Dox (8) + Ex-50 (200) | 4.34 | 0.17 | 6.87 | 0.04 |
| Dox (8) + Ex-50 (100) | 3.30 | 0.03 | 7.08 | 0.11 |
| Dox (8) + Ex-50 (50) | 4.20 | 0.20 | 8.76 | 0.39 |
| Dox (8) + Ex-50 (25) | 4.26 | 0.21 | 7.86 | 0.19 |
| Dox (8) + Ex-50 (12.5) | 5.19 | 0.50 | 10.30 | 0.63 |
| Saline | 12.17 | — | 18.87 | — |
| Doxorubicin (8) | 7.80 | — | 11.05 | — |
| Dox (8) + Ex-55 (200) | 4.54 | <0.01 | 7.15 | 0.02 |

TABLE 3-continued

IN VIVO EVALUATION OF MDR-1 REVERSAL AGENTS AGAINST
THE HUMAN EPIDERMOID CARCINOMA KB/8.5 IMPLANTED SC
IN ATHYMIC 'NUDE' MICE
RELATIVE TUMOR GROWTH

| Drug Treatment[a]<br>(Mg/Kg/Dose) | Relative[b]<br>Tumor<br>Growth<br>Day 14 | Statistics[c]<br>(p-value) | Relative<br>Tumor<br>Growth<br>Day 21 | Statistics<br>(p-value) |
|---|---|---|---|---|
| Dox (8) + Ex-55 (100) | 5.80 | 0.07 | 12.37 | 0.61 |
| Dox (8) + Ex-55 (50) | 7.10 | 0.15 | 12.20 | 0.40 |
| Dox (8) + Ex-55 (25) | 6.39 | 0.15 | 9.31 | 0.25 |
| Dox (8) + Ex-55 (12.5) | 6.13 | 0.09 | 9.05 | 0.19 |
| Saline | 6.15 | — | 10.19 | |
| Doxorubicin (8) | 3.81 | — | 5.82 | — |
| Cox (8) + Ex-55 (25) | 3.86 | 0.63 | 5.65 | 0.52 |
| Dox (8) + Ex-55 (12.5) | 3.94 | 0.68 | 6.03 | 0.65 |
| Saline | 9.27 | — | 15.21 | — |
| Doxorubicin (8) | 6.17 | — | 11.13 | — |
| Dox (8) + Ex-61 (200) | 2.57 | <0.01 | 4.51 | <0.01 |
| Dox (8) + Ex-61 (100) | 3.49 | <0.01 | 6.86 | 0.01 |
| Dox (8) + Ex-61 (50) | 6.26 | 0.53 | 8.66 | 0.08 |
| Dox (8) + Ex-61 (25) | 4.64 | 0.10 | 8.74 | 0.08 |
| Dox (8) + Ex-61 (12.5) | 4.67 | 0.01 | 8.88 | <0.01 |
| Saline | 16.39 | — | 24.75 | — |
| Doxorubicin (8) | 7.34 | — | 12.53 | — |
| Dox (8) + Ex-61 (200) | 2.40 | <0.01 | 6.13 | <0.01 |
| Dox (8) + Ex-61 (25) | 5.51 | 0.05 | 10.20 | 0.16 |
| Saline | 7.79 | — | 12.55 | — |
| Doxorubicin (8) | 5.98 | — | 10.65 | — |
| Dox (8) + Ex-78 (200) | 5.44 | 0.34 | 14.91 | 0.92 |
| Dox (8) + Ex-78 (100) | 4.28 | 0.06 | 11.07 | 0.53 |
| Dox (8) + Ex-78 (50) | 4.38 | 0.10 | 7.09 | 0.13 |
| Dox (8) + Ex-78 (25) | 5.56 | 0.54 | 10.14 | 0.63 |
| Dox (8) + Ex-78 (12.5) | 6.22 | 0.72 | 10.27 | 0.65 |
| Saline | 11.14 | — | 18.56 | — |
| Doxorubicin (8) | 8.38 | — | 13.55 | — |
| Dox (8) + Ex-78 (200) | 4.07 | <0.01 | 8.60 | <0.01 |
| Dox (8) + Ex-78 (100) | 5.30 | <0.01 | 10.72 | 0.06 |
| Dox (8) + Ex-78 (50) | 4.84 | <0.01 | 10.89 | 0.13 |
| Saline | 9.27 | — | 15.21 | — |
| Doxorubicin (8) | 6.17 | — | 11.13 | — |
| Dox (8) + Ex-62 (200) | 4.27(tox) | 0.09 | 8.57(tox) | 0.11 |
| Dox (8) + Ex-62 (100) | 4.25 | 0.04 | 6.08 | <0.01 |
| Dox (8) + Ex-62 (50) | 5.40 | 0.29 | 9.47 | 0.19 |
| Dox (8) + Ex-62 (25) | 5.99 | 0.46 | 12.17 | 0.72 |
| Dox (8) + Ex-62 (12.5) | 6.24 | 0.52 | 10.17 | 0.37 |
| Saline | 16.39 | — | 24.75 | — |
| Doxorubicin | 7.34 | — | 12.53 | — |
| Dox (8) + Ex-62 (200) | 3.15 | <0.01 | 7.55 | <0.01 |
| Dox (8) + Ex-62 (25) | 6.18 | 0.15 | 9.09 | 0.05 |
| Saline | 9.22 | — | 15.15 | — |
| Doxorubicin (8) | 9.78 | — | 19.57 | — |
| Dox (8) + Ex-92 (200) | 4.84 | 0.02 | 8.71 | 0.03 |
| Dox (8) + Ex-92 (100) | 4.98 | 0.02 | 10.48 | 0.09 |
| Dox (8) + Ex-92 (50) | 8.09 | 0.46 | 11.75 | 0.26 |
| Dox (8) + Ex-92 (25) | 5.76 | 0.06 | 12.05 | 0.21 |
| Dox (8) + Ex-92 (12.5) | 7.20 | 0.30 | 12.75 | 0.30 |
| Saline | 12.15 | — | 17.79 | — |
| Doxorubicin (8) | 8.11 | — | 14.17 | — |
| Dox (8) + Ex-66 (200) | 4.26 | <0.01 | 7.07 | <0.01 |
| Dox (8) + Ex-66 (100) | 5.73 | 0.07 | 8.17 | 0.04 |
| Dox (8) + Ex-66 (50) | 6.93 | 0.24 | 9.72 | 0.13 |
| Dox (8) + Ex-66 (25) | 6.88 | 0.20 | 10.52 | 0.13 |
| Dox (8) + Ex-66 (12.5) | 7.01 | 0.27 | 11.97 | 0.31 |
| Saline | 7.99 | — | 12.58 | — |
| Doxorubicin (8) | 6.13 | — | 11.58 | — |
| Dox (8) + Ex-66 (50) | 6.06 | 0.56 | 9.90 | 0.22 |
| Dox (8) + Ex-66 (25) | 6.33 | 0.67 | 9.89 | 0.23 |
| Dox (8) + Ex-66 (12.5) | 5.16 | 0.17 | 7.41 | <0.01 |
| Saline | 8.89 | — | 12.06 | — |
| Doxorubicin (8) | 6.36 | — | 8.63 | — |
| Dox (8) + Ex-74 (200) | 5.90 | 0.28 | 8.92 | 0.70 |
| Dox (8) + Ex-74 (100) | 4.28 | <0.01 | 6.25 | 0.17 |
| Dox (8) + Ex-74 (50) | 6.61 | 0.47 | 9.18 | 0.71 |
| Dox (8) + Ex-74 (25) | 6.88 | 0.76 | 9.11 | 0.71 |
| Dox (8) + Ex-74 (12.5) | 6.47 | 0.62 | 9.00 | 0.79 |
| Saline | 12.40 | — | 19.67 | — |

TABLE 3-continued

IN VIVO EVALUATION OF MDR-1 REVERSAL AGENTS AGAINST THE HUMAN EPIDERMOID CARCINOMA KB/8.5 IMPLANTED SC IN ATHYMIC 'NUDE' MICE RELATIVE TUMOR GROWTH

| Drug Treatment[a] (Mg/Kg/Dose) | Relative[b] Tumor Growth Day 14 | Statistics[c] (p-value) | Relative Tumor Growth Day 21 | Statistics (p-value) |
|---|---|---|---|---|
| Doxorubicin (8) | 7.19 | — | 12.05 | — |
| Dox (8) + Ex-74 (200) | 6.60 | 0.22 | 8.35 | 0.07 |
| Dox (8) + Ex-74 (100) | 6.86 | 0.33 | 11.43 | 0.61 |
| Saline | 6.32 | — | 9.53 | — |
| Doxorubicin (8) | 6.84 | — | 10.84 | — |
| Dox (8) + Ex-97 (200) | 4.86 | 0.10 | 8.27 | 0.13 |
| Dox (8) + Ex-97 (100) | 5.40 | 0.19 | 11.68 | 0.62 |
| Dox (8) + Ex-97 (50) | 5.39 | 0.23 | 8.66 | 0.15 |
| Dox (8) + Ex-97 (25) | 4.23 | 0.02 | 9.12 | 0.20 |
| Dox (8) + Ex-97 (12.5) | 8.64 | 0.92 | 14.09 | 0.92 |
| Saline | 9.28 | — | 15.09 | — |
| Doxorubicin (8) | 7.27 | — | 12.60 | — |
| Dox (8) + Ex-97 (200) | 7.26 | 0.55 | 12.62 | 0.56 |
| Dox (8) + Ex-97 (100) | 7.80 | 0.68 | 13.13 | 0.57 |
| Dox (8) + Ex-97 (50) | 8.37 | 0.74 | 12.91 | 0.53 |
| Dox (8) + Ex-97 (25) | 8.31 | 0.80 | 11.60 | 0.35 |
| Dox (8) + Ex-97 (12.5) | 10.52 | 0.96 | 14.89 | 0.79 |
| Saline | 9.99 | — | 13.89 | — |
| Doxorubicin (8) | 5.74 | — | 10.41 | — |
| Dox (8) + Ex-81 (200) | 5.38 | 0.34 | 8.71 | 0.14 |
| Dox (8) + Ex-81 (100) | 7.75 | 0.97 | 11.57 | 0.71 |
| Dox (8) + Ex-81 (50) | 5.38 | 0.33 | 10.88 | 0.60 |
| Dox (8) + Ex-81 (25) | 5.31 | 0.25 | 10.51 | 0.49 |
| Dox (8) + Ex-81 (12.5) | 5.47 | 0.43 | 9.52 | 0.30 |
| Saline | 9.28 | — | 15.09 | — |
| Doxorubicin (8) | 7.27 | — | 12.60 | — |
| Dox (8) + Ex-81 (200) | 9.16 | 0.88 | 12.03 | 0.42 |
| Dox (8) + Ex-81 (100) | 8.82 | 0.85 | 14.37 | 0.75 |
| Dox (8) + Ex-81 (50) | 8.83 | 0.88 | 12.11 | 0.47 |
| Dox (8) + Ex-81 (25) | 10.22 | 0.96 | 20.00 | 0.66 |
| Saline | 12.14 | — | 24.57 | — |
| Doxorubicin (8) | 7.76 | — | 12.44 | — |
| Dox (8) + Ex-67 (200) | 4.27 | <0.01 | 8.55 | <0.01 |
| Dox (8) + Ex-67 (100) | 4.16 | <0.01 | 7.76 | 10.01 |
| Dox (8) + Ex-67 (50) | 5.12 | 0.03 | 11.52 | 0.36 |
| Dox (8) + Ex-67 (25) | 5.27 | 0.04 | 11.73 | 0.35 |
| Dox (8) + Ex-67 (12.5) | 5.00 | 0.02 | 9.81 | 0.12 |
| Saline | 16.39 | — | 24.75 | — |
| Doxorubicin (8) | 7.34 | — | 12.53 | — |
| Dox (8) + Ex-67 (25) | 5.62 | 0.01 | 12.54 | 0.26 |
| Saline | 14.56 | — | 15.95 | — |
| Doxorubicin (8) | 4.76 | — | 7.70 | — |
| Dox (8) + Ex-64 (200) | 3.13 | <0.01 | 5.39 | 0.03 |
| Dox (8) + Ex-64 (25) | 5.62 | 0.75 | 5.14 | 0.02 |
| Dox (8) + Ex-64 (12.5) | 5.62 | 0.77 | 7.23 | 0.24 |
| Saline | 6.49 | — | 10.18 | — |
| Doxorubicin (8) | 4.66 | — | 7.70 | — |
| Dox (8) + Ex-64 (200) | 2.91 | <0.01 | 5.87 | 0.05 |
| Dox (8) + Ex-64 (25) | 3.86 | 0.06 | 6.21 | 0.09 |
| Dox (8) + Ex-64 (12.5) | 4.65 | 0. | 6.89 | 0.22 |
| Saline | 7.79 | — | 12.55 | — |
| Doxorubicin (8) | 5.98 | — | 10.65 | — |
| Dox 8 + Ex-64 (200) | 4.86 | 0.13 | 9.46 | 0.38 |
| Dox 8 + Ex-64 (100) | 4.06 | 0.05 | 8.00 | 0.27 |
| Dox 8 + Ex-64 (50) | 5.17 | 0.40 | 9.02 | 0.46 |
| Dox 8 + Ex-64 (25) | 6.61 | 0.84 | 11.48 | 0.82 |
| Dox 8 + Ex-64 (12.5) | 8.46 | 0.99 | 13.94 | 0.94 |
| Saline | 11.14 | — | 18.56 | — |
| Doxorubicin (8) | 8.38 | — | 13.55 | — |
| Dox (8) + Ex-64 (200) | Dead | Dead | Dead | Dead |
| Dox (8) + Ex-64 (100) | 5.03 | <0.01 | 8.27 | <0.01 |
| Dox (8) + Ex-64 (50) | 7.15 | 0.19 | 12.82 | 0.36 |
| Saline | 8.63 | — | 10.80 | — |
| Doxorubicin (8) | 4.72 | — | 7.27 | — |
| Dox (8) + Ex-72 (200) | 3.54 | 0.08 | 5.70 | 0.23 |
| Dox (8) + Ex-72 (100) | 2.73 | <0.01 | 5.06 | 0.07 |
| Dox (8) + Ex-72 (50) | 5.67 | 0.87 | 12.45 | 0.96 |
| Dox (8) + Ex-72 (25) | 4.14 | 0.32 | 7.65 | 0.63 |
| Dox (8) + Ex-72 (12.5) | 5.72 | 0.90 | 9.58 | 0.87 |

TABLE 3-continued

IN VIVO EVALUATION OF MDR-1 REVERSAL AGENTS AGAINST
THE HUMAN EPIDERMOID CARCINOMA KB/8.5 IMPLANTED SC
IN ATHYMIC 'NUDE' MICE
RELATIVE TUMOR GROWTH

| Drug Treatment[a] (Mg/Kg/Dose) | Relative[b] Tumor Growth Day 14 | Statistics[c] (p-value) | Relative Tumor Growth Day 21 | Statistics (p-value) |
|---|---|---|---|---|
| Saline | 11.14 | — | 18.56 | — |
| Doxorubicin (8) | 8.38 | — | 13.55 | — |
| Dox (8) + Ex-72 (200) | 4.56 | <0.01 | 8.13 | <0.01 |
| Dox (8) + Ex-72 (100) | 7.15 | 0.17 | 13.08 | 0.43 |
| Dox (8) + Ex-72 (50) | 5.85 | 0.02 | 10.01 | 0.04 |
| Saline | 10.03 | — | 15.78 | — |
| Doxorubicin (8) | 5.46 | — | 8.72 | — |
| Dox (8) + Ex-72 (200) | 4.28 | 0.04 | 7.48 | 0.21 |
| Dox (8) + Ex-72 (100) | 6.46 | 0.91 | 11.99 | 0.98 |
| Dox (8) + Ex-72 (50) | 5.68 | 0.68 | 9.82 | 0.78 |
| Dox (8) + Ex-72 (25) | 7.11 | 0.98 | 11.57 | 0.96 |
| Saline | 8.35 | — | 12.08 | — |
| Doxorubicin (8) | 6.69 | — | 10.17 | — |
| Dox (8) + Ex-27 (150) | Toxic | Toxic | — | |
| Dox (8) + Ex-27 (100) | 4.12 | <0.01 | 6.39 | 0.01 |
| Dox (8) + Ex-27 (50) | 5.63 | 0.18 | 9.55 | 0. |
| Dox (8) + Ex-27 (25) | 5.71 | 0.20 | 10.30 | 0.61 |
| Dox (8) + Ex-27 (12.5) | 5.68 | 0.15 | 9.66 | 0.40 |
| Saline | 8.35 | — | 12.08 | — |
| Doxorubicin (8) | 6.69 | — | 10.17 | — |
| Dox (8) + Ex-75 (200) | 4.95 | 0.02 | 7.70 | 0.04 |
| Dox (8) + Ex-75 (100) | 3.76 | <0.01 | 6.74 | 0.01 |
| Dox (8) + Ex-75 (50) | 5.60 | 0.18 | 9.12 | 0.34 |
| Dox (8) + Ex-75 (25) | 5.92 | 0.26 | 11.05 | 0.74 |
| Dox (8) + Ex-75 (12.5) | 8.10 | 0.88 | 14.21 | 0.96 |
| Saline | 6.32 | — | 9.53 | — |
| Doxorubicin (8) | 6.84 | — | 10.84 | — |
| Dox (8) + Ex-89 (200) | 2.59 | <0.01 | 6.04 | <0.01 |
| Dox (8) + Ex-89 (100) | 7. | 0.1.3 | 11.04 | 0.40 |
| Dox (8) + Ex-89 (50) | 4.50 | 0.04 | 9.40 | 0.31 |
| Dox (8) + Ex-89 (25) | 5.17 | 0.13 | 8.02 | 0.09 |
| Dox (8) + Ex-89 (12.5) | 5.47 | 0.10 | 10.70 | 0.41 |

[a]Doxorubicin was administered in a single intravenous dose, and MDR-1 reversal agents were administered subcutaneously, at −2 hours and at +2 hours relative to the Doxorubicin dose. Drugs were administered only on Day +1 post tumor staging (Day 0 of the test period).

[b]Relative tumor growth = $\frac{\text{Mean tumor mass on Day 14, 21}}{\text{Mean tumor mass on Day 0}}$

[c]Statistical analyses of Log Relative Tumor Growth, comparing treatment with Doxorubicin + MDR-1 reversal agent to treatment with an equivalent dose of Doxorubicin alone. A p-value ($p \leq 0.05$) indicates significant reduction in relative tumor growth for combination therapy groups.

Dox = Doxorubicin

These results reveal that the compound disclosed in the claims, in combination with vincristine are effective in prolonging the life of mice bearing tumors that are resistant to treatment with vincristine. In addition, the compounds disclosed in the claims, in combination with doxorubicin, are effective in reducing the tumor size of mice bearing tumors that are .resistant to treatment with doxorubicin. Both vincristine and doxorubicin are used clinically to treat MDR resistant tumors.

The active ingredients of the therapeutic compositions and the novel compound of the present invention are effective modulators of a form of multiple drug resistance, commonly exhibited by human and animal tumors, that results from over-expression of the MDR-1 gene. When administered in combination with conventional antineoplastic chemotherapy, these compounds restore drug sensitivity to multiple drug resistant animal and human tumors resulting in significant increases in life span of leukemic animals and significant reduction in growth of human solid tumors implanted into experimental mammals. A preferred dosage regimen for optimum results would be from about 25 mg to about 200 mg per kilogram of body weight per day and such dosage units are employed that a total of from about 1.75 g to about 14 g of the active compound, for a subject of about 70 kg of body weight, are administered in a 24-hour period. This dosage may be adjusted to provide the optimum therapeutic response. For example, several divided doses may be administered daily, or the total daily dose administered by slow constant infusion, or the dose may be proportionally reduced as indicated by the exigencies of the therapeutic situation. A decided practical advantage is that the active compounds may be administered by the oral, subcutaneous, intraperitoneal or intravenous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between 200 mg. and 3.5 g of active compound.

The tablets, troches, pills, capsules and the like may also contain the following: A binder such as gum tragacanth, acacia, corn starch or gelatin; excipients such as dicalcium phosphate; a disintegrating agent such as corn starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compounds may also be administered parenterally or intraperitoneally. Solutions of the active compound as a free base or pharmacologically acceptable salt can be prepared in glycerol, liquid polyethylene glycols, and mixtures thereof and in oils. Under ordinary conditions of storage and use, these preparations contain a presevative to prevent the growth of microorganisms.

The pharmaceutical forms suitable for injectable use include sterile aqueous solutions or dispersions and sterile powders for the extemporanous preparation of sterile injectable solution or dispersions. In all cases the form must be sterile and must be fluid to the extent that easy syringability exists. It must be stable under the conditions of manufacture and storage and must be preserved against the contamination action of microorganisms such as bacteria and fungi. The carrier can be a solvent or dispersion medium containing, for example, water, ethyl alcohol, polyol (for example, glycerol, propylene glycol, cremophor and liquid polyethylene glycol, and the like), suitable mixtures thereof, and vegetable oils. The proper fluidity can be maintained, for example, by the use of a coating such as lecithin, by the maintenance of the required particle size in the case of dispersion and the use of surfactants. The prevention of the action of microorganisms can be brought about by various antibacterial and antifungal agents, for example, parabens, chlorobutanol, phenol, sorbic acid, thimerosal and the like. In many cases, it Will be preferable to include isotonic agents, for example sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powder, for the preparation of sterile infectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit for as hereinbefore disclosed. A unit dosage form can, for example, contain the principal active compound in amounts ranging from about 200 mg. to about 3.5 g, with from about 500 mg. to 3.0 g being preferred. Expressed in proportions, the active compound is generally present in from about 200 mg. to about 3.5 g/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage, slow constant infusion or repeated daily dosages can be administered. The duration of treatment will depend on the chemotherapeutic agent with which the compounds of claim 1 are administered.

It is also possible to dispense one daily dosage or one dose on alternate or less frequent days. As can be seen from the dosage regimens, the amount of principal active ingredient administered is a sufficient amount to aid regression and palliation of the cancer or the like, in the absence of excessive deleterious side effects of a cytotoxic nature to the hosts harboring the cancer. As used herein cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

The following non-limiting examples illustrate the preparation of representative compounds of the invention.

EXAMPLE 1

3,4-Dimethoxy-α-[{4-methylphenyl)thio]benzeneacetonitrile

A mixture of 4.12 g of α-chloro-3,4-dimethoxybenzeneacetonitrile (U.S. Pat. No. 4,833,162), 2.48 g of p-thiocresol, 2.76 g of potassium carbonate and 100 mL of acetonitrile is stirred at 65° C. overnight. After filtering off the salts, the reaction mixture is concentrated in vacuo leaving a golden oil. The oil is dissolved in a minimum amount of ethyl acetate and diluted with 3 volumes of hexane. Seeding gives 3.81 g of the desired compound as light yellow crystals.

EXAMPLE 2

α-{3-Chloropropyl)-3,4-dimethoxy-α-[(4-methylphenyl)thio)benzeneacetonitrile

To a solution of 2.39 g of 3,4-dimethoxy-α-[(4-methylphenyl)thio]benzeneacetonitrile in 21 mL of dimethyl sulfoxide, under an argon atmosphere with stirring, is added 0.336 g of 60% sodium hydride in oil. This mixture is stirred for 1.5 hours. To the resulting solution is added 1.32 g of 1-bromo-3-chloropropane and this reaction mixture is stirred for 3 hours and is next poured into 100 mL of ice water. This mixture is twice extracted with diethyl ether and the combined organic extracts dried with magnesium sulfate. The organic solution is filtered, and concentrated in vacuo to give the desired compound as a golden oil.

EXAMPLE 3

α-(3,4-Dimethoxyphenyl)-3,4-dihydro-6,7-dimethoxy-α-[(4-methylphenyl]thio]-2(1H)-isoquinoline-pentanenitrile To a solution of 3.20 g of α-(3-chloropropyl)- 3,4-dimethoxy-α-[(4-methylphenyl)thio]benzeneacetonitrile in 30 mL of dimethyl formamide, under argon, is added 2.78 g of potassium carbonate, 79.5 mg of potassium iodide, and 1.84 g of 6,7-dimethoxy-1,2,3,4-tetrahydroisoquinoline hydrochloride. The reaction mixture is then heated at 95° C. for 4 hours, then allowed to cool and stir at ambient temperature for 12 hours. The solvent is evaporated from the mixture under vacuum at 45° C. The residue is partitioned between diethyl ether and water. The organic solution is dried with magnesium sulfate, filtered and evaporated to give the crude product. The product is chromatographed on a column of silica gel and is eluted with ethyl acetate providing 1.6 g of the desired product, after evaporation of the solvent, as an orange gum.

MS(CI): m/z 533(MH$^+$).

Calcd for $C_{31}H_{36}O_4N_2S$: C=69.32, H=6.85, N=5.22, S=5.96 Found: C=69.38, H=6.59, N=5.15, S=6.06

EXAMPLE 4

α-{3,4-Dimethoxyphenyl)-3,4-dihydro-6,7-dimethoxy-α-[(4-methylphenyl]thio]-2(1H)-isoquinoline-pentanenitrile monohydrochloride.

To a solution of 1.43 g of α-(3,4-dimethoxyphenyl)-3,4-dihydro-6,7-dimethoxy-α-[(4-methylphenyl)thio]-2(1H)-isoquinolinepentanenitrile in 40 mL of diethyl ether, with stirring, is added 0.617 mL of a 4.71M solution of hydrogen chloride in absolute ethyl alcohol. The reaction mixture is then stirred for 15 hours while sealed. The title product is then collected by filtration, washed with ether, and dried under vacuum to give 1.32 g of the desired product as pink crystals.

mp 147–150° C. (dec.).

Calcd for $C_{31}H_{37}O_4N_2SCl$: C=65.42, H=6.55, N=4.92, Cl=6.23, S=5.63 Found C=65,21, H=6,78, N=4.84, Cl=6.12, S=5.33

EXAMPLE 5

α-{3,4-Dimethoxyphenyl)-3,4-dihydro-6,7-dihydroxy-1-methyl-α-[(4-methylphenyl)thio]-2(1H)-isoquinolinepentanenitrile The procedure of Example 3 is repeated using 1.0 g of α-(3-chloropropyl)-3,4-dimethoxy-α-[(4-methylphenyl)thio]benzeneacetonitrile and 0.76 g of 1-methyl- 6,7-dihydroxy-1,2,3,4-tetrahydroisoquinoline. This affords 0.253 g of the desired product as a beige gum.

Calcd for $C_{30}H_{34}N_2O_4S$ 0.5 $H_2O$: C=68.28, H=6.69, N=5.31, S=6.07 Found: C=68.35, H=6.67, N=5.00, S=5.84

EXAMPLE 6

α-{3,4-Dimethoxyphenyl]-3,4-dihydro-6,7-dihydroxy-1-methyl-α-[(4-methylphenyl)thio]-2(1H)-isoquinoline pentanenitrile monohydrochloride The procedure of Example 4 is repeated using 0.19 g of α-(3,4-dimethoxyphenyl)-3,4-dihydro-6,7 -dihydroxy-1-methyl-α-[(4-methylphenyl)thio]-2(1H)-isoquinolinepentanenitrile. This affords 0.144 g of the desired product as a light brown solid.

mp 123–126° C.

Calcd for $C_{30}H_{35}N_2O_4SCl$ 0.75 $H_2O$: C=63.37, H=6.47, N=4.93, Cl=6.24, S=5.63 Found: C=63.68, H=6.21, N=5.00, Cl=5.80, S=5.57

EXAMPLE 7

α-(4-Chlorobutyl)-3,4-dimethoxy-α-[4-methylphenyl]-thio]benzeneacetonitrile

The procedure of Example 2 is repeated using 3.3 g of 4-dimethoxy-α-[(4-methylphenyl)thio]benzeneacetonitrile and 2.23 g of 1-chloro-4-bromobutane. This affords 3.18 g of the desired product as a colorless oil.

$^1$H NMR (CDCl$_3$) :δ 7.25(d,2H,J=8,2MePhH); 7.07 (d, 2H,J=8,2MePhH); 6.95(d,1H,J=8,ArH); 6.89(s,1H,ArH); 6.78(d,1H,J=8,ArH); 3–88(s,3H,OCH$_3$); 3.48(t,2H,CH$_2$Cl); 2.32(s,3H,CH$_3$Ph); 2.22 (m, 2H, 3-CH$_2$); 1.80(m,2H,2-CH$_2$); 1.68(m, 1H,1-CH$_2$); 1.45 (m, 1H, 1-CH$_2$) .

EXAMPLE 8

α-(3,4-Dimethoxyphenyl)-6,7-dimethoxy-α-[(4-methylphenyl)thio]-4-piperidinol-2-isoquinoline-hexanenitrile The procedure of Example 3 is repeated using 3.11 g of α-(4-chlorobutyl)-3,4-dimethoxy-α-[(4-methylphenyl)thio] benzeneacetonitrile and 1.84 g 6,7-dimethoxy-1,2,3,4-tetrahydroisoquinoline hydrochloride. This affords 1.83 g of the desired product as a brown oil.

MS(CI):m/z 547(MH$^+$).

¹H NMR (CDCl₃) :δ 7.24(d,2H,J=8,MePhH); 7.07(d,2H, J=8, MePhH); 6.96(d, 1H,J=8.4,ArH); 6.87(s,1H,ArH); 6.74(d, 1H,J=8.4,ArH); 6.58,6.50(2s,2H,IQArH); 3.84(m, 12H, OCH₃); 3.51(s,2H,IQ 1-CH₂); 2.78,2.66(2t,4H, IQ 3+4-CH₂); 2.45(t,2H,α-CH₂); 2.32(B,3H,ArCH₃); 2.26 (m,2H,d-CH₂); 1.60(m,3H,g+b-CH₂); 1.35(m, 1H,b-CH₂).

EXAMPLE 9

α-(3,4-Dimethoxyphenyl)-3,4-dihydro-6,7-dimethoxy-α-[(4-methylphenyl]thio]-2(1H)-isoquinolinebutanenitrile The procedure of Example 3 is repeated using 3.3 g of α-(2-chloroethyl)-3,4-dimethoxy-α-[(4-methylphenyl)thio] benzeneacetonitrile and 1.14 g of 6,7-dimethoxy-1,2,3,4-tetrahydroisoquinoline hydrochloride. This affords 0.311 g of the desired product as a brown oil.

MS (FAB):m/z 519 (M+H),

Calcd for C₃₀H₃₄N₂O₄S 0.5H₂O: C=68.28, H=6.99, N=5.31, S=6.80 Found C=68.56, H=6.55, N=5.21, S=5.73

EXAMPLE 10

α-(3-Chloro-2-methylpropyl)-3,4-dimethoxy-α-[(4-methylphenyl)thio]benzeneacetonitrile The procedure of Example 2 is repeated using 3.79 g of 4-dimethoxy-α-[(4-methylphenyl)-thio]benzeneacetonitrile and 3.26 g of 1-bromo-3-chloro-2-methylpropane. This affords 4.13 g of the desired product as a light yellow oil.

MS (LR): m/z 407 (M+NH₄).

¹H NMR(CDCl₃) :δ 7.24–6.74(m,7H,ArH); 3.89–3.85(m, 6H, OCH₃); 3.65–3.14(2dd,2H,CH₂Cl); 2.70–2.45(m, 1H,2-CH); 2.33(s,3H,CH₃Ph); 2.22–1.95(m,2H,1-CH₂); 1.12, 0.87(2d, 3H,CH₃) (60/40 mixture of diastereomers).

EXAMPLE 11

α-(3,4-Dimethoxyphenyl]-3,4-dihydro-6,7-dimethoxy-gamma-methyl-α-[4-methylphenyl)thio]-2(1H)-isoquinolinepentanenitrile The procedure of Example 2 is repeated using 4.0 g of α-(3-chloro-2-methylpropyl)-3,4-dimethoxy-α-[(4-methylphenyl)thio]benzeneacetonitrile and 3.5 g of 6,7-dimethoxy-1,2,3,4-tetrahydroisoquinoline hydrochloride. This affords 0.985 g of the desired product as a yellow foam.

MS(Hi res): m/z

Calcd for C₃₂H₃₈N₂O₄S ⅛H₂O 546.2553 Found 547.2625

Calcd for C₃₂H₃₈N₂O₄S ⅛H₂O: C=70.01, H=7.02, N=5.10, S=5.84 Found C=69.68, H=7.17, N=4.97, S=5.83

EXAMPLE 12

α-(3,4-Dimethoxyphenyl)-3,4-dihydro-6,7-dimethoxy-α-[(4-methylphenyl]thio]-2(1H)-isoquinolinepentanoic acid methyl ester The procedure of Example 3 is repeated using 3.0 g of α-(3-chloropropyl)-3,4-dimethoxy-α-[(4-methylphenyl)thio]benzeneacetonitrile. This affords 0.84 g of the desired product as a colorless glass.

MS(CI): m/z 565(M⁺).

Calcd for C₃₂H₃₉NO₆S: C=67.94, H=6.95, N=2.48, S=5.67 Found C=67.89, H=6.99, N=2.31, S=5.46

EXAMPLE 13

α-(11-Bromoundecyl]-3,4-dimethoxy-α-[(4-methylphenyl]thio]benzeneacetonitrile

To a solution of 2.50 g of 3,4-dimethoxy-α-[(4-methylphenyl)thio]benzeneacetonitrile in 50 mL of tetrahydrofuran, under an argon atmosphere with stirring, is added 0.367 g of 60% sodium hydride in oil. After 1.5 hours, 10.0 g of 1,11-dibromoundecane is added and stirring is continued for 43 hours. The reaction mixture is evaporated and the residue partitioned between diethyl ether and water. The organic phase is separated, washed with water, dried with magnesium sulfate, filtered and evaporated leaving an oil. The oil is purified via column chromatography, using hexane/ether (1:1) to afford 3.25 g of the desired product as a colorless oil.

MS(CI): m/z 532(MH⁺).

Calcd for C₃₂H₃₉NO₆S: C=63.15, H=7.19, N=2.63, Br=15.00, S=6.02 Found C=63.12, H=7.17, N=2.52, Br=14.77, S=6.02

EXAMPLE 14

α-(3,4-Dimethoxyphenyl)-3,4-dihydro-6,7-dimethoxy α-[(4-methylphenyl)thio]-2(1H)-isoquinoline tridecanenitrile The procedure of Example 3 is repeated using 3.14 g of α-(11-bromoundecyl)-3,4-dimethoxy-α-[(4-methylphenyl)thio]benzeneacetonitrile and 2.03 g of 6,7-dimethoxy-1,2,3,4-tetrahydroisoquinoline hydrochloride. This affords 2.2 g of the desired product as a light yellow oil.

MS(Hi res): m/z

Calcd for C₃₉H₅₂N₂O₄S 644.3648 Found 645.3730(M⁺ H).

Calcd for C₃₉H₅₂N₂O₄S ½H₂O: C=71.63, H=8.17, N=4.29, S=4.90 Found C=71.31, H=8.19, N=4.10, S=4.71

EXAMPLE 15

α-(5-Chloropentyl]-3,4-dimethoxy-α-[(4-methylphenyl)thio]benzeneacetonitrile

To a stirred solution of 5.00 g of 3,4-dimethoxy-α-[(4-methylphenyl)thio]benzeneacetonitrile in 50 mL of N,N-dimethylformamide, under an argon atmosphere, is added 0.73 g of 60% sodium hydride in oil. After 1.5 hours, 4.65 g of 1-bromo-5-chloropentane is added to the resulting solution and stirring continued for 3 hours. The reaction is poured into ice water, and twice extracted with diethyl ether. The combined organic extracts are dried (magnesium sulfate), and concentrated in vacuo to give a golden oil. Purification by chromatography on a silica gel column using diethyl ether/hexane (2:3), affords 6.07 g of the desired product as a colorless oil.

MS(CI): m/z 421(M+NH₄⁺).

Calcd for C₂₂H₂₆NO₂ClS ¹⁄₁₆H₂O: C=65.22, H=8.17, N=3.46, Cl=8.75, S=7.82 Found C=64.92, H=6.49, N=3.46, Cl=8.19, S=8.22

EXAMPLE 16

α-(3,4-Dimethoxyphenyl)-3,4-dihydro-α-[(4-methylphenyl)thio]-2(1H)-isoquinoline-2-heptanenitrile The procedure of Example 3 is repeated using 2.1 g of α-(5-chloropentyl)-3,4-dimethoxy-α-[(4-methylphenyl)thio]benzeneacetonitrile and 1.04 g of 1,2,3,4-tetrahydroisoquinoline. This affords 1.05 g of the desired product as a light brown gum.

MS(Hi res): m/z

Calcd for $C_{31}H_{36}N_2O_2S$: 500.2498 Found 501.2574(M+H).

Calcd for $C_{31}H_{36}N_2O_2S$: C=74.36, H=7.25, N=5.59, S=6.40 Found C=74.10, H=7.40, N=5.46, S=6.15

EXAMPLE 17

α-(3,4-Dimethoxyphenyl)-3,4-dihydro-6,7-dimethoxy-α-[(4-methylphenyl)thio]-2(1H)-isoquinolineheptanenitrile The procedure of Example 3 is repeated using 4.65 g of α-(5-chloropentyl)-3,4-dimethoxy-α-[(4-methylphenyl)thio]benzeneacetonitrile and 4.25 g of 6,7-dimethoxy-1,2,3,4-tetrahydroisoquinoline. This affords 3.67 g of the desired product as a light brown gum.

MS(Hi res): m/z

Calcd for $C_{33}H_{40}N_2O_4S$ $0.5H_2O$ 560.2209 Found 561.2287(M+H).

Calcd for $C_{33}H_{40}N_2O_4S$ $0.5H_2O$: C=69.77, H=7.17, N=4.58, S=5.33 Found C=69.56, H=7.25, N=4.92, S=5.63

EXAMPLE 18

α-(3,4-Dimethoxyphenyl)-3,4-dihydro-6,7-dimethoxy-α-[(4-methylphenyl]thio]-2(1H)-isoquinoline-heptanenitrile monohydrochloride The procedure of Example 4 is repeated using 0.2 g of α-(3,4-dimethoxyphenyl)-3,4-dihydro-6,7-dimethoxy-α-[(4-methylphenyl)thio]-2(1H)-isoquinolineheptanenitrile monohydrochloride The procedure of Example 4 is repeated using 0.2 g of α-(3,4-dimethoxyphenyl)-3,4-dihydro-6,7-dimethoxy-α-[(4-methylphenyl)thio]-2(1H)-isoquinolineheptanenitrile. This affords 0.184 g of the desired product as white crystals.

mp 87°–90° C.

Calcd for $C_{33}H_{40}N_2O_4S$ HCl $H_2O$: C=64.42, H=7.04, N=4.55, Cl=5.76, S=5.20 Found C=64.37, H=6.91, N=4.43, Cl=5.87, S=5.25

EXAMPLE 19

α-(5-Bromooctyl]-3,4-dimethoxy-α-[(4-methylphenyl)-thio]benzeneacetonitrile

The procedure of Example 13 is repeated using 0.869 g of 3,4-dimethoxy-α-[(4-methylphenyl)thio]benzeneacetonitrile and 1.6 mL of 1,8-dibromooctane. This affords 0.544 g of the desired product as a pale yellow oil.

MS(CI): m/z 490(MH$^+$).

$^1$H NMR(CDCl$_3$):δ 7.24(d,2H,J=8,2MePhH); 7.06(d,2H, J=8, 2MePhH); 6.95(d,1H,J=8.4,ArH); 6.88(s,1H,ArH); 6.77 (d, 1H,J=8.4,ArH); 3.88, 3.83(2s,3H,OCH$_3$); 3.39 (t, 2H, CH$_2$Br); 2.32(s,3H,CH$_3$Ph); 2.18(m,2H,7-CH$_2$); 1.82(m,2H, 6-CH$_2$); 1.55(m,1H,1-CH$_2$); 1.38(m,3H,1+5-CH$_2$); 1.27(m, H,2+3+4-CH$_2$).

EXAMPLE 20

α-(3,4-Dimethoxyphenyl)-3,4-dihydro-6,7-dimethoxy-α-[(4-methylphenyl)thio]-2(1H)-isoquinoline-decanenitrile The procedure of Example 3 is repeated using 0.836 g of α-(5-bromooctyl)-3,4-dimethoxy-α-[(4-methylphenyl)thio]benzeneacetonitrile and 0.675 g of 6,7-dimethoxy-1,2,3,4-tetrahydroisoquinoline. This affords 0.422 g of the desired product as a brown gum.

MS(Hi res): m/z

Calcd for $C_{36}H_{46}N_2O_4S$ ¼hexane 602.3179 Found 603.3254 (M+H).

Calcd for $C_{36}H_{46}N_2O_4S$ ¼hexane: C=72.14, H=7.99, N=4.49, S=5.13 Found C=72.44, H=8.13, N=4.42, S=5.53

EXAMPLE 21

α-(3,4-Dimethoxyphenyl)-7,8-dihydro-α-[(4-methylphenyl)thio]-1,3-dioxolo[4,5-g]quinoline-6(5H)-heptanenitrile The procedure of Example 3 is repeated using 0.854 g of α-(5-chloropentyl)-3,4-dimethoxy-α-[(4-methylphenyl)thio]-benzeneacetonitrile and 0.677 g of 6,7-dimethoxy-1,2,3,4-tetrahydroisoquinoline. This affords 0.701 g of the desired product.

MS(Hi res): m/z

Calcd for $C_{32}H_{36}N_2O_4S$ $2H_2O$ 544.2396 Found 545.2478 (M+H).

Calcd for $C_{32}H_{36}N_2O_4S$ $2H_2O$: C=66.18, H=6.94, N=4.83, S=5.52 Found C=66.17, H=6.92, N=4.58, S=5.36

EXAMPLE 22

α-(3,4-Diethoxyphenyl)-3,4-dihydro-6-methoxy-α-[(4-methylphenyl)thio]-2(1H)-isoquinolineheptanenitrile The procedure of Example 3 is repeated using 2.05 g of α-(5-chloropentyl)-3,4-dimethoxy-α-[(4-methylphenyl)thio]benzeneacetonitrile and 1.52 g of 6,7-dimethoxy-1,2,3,4-tetrahydroisoquinoline. This affords 1.25 g of the desired product as a brown oil.

MS(FAB): m/z 531 (M+H).

Calcd for $C_{32}H_{38}N_2O_3S$: C=72.42, H=7.22, N=5.28, S=6.04 Found C=72.17, H=7.45, N=4.94, S=5.93

EXAMPLE 23

α-(5-Iodopentyl)-3,4-dimethoxy-α-[(4-methylphenyl)-thio] benzeneacetonitrile

A mixture of 0.86 g of α-(5-chloropentyl)- 3,4-dimethoxy-α-[(4-methylphenyl)thio]benzeneacetonitrile, 3.2 g of sodium iodide, and 10 mL of acetone is heated to reflux overnight, protected from light. The volatiles are removed in vacuo and 30 mL of diethyl ether is added to the residue. The insolubles are collected and the volatiles removed in vacuo. The residue is purified via column chromatography using hexane/ethyl acetate (2:1) to afford 1.02 g of the desired product as a clear oil.

MS(CI): m/z 496(M+H).

EXAMPLE 24

α-(3,4-Dimethoxyphenyl)-1,3-dihydro-α-[(4-methylphenyl)thio]-1,3-dioxo-2H-isoindole-2-heptanenitrile A mixture of 6.12 g of α-(5-iodopentyl)-3,4-dimethoxy-α-[(4-methylphenyl)thio]benzeneacetonitrile and 2.22 g of potassium phthalimide and 50 mL of N,N-dimethylformamide is heated on a steam bath for 2 hours. The reaction solution is concentrated in vacuo and the residue is distributed between diethyl ether-water, with agitation. The organic layer is washed with 1N sodium hydroxide, followed by aqueous potassium bicarbonate. The solution is dried (sodium sulfate), and the volatiles removed in vacuo. Chromatography on silica gel, with gradient elution progressing from hexane to chloroform to methyl alcohol, affords 4.77 g of the desired product as a fluorescent oil.

MS(FAB): m/z 515 (M+H), 391 (M-TolSH).

Calcd for $C_{30}H_{30}N_2O_4S$ ⅜$H_2O$: C=69.11, H=5.95, N=5.37, S=6.14 Found C=69.34, H=5.78, N=5.23, S=5.79

$^1$H NMR(CDCl$_3$):δ 7.84(M,2H,Phth-H), 7.71(m,2H, Phth-H), 7.23(d,2H,J=8,2MePhH), 7.06(d,2H,J=8,2MePhH), 6.95,6.88,6.77(m,d,d,3H,(MeO)2ArH), 3.88,3.83(2s, 2H, 2ArOCH$_3$), 3.63(t,2H, z-CH$_2$), 1.65(m,2H,e-CH$_2$), 1.34(m, 4H,b,d-CH$_2$).

EXAMPLE 25

α-(5-Aminopentyl)-3,4-dimethoxy-α-[(4-methylphenyl)-thio]benzeneacetonitrile

A mixture of 4.72 g of α-(3,4-dimethoxyphenyl)- 1,3-dihydro-α-[(4-methylphenyl)thio]-1,3-dioxo- 2H-isoindole-2-heptanenitrile, 100 mL of ethyl alcohol, and 7.0 mL of hydrazine hydrate is heated under reflux. In about a 30 minutes, a heavy precipitate forms. After 1.33 hours, the reaction is cooled to room temperature and concentrated in vacuo. The residue is warmed on a steam bath with 2N hydrochloric acid for 10 minutes. Diatomaceous silica and chloroform are added, the mixture is shaken thoroughly and then filtered through more diatomaceous silica. The organic phase is washed first with aqueous ammonia, then brine, and, after drying (sodium sulfate), it is concentrated in vacuo to give 3.97 g of the desired product as a yellow oil.

MS(CI): m/z 385(M+H).

Calcd for $C_{22}H_{28}N_2O_2S$ ⅝$H_2O$: C=66.77, H=7.45, N=7.08, S=8.09 Found C=66.53, H=7.02, N=6.73, S=8.04

$^1$H NMR(CDCl$_3$+TFA) :δ 7.21(d,2H,J=8,2MePhH), 7.09(d,2H, J=2MePhH), 6.88(m,3H, (MeO)2ArH), 3.89, 3.84(2s,6H, 2ArOCH$_3$), 3.10(t,2H,5-CH$_2$), 2.33(s,3H,Ar-CH$_3$), 2.23(t, 2H,1-CH$_2$), 1.70(m,2H,4-CH$_2$), 1.43, (m,4H, 2,3-CH$_2$).

EXAMPLE 26

α-(3,4-Dimethoxyphenyl)-1,3-dihydro-5,6-dimethoxy-α-[(4-methylphenyl)thio]-2H-isoindole-2-heptanenitrile To a solution of 3.03 g of α-(5-aminopentyl)- 3,4-dimethoxy-α-[(4-methylphenyl)thio]benzeneacetonitrile, 1.85 g of 1,2-bis(chloromethyl)-3,4-dimethoxybenzene, 20 mL of toluene, and 0.22 g of tetrabutylammonium chloride, is added water containing 2 g of sodium hydroxide. The mixture is stirred for 48 hours. Upon adjusting the pH of the aqueous layer to pH 9 with solid sodium bicarbonate, the layers are separated and the aqueous layer further extracted with chloroform. After drying the combined organic extracts over sodium sulfate, they are passed through a pad of hydrous magnesium silicate, and concentrated in vacuo to a brown gum. This gum is purified by HPLC using a reverse phase C-18 radial-pak column (6 cm.×30 cm.) with a buffered solvent system (150 mL ammonium hydroxide in water adjusted to a pH 4.00 with acetic acid, then diluted to 7,875 mL with water; 5700 mL of acetonitrile and 1425 mL of methyl alcohol are added). After solvent removal, 0.85 g of the desired product is obtained as a yellow oil.

MS(Hi res): m/z

Calcd for $C_{32}H_{38}N_2O_2S$ 546.2553 Found 546.2569

Calcd for $C_{32}H_{38}N_2O_2S$: C=70.30, H=7.01, N=5.12, S=5.86 Found C=70.02, H=4.79, N=4.79, S=5.62

EXAMPLE 27

α-[3,4-Dimethoxyphenyl)-1,3-dihydro-5,6-dimethoxy-α-[(4-methylphenyl)thio]-2H-isoindole-2-heptanenitrile hydrochloride Nitrogen is bubbled through a stirred solution of 16.63 g of α-(5-aminopentyl)-3,4-dimethoxy-α[(4-methylphenyl)thio]benzeneacetonitrile, 10.12 g of 1,2-bischloromethyl-3,4-dimethoxybenzene (prepared by the procedure of J. H. Wood et. al., J.Am. Chem. Soc., 72, 2989(1950)), and 2.5 g of tetrabutylammonium chloride in 250 ml of toluene. A solution of 28 g of sodium hydroxide in 84 ml of water is added and the mixture is stirred vigorously for 48 hours. The layers are separated and the organic phase is washed with saturated sodium chloride, dried and concentrated in vacuo. The residue is purified by chromatography (silica gel: 50% ethyl acetate/hexane; ethyl acetate; 1,2,3 and 4% methyl alcohol/ethyl acetate; methyl alcohol) to give 14.85 g of a brown gum. The gum is dissolved in 30 ml of ethyl alcohol and 7 ml of 4.5M ethanolic hydrogen chloride is added. The solution is cooled to 0° C. and seeded. The crystals are collected to give 11.19 g of crude product, mp 103–114° C. The crystals are recrystallized 2 times: first at a ratio of 1 g/4 ml of ethyl alcohol, second at a ratio of 1g/5 ml of ethyl alcohol to give 9.38 g of the desired product as gray crystals.

mp 121°–125° C.

$^1$H NMR(CDCl$_3$):δ 7.20(d,2H,J=3,MePh-H); 7.08(d,2H, J=3, MePh-H); 6.96(m,3H, (MeO)$_2$ArH); 6.8(m,2H, isoindole Ph-H); 4.93 (br, 2H, isoindole-CH$_2$), 4.12 (br, 2H, isoindole-CH$_2$); 3.87(m,12H, (OCH$_3$)$_4$), 3.15(br,2H,φ-CH$_2$); 2.32(s,3H, PhCH$_3$); 2.22(br,2H,β-CH$_2$); 1.97(br,2H, χ-CH$_2$); 1.55(m,2H,ε-CH$_2$); 1.42(m,2H,δ-CH$_2$).

MS(FAB): m/z

Calcd for $C_{32}H_{38}N_2O_4S$ 547. 2630 Found 547.2630

Calcd for $C_{32}H_{38}N_2O_4S$ HCl $H_2O$: C=63.93, H=6.87, N=4.66, Cl=5.90, S=5.33 Found C=64.22, H=6.57, N=4.59, Cl=5.74, S=5.39

EXAMPLE 28

7-[[(1,1-Dimethylethyl]dimethylsilyl]oxy]-1,2,3,4-tetrahydro-6-methoxyisoquinoline To a solution of 19.2 g of 6-hydroxy-7-methoxy- 1,2,3, 4-tetrahydroisoquinoline in 425 mL of pyridine is added 48.4 g of t-butyl-dimethylsilylchloride and 0.5 g of 4-N,N-dimethylaminopyridine. The solution is heated to reflux for 3.5 hours and the volatiles removed at 70° C. by distillation. The residue is partitioned between aqueous potassium bicarbonate and ethyl acetate. The organic layer is washed with water, dried (magnesium sulfate) and the volatiles removed in vacuo. The residue is suspended in diethyl ether, filtered and washed with hexane. The filtrate is evaporated and the residue distilled via Kugelrohr at 150 mm and 120°–130° C. to afford 26.2 g of the desired product as a colorless oil.

MS(CI): m/z 294 (MH+).

Calcd for $C_{16}H_{27}NO_2Si$ ¼$H_2O$:

C=64.49, H=9.31, N=4.70, Si=9.43 Found C=64.46, H=9.03, N=4.70, Si=9.52

EXAMPLE 29

α-(3,4-Dimethoxyphenyl)-7-[[(1,1-dimethylethyl)-dimethylsilyl]oxy]-3,4-dihydro-6-methoxy-α-[(4-methylphenyl)thio]-2(1H)-isoquinolineheptanenitrile The procedure of Example 3 is repeated using 2.5 g of α-(5-chloropentyl-3,4-dimethoxy-α-[(4-methylphenyl)thio] benzeneacetonitrile and 2.54 g 7-[[(1,1-dimethylethyl)dimethylsilyl]oxy]-1,2,3,4-tetrahydro- 6-methoxyisoquinoline. This affords 1.2 g of the desired product as a light yellow oil.

MS(CI): m/z 661.(MH+).

Calcd for $C_{38}H_{52}N_2O_4SSi$ ¼$H_2O$: C=68.59, H=7.95, N=4.21, S=4.81, Si=4.22 Found C=68.73, H=7.69, N=3.99, S=4.36, Si=3.78

EXAMPLE 30

α-(3,4-Dimethoxyphenyl)-3,4-dihydro-7-hydroxy-6-methoxy-α-[(4-methylphenyl)thio]-2(1H)-isoquinolineheptanenitrile To a solution of 1.0 g of α-(3,4-dimethoxyphenyl)-7-[[(1,1-dimethylethyl)dimethylsilyl]oxy]-3,4-dihydro- 6-methoxy-α-[(4-methylphenyl)thio]-2(1H) isoquinolineheptanenitrile in 30 mL of tetrahydrofuran is added 3.02 mL of a 1.0M solution of tetrabutylammonium fluoride in tetrahydrofuran. This is sealed and stirred for 5 hours. The reaction mixture is evaporated and the residue taken up in ethyl acetate. The solution is washed three times with water, and the organic phase is separated and evaporated. The gum remaining is redissolved in chloroform and the solution evaporated in vacuo at 66° C. This process is repeated twice more affording 0.83 g of the desired product as a brown gum.

MS(CI): m/z 547 (MH+).

Calcd for $C_{32}H_{38}N_2O_4S$ ½$H_2O$: C=69.17, H=7.07, N=5.04, S=5.76 Found C=69.25, H=6.88, N=5.10, S=5.66

EXAMPLE 31

α-(3,4-Dimethoxyphenyl]-7-[2-(dimethylamino)-ethoxy]-3,4-dihydro-6-methoxy-α-[[4-methylphenyl)thio]-2(1H)-isoquinolineheptanenitrile To a solution of 0.583 g of α-(3,4-dimethoxyphenyl)- 3,4-dihydro-7-hydroxy-6-methoxy-α-[(4-methylphenyl)thio]-2(1H)-isoquinolineheptanenitrile in 20 mL of N,N-dimethylformamide is added 0.051 g of 60% sodium hydride in oil and the solution stirred for 1 hour. To this solution is added 0.34 g of freshly prepared 2-dimethylaminoethylchloride and 0.60 g of potassium iodide. The solution is stirred at room temperature for 18 hours and then the volatiles are removed at reduced pressure. The residue is dissolved in a minimum amount of ethyl acetate and 5 volumes of diethyl ether is added. This solution is passed through a short pad of hydrous magnesium silicate and the volatiles are removed at reduced pressure. The residue is chromatographed on silica gel using a gradient of diethyl ether to ethyl acetate to methyl alcohol. This afford 0.14 g of the desired product as a clear glass.

MS(Hi res): m/z

Calcd for $C_{36}H_{47}N_3O_4S$ 617.3287 Found 617.3302

EXAMPLE 32

7-(2-Chloroethoxy)-α-(3,4-dimethoxyphenyl)-3,4-dihydro 6-methoxy-α-[(4-methylphenyl]-thio]-2(1H)-isoquinoline heptanenitrile A 0.93 g portion of α-(3,4-dimethoxyphenyl)- 3,4-dihydro-7-hydroxy-6-methoxy-α-[(4-methylphenylthio]-2(1H)-isoquinolineheptanenitrile is dissolved in 25 mL of 2-butanone and 1.20 g of 2-chloroethyltosylate is added. Next, 0.72 g of potassium carbonate is added followed by 1.7 mL of 1N sodium hydroxide solution. This mixture is heated to reflux, for 6 hour with stirring, and then at ambient temperature for 16 hours. The solvent is evaporated at 50° C. in vacuo and the residue partitioned between diethyl ether and water. The organic phase is washed twice with water, dried with magnesium sulfate, filtered, and evaporated in vacuo to give an oil. The residue is chromatographed on a column of silica gel and eluted with ethyl acetate to afford 0.43 g of the desired product as a colorless gum.

MS(Hi res): m/z

Calcd for $C_{34}H_{41}N_2O_4ClS$ 608.2476 Found 608.2483

Calcd for $C_{34}H_{41}N_2O_4ClS$: C=67.03, H=6.78, N=4.60, Cl=5.82, S=5.26 Found C=66.96, H=6.87, N=4.55, Cl=5.56, S=5.09

EXAMPLE 33

α-(3,4-Dimethoxyphenyl)-3,4,dihydro-7-[2-(1H-imidazol-1-yl)ethoxy]-6-methoxy-α-[(4-methylphenyl]thio]-2(1H)-isoquinolineheptanenitrile To a solution of 0.061 g of imidazole in 5.0 mL of N,N-dimethylformamide, with stirring under argon, is added 36.0 mg of 60% sodium hydride in oil. After 45 min., a solution of 0,366 g of 7-(2-chloroethoxy)-α-( 3,4-dimethoxyphenyl)-3,4-dihydro-6-methoxy-α-[(4-methylphenylthio]-2(1H)-isoquinolineheptanenitrile in 7.0 mL of N,N-dimethylformamide is added. The resultant solution is stirred for 2 days at ambient temperature. The volatiles are removed at 55° C. in vacuo, and the residue is partitioned between chloroform and water. The organic phase is washed again with water, dried with magnesium sulfate, filtered, and evaporated producing an oil. The oil is chromatographed on a column of silica gel and eluted with chloroform/methyl alcohol (98:2). This affords of 0.144 g of the desired product as a colorless oil.

MS(Hi res): m/z

Calcd for $C_{37}H_{46}N_4O_5S$ 640.3083 Found 640.3144

EXAMPLE 34

α-(3,4-Dimethoxyphenyl)-3,4-dihydro-7-[2-(1H-imidazol-1-yl)ethoxy]-6-methoxy-α-[(4-methylphenyl)thio]-2(1H)-isoquinolineheptanenitrile hydrochloride To a solution of 0.8 g of α-(3,4-dimethoxyphenyl)- 3,4-dihydro-7-[2-(1H-imidazol-1-yl)ethoxy]-6-methoxy-α-[(4-methylphenyl)thio]-2(1H)-isoquinolineheptanenitrile in 100 mL of diethyl ether and 5 mL of ethyl alcohol is added 0.83 mL of 4.5M hydrochloric acid in ethyl alcohol. The solution is stirred for 20 minutes and the white precipitate is collected and washed three times with small portions of diethyl ether. The solid is dried in vacuo affording 0.84 g of the desired product as a white solid.

mp 70° C. (dec).

Calcd for $C_{37}H_{49.75}N_4O_6SCl_{1.75}$: C=60.00, H=6.77, N=7.57, Cl=8.38, S=4.32 Found C=60.10, H=6.86, N=7.21, Cl=8.78, S=4.28

EXAMPLE 35

α-(3,4-Dimethoxyphenyl)-3,4-dihydro-6,7-dimethoxy-α-[(4-methylphenyl)thio]-2(1H)-isoquinolineheptanenitrile monohydrochloride The procedure of Example 4 is repeated using 1.77 g of α-(3,4-dimethoxyphenyl)-3,4-dihydro-6,7-dimethoxy-α-[(4-methylphenyl)thio]-2(1H)-isoquinolinehexanenitrile. This affords 2.4 g of the desired product as a cream colored solid.

mp 114°–117° C.

MS(CI): m/z 546(M-HCl).

Calcd for $C_{32}H_{39}N_2O_4Cl$: C=65.91, H=6.74, N=4.80, Cl=6.08, S=5.50 Found C=65.66, H=6.90, N=4.60, Cl=5.90, S=5.43

EXAMPLE 36

α-(5-Chlorohexyl)-3,4-dimethoxy-α-[(4-methylphenyl)thio]benzeneacetonitrile

The procedure of Example 15 is repeated using 3.8 g of 3,4-dimethoxy-α-[(4-methylphenyl)thio]benzeneacetonitrile and 2.66 g of 1-bromo-5-chlorohexane. This affords 4.35 g of the desired product as a colorless oil.

MS(CI): m/z 435(M+NH$_4$).

Calcd for $C_{23}H_{28}NO_2ClS$ ⅛H$_2$O: C=65.74, H=6.78, N=3.33, Cl=8.44, S=7.62 Found C=65.61, H=6.60, N=3.19, Cl=8.18, S=8.02

EXAMPLE 37

α-(3,4-Dimethoxyphenyl)-3,4-dihydro-6,7-dimethoxy-α-[(4-methylphenyl)thio]-2(1H)-isoquinoline-octanenitrile The procedure of Example 3 is repeated using 4.3 g of α-(5-chlorohexyl)-3,4-dimethoxy-α-[(4-methylphenyl)thio]benzeneacetonitrile and 4.25 g of 6,7-dimethoxy-1,2,3,4-tetrahydroisoquinoline hydrochloride. This affords 3.05 g of the desired product as a golden gum.

MS(CI): m/z 575.

Calcd for $C_{34}H_{42}N_2O_4S$ ⅛H$_2$O: C=70.77, H=7.38, N=4.86, S=5.56 Found C=70.38, H=7.59, N=4.69, S=5.33

EXAMPLE 38

4-[4-Chloro-1-[(4-methylphenyl)thio]butyl]-1,2-dimethoxybenzene

To a solution of 13.72 g of 1,2-dimethoxy-4-[(4-methylphenyl)thio]methyl]benzene and a crystal of phenanthroline in 250 mL of tetrahydrofuran (dried over 3A sieves), under nitrogen at –78° C. is added 21.0 mL of 2.5M n-butyl lithium/hexane via a syringe. After 0 minutes, the brown solution is warmed to 0° C. for 1 hour, then it is recooled to –78° C. and 8.02 mL of 1-bromo- 3-chloropropane is added via syringe. The reaction is permitted to warm to room temperature overnight. To the now light yellow reaction mixture is added 10 mL of ethyl acetate and the resulting solution concentrated in vacuo. The residue is partitioned between ethyl acetate and water, the organic phase dried (sodium sulfate) and concentrated in vacuo to a yellow oil. Purification by chromatography on silica gel with gradient elution progressing from hexane to chloroform to methyl alcohol, repeated three times, affords 16.47 g of the desired product as a yellow oil.

MS(CI): m/z 227 and 229(MH+(-TolSH)).

Calcd for $C_{19}H_{23}ClO_2S$ ⅛H$_2$O: C=63.80, H=6.59, Cl=11.15, S=8.95 Found C=63.68, H=6.44, Cl=10.89, S=8.98

$^1$H NMR(CdCl$_3$):δ 7.15(d,2H,J=S,2MePhH); 7.02(d,2H, J=8,2 MePhH); 6.72(m,3H,ArH); 4.01(t,1H,1-CH); 3.86(s, 3H, ArOCH$_3$); 3.82(s,3H,ArOCH$_3$); 3.49(t,2H,CH$_2$—Cl); 2.29 (s,3H,Ar-CH$_3$); 2.05(m,2H,2-CH$_2$); 1.82(m,2H,3-CH$_2$).

EXAMPLE 39

2-[4-(3,4-Dimethoxyphenyl)-4-[(4-methylphenyl)thio]-butyl]-1,2,3,4-tetrahydro-6,7-dimethoxyisoquinoline To 4.6 g of 6,7-dimethoxy-1,2,3,4-tetrahydroisoquinoline in 50 mL of 2-pyrrolidinone is added 1.4 g of potassium carbonate, 0.1 g of potassium iodide and 3.51 g of 4-[4-chloro-1-[(4-methylphenyl)thio]butyl]-1,2-dimethoxybenzene. The mixture is stirred and heated at 95° C. for 24 hours and then is poured into 400 mL of water and extracted with six 60 mL portions of chloroform. The combined extracts are washed with brine, dried (sodium sulfate) and concentrated under high vacuum to give 8.85 g of brown oil. Chromatography on silica gel with gradient elution progressing from hexane to chloroform to methyl alcohol, repeated four times, affords 0.61 g of the desired product as a yellow oil.

MS(Hi res):m/z

Calcd for $C_{30}H_{37}NO_4S$ 507.2527 Found 508.2527(M+H).

Calcd for $C_{30}H_{37}NO_4S$: C=70.36, H=7.38, N=2.74, S=6.25 Found C=70.45, H=7.46, N=2.86, S=6.20

EXAMPLE 40

4-[6-Bromo-1-[(4-methylphenyl)thio]hexyl]-1,2-dimethoxybenzene

A solution of 13.72 g of 1,2-dimethoxy-4-[[(4-methylphenyl)thio]methyl]benzene in 200 mL of tetrahydrofuran (dried over 3A sieves), under nitrogen, is cooled to –78° C. and 30 mL of 1.7M t-butyl lithium is added. After 30 minutes, the solution is transferred, via a canula, into a stirred solution of 14.0 mL of 1,5-dibromopentane in 25 ml of tetrahydrofuran, under nitrogen at –78° C. The reaction is slowly warmed to room temperature, and the reaction is quenched by the addition of 4 mL of acetone. The reaction is concentrated in vacuo and the residual material is dissolved in ethyl acetate and is washed with brine. Drying (sodium sulfate) and solvent removal affords 33.22 g of oil. The residue is purified via chromatography on silica gel with gradient elution progressing from hexane to chloroform to methyl alcohol to afford 10.82 g of the desired product as a tan gum.

MS(FAB): m/z 299 (M-TolSH).

EXAMPLE 41

2-[6-(3,4-Dimethoxyphenyl)-6-[(4-methylphenol)thio]-hexyl]-1,2,3,4-tetrahydro-6,7-dimethoxyisoquinoline The procedure of Example 39 is repeated using 2.12 g of 4-[6-Bromo-1-[(4-methylphenyl)thio]hexyl]-1,2-dimethoxybenzene and 2.3 g of 6,7-dimethoxy- 1,2,3,4-tetrahydroisoquinoline hydrochloride. This affords 1.6 g of the desired product as a light yellow oil.

MS(Hi res): m/z

Calcd for $C_{32}H_{41}NO_4S$ 535.2756 Found 536.2834(M+H).

Calcd for $C_{32}H_{41}NO_4S$: C=70.13, H=7.83, N=3.07, S=5.62 Found C=70.15, H=7.51, N=2.79, S=5.25

EXAMPLE 42

3-[2-Cyano-2-(3,4-dimethoxyphenyl)-2-[(4-methylphenyl)thio]ethyl]benzoic acid

To a cold (−78° C.) solution of 1.86 g of 3,4-dimethoxy-α-[(4-methylphenyl)thio]benzene acetonitrile in 15 mL of tetrahydrofuran is added drop-wise a solution of 2.9 mL of n-butyl lithium (2.2 M) in hexane. This solution is stirred at −78° C. for 35 minutes. A solution of 0.67 g of m-carboxybenzyl bromide in 51mL of anhydrous tetrahydrofuran is added drop-wise, stirred at −78° C. for 40 minutes and then at room temperature for 15 minutes. The mixture is quenched with water and extracted with ethyl acetate. The ethyl acetate extract is washed with brine, dried and filtered. The filtrate is evaporated in vacuo to yield a yellow oil. This oil is purified by flash chromatography using methylene chloride/methyl alcohol (95:5) to yield 1.15 g of the desired product as a yellow foam.

$^1$H NMR(CDCl$_3$) :δ 7.95(d,1H,Ar); 7.73(s,1H,Ar); 7.36–7.2 (m,2H,Ar); 7.1(d,2H,Ar); 6.98–6.92(m,2H,Ar); 6.75(d,1H, Ar); 3.87(s,3H,OCH$_3$); 3.83(s,3H,OCH$_3$); 3.49(s,2H); 2.34(s,3HCH$_3$).

EXAMPLE 43

α-3,4-Dimethoxyphenyl)3-(hydroxymethyl)-α-[(4-methylphenyl)thio]benzene propane nitrile A mixture of 1.0 g of 3-[2-cyano-2-(3,4-dimethoxyphenyl)- 2-[(4-methylphenyl)thio]ethyl]benzoic acid and 0.7 mL of borane methyl sulfide complex (10M) in 5 mL of tetrahydrofuran is stirred at room temperature for 18 hours. The mixture is quenched with methyl alcohol, treated with hydrogen chloride gas, stirred and the solvent is evaporated to yield a white foam. The foam is dissolved in water, basified with 5N sodium hydroxide and extracted with ethyl acetate. The ethyl acetate extract is washed with brine, dried and filtered. The filtrate is evaporated in vacuo to yield a yellow oil. This oil is purified by flash chromatography using 2% methyl alcohol in methylene chloride to yield 0.55 g of the desired product as a colorless oil.

Calcd for $C_{25}H_{25}NSO_3$: C=71.57, H=6.01, N=3.34, Cl=7.64 Found C=71.25, H=6.01, N=3.26, Cl=7.50

EXAMPLE 44

3-(Chloromethyl)-α-(dimethoxyphenyl)-α-[(4-methylphenyl)thio]benzene propane nitrile A mixture of 0.1 mL of thionyl chloride and 0.12 mL of N,N-dimethyl formamide is stirred at room temperature for 30 minutes. A solution of 0.34 g of α-(3,4-dimethoxyphenyl)-3-(hydroxymethyl)-α-[(4-methylphenyl)thio]benzene propane nitrile in 1.0 mL of N,N-dimethylformamide is added to the above mixture and the resulting mixture is heated at 70° C. for 17 hours, cooled, poured into water and extracted with diethyl ether. The diethyl ether extract is washed with brine, dried and filtered. The filtrate is evaporated in vacuo to yield an oil. This oil is purified by flash chromatography using 10% ethyl acetate in hexane to yield 0.27 g of the desired product as a colorless oil.

Calcd for $C_{25}H_{24}NSClO_2$: C=68.56, H=5.52, N=3.20, Cl=8.09, S=7.32 Found C=68.33, H=5.50, N=3.16, Cl=8.18, S=7.32

EXAMPLE 45

3-(3,4-Dihydro-6,7-dimethoxy-2(1H)-isoquinolinyl]-α-(3,4-dimethoxyphenyl)-α-[(4-methylphenyl)thio]-benzenepropanenitrile A mixture of 0.21 g of 3-(chloromethyl)-α- 3,4-dimethoxyphenyl)-α-[(4-methylphenyl)thio]benzene propane nitrile, 0.091 g of 6,7-dimethoxy-1,2,3,4-tetrahydroisoquinoline and 0.3 g of anhydrous potassium carbonate in 2.0 mL of N,N-dimethylformamide is heated at 85° C. for 4 hours, cooled, poured into water and extracted with ethyl acetate. The ethyl acetate extract is washed with brine, dried and filtered. The filtrate is evaporated in vacuo to yield an oil. This oil is purified by flash chromatography with 1.5% methyl alcohol in chloroform to yield 0.18 g of the desired product as a yellow glassy solid.

MS(FAB): m/z 595 (M+H).

$^1$H NMR(CDCl$_3$) :δ 7.35–6.88(m,10H,Ar); 6.73–6.70(d, 1H, Ar); 6.58(s,1H,Ar); 3.86–3.79(m,12H,4-OCH$_3$); 3.58–3.50 (2s,4H); 3.3(s,2H); 2.78–2.55(2m,4H); 2.32(s, 3H,CH$_3$).

EXAMPLE 46

2-[6-(3,4-Dimethoxyphenyl]-6-[(4-methylphenyl]-thio]hexyl]-1,2,3,4-tetrahydro-6-methoxyisoquinoline To a solution of 4.23 g of 4-[6-bromo-1-[(4-methylphenyl)thio]hexyl]-1,2-dimethoxybenzene in 40 mL of acetonitrile is added 3.88 g of 6-methoxy-1,2,3,4-tetrahydroisoquinoline, 1.74 mL of diisopropylethylamine and 0.01 g of sodium iodide. The solution is heated to reflux for 43 hours and cooled to room temperature. The reaction mixture is partitioned between chloroform and aqueous potassium carbonate and the organic layer is dried over magnesium sulfate. The volatiles are removed at reduced pressure and the residue chromatographed on silica gel using a gradient elution of hexane to chloroform to methyl alcohol. The residue from the chromatography is dissolved in diethyl ether and passed through diatomaceous earth. This affords 4.4 g of the desired product as a yellow oil.

MS(FAB): m/z 506 (M+H) .

Calcd for $C_{31}H_{39}NO_3S$: C=73.62, H=7.77, N=2.77, S=6.34 Found C=73.37, H=7.88, N=2.70, S=6.13

EXAMPLE 47

6-[6-(3,4,Dimethoxyphenyl)-6-[(4-methylphenyl]-thio]hexyl]-5,6,7,8-tetrahydro-1,3-dioxolo[4,5-g]-isoquinoline The procedure of Example 46 is repeated using 3.67 g of 4-[6-bromo-1-[(4-methylphenyl)thio]hexyl]- 1,2-dimethoxybenzene in 40 mL of acetonitrile and 2.65 g of 6,7-methylenedioxy-1,2,3,4-tetrahydroisoquinoline. This affords 4.13 g of the desired product as a yellow gum.

MS(CI): m/z 520(M+H$^+$).

Calcd for $C_{31}H_{37}NO_4S$ ⅞$H_2O$: C=69.53, H=7.15, N=2.57, S=5.84 Found C=69.54, H=7.30, N=2.62, S=5.98

EXAMPLE 48

4-[6-Bromo-1-[(4-methylphenyl)thio]heptyl]-1,2-dimethoxybenzene

The procedure of Example 40 is repeated using 4.0 g of 1,2-dimethoxy-4-[[(4-methylphenyl)thio]methyl]benzene and 46.15 g of 1,6 dibromohexane. This affords 36 g of the desired product as a yellow oil contaminated with 24.8% of the starting material, 1,2-dimethoxy-4-[[(4-methylphenyl)thio]methyl]benzene.

EXAMPLE 49

2-[7-(3,4-Dimethoxyphenyl)-7-[(4-methylphenyl)thio]-heptyl]-2,3-dihydro-5,6-dimethoxy-1H-isoindole A mixture of 1.79 g of 4-[6-bromo-1-[(4-methylphenyl)thio]heptyl]-1,2-dimethoxybenzene, 3.29 g of 5,6-dimethoxyisoindoline, 25 mL of acetonitrile, and 1.74 mL of N,N-diisopropylethylamine is heated under reflux for 2 days. The reaction is concentrated in vacuo and the black residue partitioned between chloroform and aqueous ammonia. The organic layer is dried (sodium sulfate) and the solvent removed at reduced pressure. Chromatography on silica gel with gradient elution progressing from hexane to chloroform to methyl alcohol, twice, gives 1.34 g of the desired product as a brown gum.

MS(Hi res): m/z

Calcd for $C_{32}H_{41}NO_4S$ 535.2756 Found 535.2723

Calcd for $C_{32}H_{41}NO_4S$ $H_2O$ C=69.41, H=7.83, N=2.53, S=5.78 Found C=69.59, H=7.51, N=2.53, S=6.19

EXAMPLE 50

2-[7-(3,4-Dimethoxyphenyl)-7-[(4-methylphenyl)thio]-heptyl]-1,2,3,4-tetrahydro-6,7-dimethoxyisoquinoline The procedure of Example 49 is repeated using 5.22 g of 4-[6-bromo-1-[(4-methylphenyl)thio]heptyl]-1,2-dimethoxybenzene, 3.29 g of 6,7-dimethoxy-1,2,3,4-tetrahydroisoquinoline hydrochloride. This affords 2.49 g of the desired product as a yellow gum.

MS(HI res): m/z

Calcd for $C_{33}H_{43}NO_4S$ 549.29126 Found 549.291

Calcd for $C_{33}H_{43}NO_4S$ $H_2O$ C=69.81, H=7.99, N=2.47, S=5.64 Found C=70.19, H=7.83, N=2.41, S=5.70

EXAMPLE 51

6,7-Bis [[(1,1-dimethylethyl)dimethylsilyl]oxy]-1,2,3,4-tetrahydroisoquinoline

A mixture of 1.0 g of 1,2,3,4-tetrahydro-6,7-isoquinolinediol hydrobromide and 2.45 g of t-butyl dimethylsilyl chloride in 25.0 mL of pyridine is heated under reflux for 4.5 hours, cooled, poured into water and extracted with diethyl ether. The diethyl ether extract is washed with brine, dried, filtered. The filtrate is evaporated to yield a brown oil. This oil is purified by Kugelrohr distillation to yield 1.6 g of the desired product as a yellow solid, b.p. 155° C., 350 torr.

EXAMPLE 52

6,7-Bis[[(1,1-dimethylethyl]dimethylsilyl]oxy]-2-[7-(3,4-dimethoxyphenyl)-7-[(4-methylphenyl)thio]heptyl]-1,2,3,4-tetrahydroisoquinoline The procedure of Example 49 is repeated with 1.24 g of 6,7-bis[[(1,1-dimethylethyl)dimethylsilyl]oxy]-1,2,3,4-tetrahydroisoquinoline and 1.83 g of 1-bromo-7-(3,4-dimethoxyphenyl)-7-[(4-dimethoxyphenyl)thio]heptane. This affords 2.0 g of the desired product as an orange oil.

Calcd for $C_{43}H_{67}NSSi_2O_4$ 0.2M $CH_2Cl_2$: C=67.63, H=8.86, N=1.83, Cl=1.85, S=4.18 Found C=67.17, H=8.97, N=1.81, Cl=1.86, S=4.23

$^1$H NMR(CDCl$_3$):δ 7.15–7.12(d,2H,Ar); 7.02–6.99 (d, 2H, Ar); 6.72(s,2H,Ar); 6.53(s,1H,Ar); 6.45(s,1H,Ar); 4.0(t, 1H); 3.85(s,3H,OCH$_3$); 3.81(s,3H,OCH$_3$); 3.45(s, 2H); 2.75(t,2H); 2.45–2.37(m,2H); 2.2e(s,3H,CH$_3$); 1.9–1.2(m, 10H); 0.96(s,18H,CH$_3$); 0.15(s,12H,CH$_3$).

EXAMPLE 53

Diethyl-6-[7-(3,4-dimethoxyphenyl)-7-[(4-methylphenyl)thio]heptyl]-5,6,7,8-tetrahydro-1,3-dioxolo-[4,5-g]-isoquinoline dicarboxylate A mixture of 1.95 g of 6,7-bis[[(1,1-dimethylethyl)dimethylsilyl]oxy]-2-[7-(3,4-dimethoxyphenyl)-7-[(4-merylphenyl)thio]heptyl]-1,2,3,4-tetrahydroisoquinoline and 10.0 mL of 1M tetrabutyl ammonium fluoride in 25 mL of tetrahydrofuran is stirred at room temperature for 2.5 hours, poured into water and extracted with ethyl acetate. The ethyl acetate extract is washed with brine, dried, filtered and filtrate is evaporated to yield 1.8 g of brownish-black oil. The oil is taken up in 60 mL of acetone, 1.8 g of anhydrous potassium carbonate is added, followed by the addition of 0.83 g of diethyl dibromomalonate. The resulting mixture is stirred at room temperature for 5 hours, filtered and the filtrate is evaporated in vacuo to yield a brown oil. This oil is purified by flash chromatography with 2% methyl alcohol in chloroform to yield 0.42 g of as a brown oil.

MS(FAB): m/z 678 (M+H).

Calcd for $C_{38}H_{47}NSO_8$ 0.3M $CH_2Cl_2$: C=65.40, H=6.82, N=1.99, Cl=3.02, S=4.56 Found C=65.23, H=6.73, N=1.93, Cl=2.66, S=4.55

EXAMPLE 54

6-[7-(3,4-Dimethoxyphenyl)-7-[(4-methylphenyl)thio]-heptyl]-5,6,7,8-tetrahydro-1,3-dioxolo[4,5-g]isoquinoline-2,2-dimethanol A mixture of 0.31 g of diethyl-6-[7-(3,4-dimethoxyphenyl)- 7-[(4-methylphenyl)thio]heptyl]-5,6,7,8-tetrahydro-1,3-dioxolo [4,5-g]isoquinoline dicarboxylate and 0.045 g of lithium borohydride in 20 mL of tetrahydrofuran is stirred at room temperature for 3 hours, poured into water and the solvent evaporated in vacuo. The resulting mixture is extracted with methylene chloride. The methylene chloride extract is dried, filtered and the filtrate is evaporated in vacuo to yield a yellow oil. This oil is purified by flash chromatography using 2% methyl alcohol in methylene chloride to yield 0.1 g of the desired product as a white foam.

Calcd for $C_{34}H_{43}NSO_6$ 1.0M $H_2O$: C=66.75, H=7.41, N=2.29, S=5.24 Found C=67.03, H=7.66, N=2.12, S=5.20

EXAMPLE 55

α-(3,4-Dimethoxyphenyl]-1-[(3,4-dimethoxyphenyl)-methyl]-3,4-dihydro-6,7-dimethoxy-α-[(4-methylphenyl)thio]-2(1H)-isoquinolineheptanenitrile The procedure of Example 49 is repeated using 0.345 g of tetrahydropapaverine hydrochloride and 0.30 g of α-(5-iodopentyl)-3,4-dimethoxy-α-[(4-methylphenyl)thio]benzeneacetonitrile. This affords 0.263 g of the desired product as a yellow oil.

MS(Hi res): m/z

Calcd for $C_{42}H_{50}N_2SO_6$ 711.34678 Found 711.3453

EXAMPLE 56

Ethyl 3,4-dimethoxy-E-oxo-benzenehexanoate

To a cold (0°–5° C.) solution of 1.52 g of veratrole in 15 mL of methylene chloride is added 2.66 g of anhydrous aluminum chloride in portions so as to maintain the temperature at 0° C. Then a solution of 1.93 g of adipic acid chloride, monoethylester in 10 mL of methylene chloride is added drop-wise. The resulting mixture is stirred at 0° C. for 4 hours and allowed to warm to room temperature overnight. The mixture is poured into mixture of ice and concentrated hydrochloric acid, stirred and two layers are separated. The aqueous layer is extracted with methylene chloride and the combined methylene chloride layer is washed with brine, dried, and filtered. The filtrate is evaporated to an oil. This oil is purified by flash chromatography, affording 2.76 g of the desired product as a white solid.

mp 50°–52° C.

Calcd for $C_{16}H_{22}O_5$: C=65.29, H=7.53 Found C=65.39, H=7.60

EXAMPLE 57

3,4-Dimethoxy-E-oxo-benzene hexanoic acid

A mixture of 2.5 g of ethyl 3,4-dimethoxy-E-oxo-benzene hexanoate and 16 mL of 10% alcoholic sodium hydroxide is stirred at room temperature for 3 hours. The mixture is diluted with water and the ethyl alcohol is removed at reduced pressure. The solution is acidified with concentrated hydrochloric acid. The solid obtained is collected by filtration, washed with water and dried to afford 2.2 g of the desired product as a beige solid.

mp 123°–125° C.

Calcd for $C_{14}H_{18}O_5$: C=62.72, H=6.84 Found C=62.67, H=6.73

EXAMPLE 58

2-[6-(3,4-Dimethoxyphenyl)-1,6-dioxohexyl-1,2,3,4-tetrahydro-6,7-dimethoxyisoquinoline]

To a suspension of 1.73 g of 6,7-dimethoxy- 1,2,3,4-tetrahydroisoquinoline hydrochloride in 20 mL of N,N-dimethylformamide is added 4.2 mL of triethylamine. The solution is stirred for 5 minutes, cooled with ice bath and 2.0 g of 3,4-dimethoxy-E-oxo-benzene hexanoic acid is added, followed by the addition of 1.5 g of diethylcyanophosphonate. The ice bath is removed and the mixture is stirred at room temperature overnight. The mixture is poured into water and extracted with ethyl acetate. The ethyl acetate extract is washed with 2N hydrochloric acid, a saturated solution of sodium bicarbonate, brine, and dried. The solvent is removed to afford 3.15 g of the desired product as a white solid.

mp 101°–103° C.

$^1$H NMR(CDCl$_3$):δ 7.60–7.53(m,2H,Ar); 6.9–6.86(m, 1H,Ar); 6.63–6.6(m,2H,Ar); 4.65–4.56(2s,@H); 3.95–3.93(m,6H, OCH$_3$); 3.87–3.85(m,6H,OCH$_3$); 3.83–3.67 (2t,2H); 2.99(t,2H); 2.84–2.75(2t,2H); 2.47(t, 2H); 1.88–1.76 (m,4H).

EXAMPLE 59

2-[6-(3,4-Dimethoxyphenyl)-6-hydroxy]-1-oxohexyl]-1,2,3,4-tetrahydro-6,7-dimethoxyisoquinoline]

A mixture of 1.4 g of 2-[6-(3,4-dimethoxyphenyl)- 1,6-dioxohexyl-1,2,3,4-tetrahydro-6,7-dimethoxyisoquinoline] and 0.28 g of sodium borohydride in 25 mL of methyl alcohol is stirred at room temperature overnight. The mixture is poured into water and extracted with ethyl acetate. The ethyl acetate extract is washed with brine, dried and filtered. The filtrate is evaporated to afford 1.4 g of the desired product as a colorless oil.

EXAMPLE 60

2,-[6-(Cyclohexylthio]-6-(3,4-dimethoxyphenyl)-1-oxohexyl]-1,2,3,4-tetrahydro-6,7-dimethoxy isoquinoline To a solution of 1.0 g of 2-[6-(3,4-dimethoxyphenyl)-6-hydroxy]-1-oxohexyl]-1,2,3,4-tetrahydro- 6,7-dimethoxyisoquinoline in 10 mL of 1,2-dichloroethane is added 0.72 g of zinc iodide, followed by the addition of 0.30 g of cyclohexyl mercaptan. The resulting mixture is stirred at room temperature for 1 hour, poured into water and extracted with methylene chloride. The methylene chloride layer is washed with sodium hydroxide, brine, dried and evaporated to afford 1.06 g of the desired product as a glassy solid.

Calcd for $C_{31}H_{43}NSO_5$: C=68.73, H=8.00, N=2.59, S=5.92 Found C=68.35, H=7.95, N=2.42, S=5.87

EXAMPLE 61

2-[6-(Cyclohexylthio)-6-(3,4-dimethoxyphenyl)-hexyl]-1,2,3,4-tetrahydro-6,7-dimethoxyisoquinoline A mixture of 0.959 g of 2-[6-(cyclohexylthio)- 6-(3,4-dimethoxyphenyl)-1-oxohexyl]- 1,2,3,4-tetrahydro-6,7-dimethoxyisoquinoline and 0.35 mL of borane-methylsulfide complex (10M) in 10 mL of tetrahydrofuran is heated under reflux for 2 hour, cooled and quenched with methyl alcohol. The volatiles are removed in vacuo. The residue is taken up in 10 mL of ethyl alcohol, 8 mL of 1N sodium hydroxide is added and the resulting mixture is heated under reflux for 2 hours. The solution is cooled, diluted with water and extrated with ethyl acetate. The ethyl acetate extract is washed with brine, dried and filtered. The filtrate is evaporated to yield an oil. This oil is purified by flash chromatography using 2% methyl alcohol in methylene chloride affording 0.71 g of the desired product as a light yellow oil.

Calcd for $C_{31}H_{45}NSO_4$ 0.5MEtOH: C=69.78, H=8.78, N=2.54, S=5.82. Found C=69.72, H=8.81, N=2.47, S=5.88

EXAMPLE 62

α-(Cyclohexylthio)-α-(3,4-dimethoxyphenyl)-3,4-dihydro6,7-dimethoxy-2(1H)-isoquinolineheptane nitrile The procedure of Example 3 is repeated using 2.7 g of α-(5-chloropentyl)-α-(cyclohexylthio)-3,4-dimethoxybenzeneacetonitrile and 2.53 g of 6,7-dimethoxy- 1,2,3,4-tetrahydroisoquinoline hydrochloride. This affords 2.5 g of the desired product as a light yellow oil.

MS(CI): m/z 553(MH$^+$).

Calcd for $C_{32}H_{44}N_2SO_4$: C=69.53, H=8.02, N=5.07, S=5.80 Found C=69.39, H=8.26, N=4.78, S=5.50

EXAMPLE 63

2-[6-(3,4-Dimethoxyphenyl)-1-oxo-6-[(phenylmethyl)thio]hexyl]-1,2,3,4-tetrahydro-6,7-dimethoxy-isoquinoline The procedure of Example 60 is repeated using 1.4 g of 2-[6-(3,4-dimethoxyphenyl)-6-hydroxy]-1-oxohexyl]-1,2,3,4-tetrahydro-6,7-dimethoxyisoquinoline and 0.44 g of benzyl mercaptan. This affords 1.5 g of the desired product as a colorless oil.

Calcd for $C_{32}H_{39}NSO_5$ 0.1M EtOAc: C=69.67, H=7.18, N=2.51, S=5.74 Found C=69.36, H=7.46, N=2.36, S=5.98

EXAMPLE 64

2-[6-(3,4-Dimethoxyphenyl)-6-[(phenylmethyl)thio]-hexyl]-1,2,3,4-tetrahydro-6,7-dimethoxyisoquinoline The procedure of Example 61 is repeated using 1.4 g of 2-[6-(3,4-dimethoxyphenyl)-1-oxo-6 -[(phenylmethyl)thio]hexyl]-1,2,3,4-tetrahydro-6,7 -dimethoxyisoquinoline. This affords 1.15 g of the desired product as a colorless oil.

Calcd for $C_{32}H_{41}NSO_4$: C=71.71, H=7.71, N=2.61, S=5.98 Found C=71.55, H=7.81, N=2.50, S=5.92

EXAMPLE 65

2-[6-(3,4-Dimethoxyphenyl)-6-[(1,1-dimethethyl)thio]-1-oxohexyl]-1,2,3,4-tetrahydro-6,7-dimethoxyisoquinoline The procedure of Example 60 is repeated using 1.4 g of 2-[6-(3,4-dimethoxyphenyl)-6-hydroxy]-1-oxohexyl]-1,2,3,4-tetrahydro-6,7-dimethoxyisoquinoline and 0.42 mL of 2-methyl-2-propane thiol. This affords 1.4 g of the desired product as a white foam.

Calcd for $C_{29}H_{41}NSO_5$ 0.1M EtOAc: C=65.64, H=8.18, N=2.32, S=5.31 Found C=65.61, H=8.14, N=2.40, S=5.98

$^1$H NMR(CDCl$_3$) :δ 6.91–6.57 (m,5H,Ar); 4.63–4.5(2s, 2H); 4.13–4.11(m, 1H); 3.89–3.85(m,6H,OCH$_3$); 3.78–3.62(2t, 2H); 2.81–2.27(m,2H); 2.34(t,2H); 1.92–1.66(m,6H); 1.26 (s, 9H, CH$_3$).

EXAMPLE 66

2-[6-(3,4-Dimethoxyphenyl]-6-[(1,1-dimethylethyl)thio]hexyl]-1,2,3,4-tetrahydro-6,7-dimethoxyisoquinoline The procedure of Example 61 is repeated using 1.3 g of 2-[6-(3,4-dimethoxyphenyl)-6-[(1,1-dimethylethyl)thio]-1-oxohexyl]-1,2,3,4-tetrahydro-6,7-dimethoxyisoquinoline. This affords 1.08 g of the desired product a colorless oil.

Calcd for $C_{29}H_{43}NSO_4$: C=69.42, H=8.64, N=2.79, S=6.39 Found C=69.27, H=8.90, N=2.66, S=6.25

EXAMPLE 67

2-[7-(3,4-Dimethoxyphenyl)-7-[(4-methylphenyl)-thio]heptyl]-1,2,3,4-tetrahydro-6,7,8-trimethoxy-isoquinoline The procedure of Example 49 is repeated using 5.31 g 4-[6-bromo-1-[(4-methylphenyl)thio]heptyl]-1,2-dimethoxybenzene, 3.29 g of 5,6-dimethoxyisoindoline and 2.65 g of 6,7,8-trimethoxy-1,2,3,4-tetrahydroisoquinoline. This affords 4.52 g of the desired product as a yellow oil.

EXAMPLE 68

5-[(3-Hydroxy-4-methoxyphenyl)methyl]-p-tolylthioether

Hydrogen bromide gas is bubbled through a ice cooled suspension of 1.54 g of 3-hydroxy-4-methoxybenzylalcohol 50 ml of toluene. The reaction mixture is stirred with cooling until the solution is saturated, approximately 20 minutes. The solution is decanted from a reddish gum and the filtrate is concentrated in vacuo at a temperature below 40° C. The residue (1.84 g, 85% yield) is dissolved in 50 ml of toluene and added to a previously made room temperature mixture of 0.12 g of tetra-n-butylammonium bisulfate, 10 ml of 1N sodium hydroxide, 40 ml of water and 2.52 g of p-cresol to which 1.68 g of sodium bicarbonate has been added. The resultion 2-phase system is stirred over night at room temperature. The layers are separated and the organic phase is dried and concentrated in vacuo to give 3.27 g of crude product. The residue is dissolved in chloroform and washed with dilute hydrochloric acid, dried and concentrated in vacuo. The residue is purified by flash chromatography (silica gel: hexane to chloroform to methyl alcohol, gradient) to give 1.84 g white crystals, which is recrystallized from hexane to give 1.29 g of the desired product.

mp 62°–63.5° C.

MS(CI) :m/z 278(M+NH$_4$)$^+$.

Calcd for $C_{15}H_{16}SO_2$: C=69.20, H=6.19, S=12.32 Found C=69.25, H=6.27, S=12.32

EXAMPLE 69

(1,1-Dimethylethyl)[2-methoxy-5-[[4-methylphenyl)-thio]methyl]phenoxy]dimethylsilane To a solution of 11.1 g of 5-[(3-hydroxy-4-methoxyphenyl)methyl]-p-tolyl-thioether in 40 mL of pyridine is added 7.46 g of t-butyldimethylsilyl chloride and 0.3 g of p-N,N-dimethylpyridine. This solution is heated to reflux for 3 hours and cooled to room temperature. The mixture is partitioned between chloroform and 1N hydrochloric acid. The organic layer is washed with brine and dried. The solvent is removed at reduced pressure and the residue distilled at 161°–165° C./0.03 mm affording 15.06 g of the desired product as a clear oil.

MS(CI): m/z 392 (M+NH$_4^+$).

Calcd for $C_{21}H_{30}SO_2Si$: C=67.33, H=8.07, S=8.56, Si=7.50 Found C=67.32, H=8.02, S=8.58, Si=7.32

EXAMPLE 70

[5-[7-Bromo-1-[(4-methylphenyl)thio]heptyl]-2-methoxyphenoxy](1,2-dimethylethyl)dimethylsilane The procedure of Example 40 is repeated using 14.0 g of (1,1-dimethylethyl)[2-methoxy-5-[[(4-methylphenyl)thio] methyl]phenoxy]dimethylsilane and 17.2 mL of 1,6 dibromohexane. This affords 15.94 g of the desired product as a yellow oil contaminated with 30% of the starting material, 1,2-dimethoxy-4-[[(4-methylphenyl)thio]methyl]benzene.

EXAMPLE 71

2-[7-[3-[[1,1-Dimethylsilyl]oxy-4-methoxyphenyl]-7-[(4-methylphenyl)thio]heptyl]-1,2,3,4-tetrahydro-6,7-dimethoxyisoquinoline The procedure of Example 49 is repeated using 10.75 g of [5-[7-bromo-1-[(4-methylphenyl)thio]heptyl]-2-methoxyphenoxy](1,2-dimethylethyl)dimethylsilane and 11.5 g of 6,7-dimethoxy-1,2,3,4-tetrahydroisoquinoline hydrochloride. This affords 10.6 g of desired product as a tan oil.

MS(CI): m/a 650 (MH$^+$).

Calcd for $C_{38}H_{55}NSO_4Si$: C=70.21, H=8.53, N=2.16, S=4.93, Si=4.32 Found C=69.99, H=8.43, N=2.05, S=5.35, Si=4.57

EXAMPLE 72

5-[7-(3,4-Dihydro-6,7-dimethoxy-2(1H)-isoquinolinyl)-1[(4-methylphenyl)thio]heptyl]-2-methoxyphenol To a solution of 10.28 g of 2-[7-[3-[[(1,1-dimethylsilyl] oxy-4-methoxyphenyl)-7-[(4-methylphenyl)thio]heptyl]-1,2,3,4-tetrahydro-6,7-dimethoxyisoquinoline in 150 mL of tetrahydrofuran is added 49 mL of tetrabutylammonium fluoride. The solution is stirred overnight and partitioned between chloroform and aqueous ammonium hydroxide. The organic layer is washed with brine, dried and passed through a pad of hydrous magnesium silicate. The solvent is removed at reduced pressure and the residue chromatographed on silica gel with a gradient elution going from hexane to chloroform to methyl alcohol. The desired material is dissolved in diethyl ether and passed through a short hydrous magnesium silicate pad to afford after solvent removal 8.75 g of the desired product as a brown oil.

MS(CI): m/z 536(M+H$^+$).

Calcd for $C_{32}H_{41}NSO_4$ ½$H_2O$: C=70.56, H=7.77, N=2.57, S=5.88 Found C=70.28, H=7.82, N=2.72, S=5.87

$^1$H NMR(CDCl$_3$):δ 7.16(d,2H,J=8,2MePhH); 7.01(d,2H, J=8, 2MePhH); 6.85 (d, 1H,OH,MeOArH); 6.70 (m, 20H, MeOArH); 6.58(s,1H, IQArH); 6.51(s,1H, IQArH); 5.6(br, 1H,OH); 3.96(t, 1H,1-CH); 3.83(m,9H,3ArOCH$_3$); 3.52(s, 2H, IQ 1-CH$_2$); 2.81, 2.70 (2t,4H,IQ3+4-CH$_2$); 2.44(t,2H, 7-CH$_2$); 2.28(s,3H,Ar-CH$_3$); 1.87 (m,2H,6-CH$_2$); 1.55(m, 2H).

EXAMPLE 73

2-[7-[3-(2-Chloroethoxy)-4-methoxyphenyl]-7-[(4-methyl phenyl)thio]heptyl]-1,2,3,4-tetrahydro-6,7-dimethoxyisoquinoline To a stirred solution of 5.57 g of 5-[7-(3,4-dihydro-6,7-dimethoxy-2 (1H)-isoquinolinyl)-1-[(4-methylphenyl)thio]heptyl]-2-methoxyphenol and 2.0 mL of 2-chloroethyl tosylate in 50 mL of 2-butanone is added 0.44 g of 60% sodium hydride in oil. The solution is heated to reflux for 48 hours and then cooled to room temperature. The solution is partitioned between chloroform and brine and the organic layer dried. The solvent is removed at reduced pressure and the residue chromatographed on silica gel with a gradient elution going from hexane to chloroform to methyl alcohol. The desired fractions are concentrated, dissolved in diethyl ether and passed through a short hydrous magnesium silicate pad. The solvent is removed at reduced pressure to afford 1.6 g of the desired product as a light tan gum.

MS(CI): m/z 598(M+H$^+$) and 474(M-(TolSH)+H$^+$).

Calcd for $C_{34}H_{44}ClNSO_4$: C=68.26, H=7.41, N=2.34, Cl=5.93, S=5.36 Found C=68.41, H=7.01, N=2.12, Cl=5.71, S=5.15

EXAMPLE 74

1,2,3,4-Tetrahydro-2-[7-[3-[2-(1H-imidazol-1-yl)-ethoxy]-4-methoxyphenyl]-7-[(4-methylphenyl)thio]-heptyl]-6,7-dimethoxyisoquinoline To 0.76 g of imidazole in 5 mL of 4A sieve-dried N,N-dimethylformamide is added 0.18 g of 60% sodium hydride in oil. When the effervescence subsides, 0.26 g of sodium iodide is added, followed by 1.12 g of 2-[7-[3-(2-chloroethoxy)-4-methoxyphenyl]-7-[(4-methylphenyl)thio] heptyl]-1,2,3,4-tetrahydro-6,7-dimethoxyisoquinoline in 5 mL of N,N-dimethylformamide. An additional 2 mL of N,N-dimethylformamide is used as wash. After letting the tan solution stand for 48 hours, it is concentrated in vacuo, and the residue is distributed between ethyl acetate and water. The organic layer is extracted with 1N hydrochloric acid, the acid layer basified with aqueous ammonia, and the resulting oil extracted into ethyl acetate. After drying (sodium sulfate), the extract is concentrated in vacuo to 0.53 g of tan oil. Flash chromatography of the oil on silica gel (gradient elution: hexane to chloroform to methyl alcohol) gives an oil which is taken up in ethyl acetate, passed through a pad of hydrous magnesium silicate, and concentrated to leave 0.194 g of the desired product as a yellow gum.

MS(CI): m/z 630(MH$^+$).

Calcd for $C_{37}H_{47}N_3SO_4$ $H_2O$: C=68.60, H=7.62, N=6.49, 8–4.94 Found C=68.83, H=7.53, N=6.32, S=4.82

$^1$H NMR(CDCl$_3$):δ 7.62(s,1H, Z-Im-H); 7.12(s,1H,Im-H); 7.80(d,2H,J=8,2MePhH); 7.0S(s,1H,2-Im-H); 6.99(d, 2H, J=8,2MePhH); 6.76(m,2H, (MeO)2ArH); 6.64(m, 1H, (MeO) 2ArH); 6.59(s,1H,IQ,ArH); 6.51(s,1H,IQ,ArH); 4.3(m,2H, ethoxy CH$_2$); 4.17 (m,2H,ethoxy CH$_2$); 3.95(t, 1H,1-CH); 3.83(m,9H,ArOCH$_3$); 3.53(s,2H, IQ,1-CH$_2$); 2.81,2.71(2t, 4H,IQ,3+4-CH$_2$); 2.45(t,2H,1-CH$_2$); 2.26(s, 3H,Ar-CH$_3$); 1.88(m,2H,2-CH$_2$); 1.55(m,2H,6-CH$_2$); 1.29(m,6H,3,4,5 (CH$_2$)$_3$).

EXAMPLE 75

1,2,3,4-Tetrahydro-2-[7-[3-[2-(1H-imidazol-1-yl)-ethoxy]-4-methoxyphenyl]-7-[(4-methylphenyl)thio]-heptyl-6,7-dimethoxyisoquinoline dihydrochloride The procedure of Example 34 is used with 0.77 g of 1,2,3,4-tetrahydro-2-[7-[3-[2-(1H-imidazol-1-yl)ethoxy]-4-methoxyphenyl]-7-[(4-methylphenyl)thio]heptyl]-6,7-dimethoxyisoquinoline. This affords 0.32 g of the desired product as a yellow gum.

MS(FAB): m/z 575 (M$^+$).

Calcd for $C_{37}H_{47}N_3SO_4$ 15/8HCl $H_2O$: C=62.85, H=7.22, N=8.15, Cl=8.15, S=4.53 Found C=62.70, H=7.45, N=5.57, Cl=8.11, S=4.48

EXAMPLE 76

2-[6-(3,4-Dimethoxyphenyl)-6-hydroxy-1-oxooctyl]-1,2,3,4-tetrahydro-6,7-dimethoxyisoquinoline A mixture of 3.0 g of 2-[6-(3,4-dimethoxyphenyl)-1,6-dioxohexyl-1,2,3,4-tetrahydro-6,7-dimethoxyisoquinoline and 15.0 mL of ethyl magnesium bromide (1M) in tetrahydrofuran in 20.0 mL of anhydrous tetrahydrofuran is stirred at room temperature overnight. The mixture is poured into a mixture of ice and saturated solution of ammonium chloride and extracted with diethyl ether. The diethyl ether extract is washed with brine, dried, filtered. The filtrate is evaporated to afford 3.0 g of the desired product as a colorless oil.

EXAMPLE 77

2-[6-(3,4-Dimethoxyphenyl)-6-[(4-methylphenyl)thio]-1-oxooctyl]-1,2,3,4-tetrahydro-6,7-dimethoxy-isoquinoline The procedure of Example 60 is repeated using of 2.7 g of 2-[6-(3,4-dimethoxyphenyl)-6-hydroxy-1-oxooctyl]-1,2,3,4-tetrahydro-6,7-dimethoxyisoquinoline and 1.06 g of p-thiocresol. This affords 1.92 g of the desired product as a white foam.

Calcd for $C_{34}H_{43}NSO_5$ 0.15M EtOAc: C=70.31, H=7.54, N=2.37, S=5.42 Found C=69.97, H=7.58, N=2.32, S=5.34

EXAMPLE 78

2-[6-(3,4-Dimethoxyphenyl)-6-[(4-methylphenyl)thio]-octyl]-1,2,3,4-tetrahydro-6,7-dimethoxyisoquinoline The procedure of Example 61 is repeated using 1.7 g of 2-[6-(3,4-dimethoxyphenyl)-6-[(4-methylphenyl)thio]-1-oxooctyl]-1,2,3,4-tetrahydro-6,7-dimethoxyisoquinoline. This affords 1.33 g of the desired product as a colorless oil.

Calcd for $C_{34}H_{45}NSO_4$ 0.5M EtOH: C=71.63, H=8.24, N=2.39, S=5.46 Found C=71.35, H=8.29, N=2.34, S=5.40

EXAMPLE 79

4,5-Dichloro-1,2-benzenedimethanol

A 1.24 g portion of 4,5-dichlorophthalic acid is dissolved in 40 mL anhydrous tetahydrofuran and the solution is cooled to 0° C. To this solution is slowly added 4 mL of borane-methyl sulfide. The reaction flask is first warmed to room temperature, then heated to reflux for 12 hours. The product mixture is cooled to 0° C., then slowly quenched with 50 mL methyl alcohol. Following removal of the solvent, the residue is partitioned between 40 mL water, and 100 mL 1:1 ethyl acetate tetrahydrofuran. The organic layer is washed with 30 mL brine, then dried over magnesium sulfate. Purification by silica gel chromatography (2:1 ethyl acetate/hexane) affords 1.01 g of the desired product as a white solid, m.p. 128°–136° C.

MS(Hi res): m/z

Calcd for $C_8H_8Cl_2O_2$ 205.9901 Found 205.9872

EXAMPLE 80

1,2-Bis(bromomethyl)-4,5-dichlorobenzene

A 2.53 g portion of N-bromosuccinimde is added to 40 mL methylene chloride and 5 mL diethyl ether ether. The solution is cooled to 0° C. and 1.25 mL methyl sulfide is slowly added via a syringe. A yellow solid is formed. Following complete addition of the methyl sulfide, the reaction mixture is cooled to −20° C. To this is added 0.736 g of 4,5-dichloro-1,2-benzenedimethanol. The reaction mixture is warmed to 0° C. and stirred for 3 hours, followed by quenching with 30 mL of ice water. A further 30 mL of methylene chloride is added and the layers are separated. The organic layer is washed with 20 mL brine, and dried over magnesium sulfate. Purification by silica gel chromatography (2:1 ethyl acetate/hexane) provides 0.40 g of the desired product as a white solid.

mp 55°–56° C.

MS(Hi res): m/z

Calcd for $CSH_6Cl_2Br_2$ 329.8214 Found 329.8215

EXAMPLE 81

5,6 Dichloro-α-(3,4-dimethoxyphenyl)-1,3-dihydro-α-[4-methylphenyl]thio]-2-H-isoindole-2-heptanenitrile The procedure of Example 27 is used with 0.52 g of α-(5-aminopentyl)-3,4-dimethoxy-α-[(4-methylphenyl)thio] benzeneacetonitrile and 0.3 g of 1,2-bis(bromomethyl)-4,5-dichlorobenzene. This affords 0.475 g of the desired product as a yellow oil.

MS(Hi res EI): m/z

Calcd for $C_{30}H_{32}N_2O_2Cl_2$ 554.1561 Found 554.1525 C=64.86, H=5.81, N=5.04, Cl=12.76, S=5.77 Found C=64.74, H=5.56, N=4.78, Cl=12.27, S=5.67

EXAMPLE 82

α-(Cyclohexylthio)-3,4-dimethoxybenzeneacetonitrile

The procedure of Example 1 is repeated using 10.2 g of α-chloro-3,4-dimethoxybenzeneacetonitrile and 6.2 mL of cyclohexy mercaptan. This affords 7.8 g of the desired product as light yellow crystals.

mp 80°–82° C.

MS(CI): m/z 292(MI$^+$).

Calcd for $C_{16}H_{21}NO_2S$: C=65.95, H=7.26, N=4.81, S=11.00 Found C=66.06, H=7.29, N=4.82, S=10.88

EXAMPLE 83

α-(5-chloropentyl)-α-[cyclohexylthio]-3,4-dimethoxybenzeneacetonitrile

The procedure of Example 2 is repeated using 3.0 g of α-(cyclohexylthio)-3,4-dimethoxy benzeneacetonitrile and 2.0 mL of bromo-5-chloropentane. This affords 3.1 g of the desired product as a colorless oil.

MS(CI): m/z 395(M).

EXAMPLE 84

α-(Cyclohexylthio]-α-(3,4-dimethoxyphenyl)-1,3-dioxo-2H-isoindole-2-heptanenitrile The procedure of Example 24 is repeated using 2.1 g of α-(5-chloropentyl)-α-(cyclohexylthio)-3,4-dimethoxybenzeneacetonitrile and 0.954 g of the potassium salt of phthalimide. This affords 2.13 g of the desired product as a colorless oil.

Calcd for $C_{29}H_{34}N_2SO_4$: C=68.75, H=6.76, N=5.53, S=6.33 Found C=68.49, H=6.84, N=5.35, S=5.98

EXAMPLE 85

α-(5-Aminopentyl)-α-(cyclohexylthio)-3,4-dimethoxy benzeneacetonitrile

The procedure of Example 25 is repeated using 2.0 g of α-(cyclohexylthio)-α-(3,4-dimethoxyphenyl)- 1,3-dioxo-2H-isoindole-2-heptanenitrile and 3.0 mL of hydrazine hydrate. This affords 1.32 g of the desired product as a light yellow oil.

Calcd for $C_{21}H_{32}N_2SO_2$ 0.7M $H_2O$: C=64.81, H=8.81, N=7.20, S=8.24 Found C=65.04, H=8.49, N=6.98, S=8.20

EXAMPLE 86

α-(Cyclohexylthio)-α-(3,4-dimethoxyphenyl)-1,3-dihydro5,6-dimethoxy-2(1H)-isoindoleheptane nitrile To a solution of 1.12 g of α-(5-aminopentyl)-α-(cyclohexylthio)-3,4-dimethoxybenzeneacetonitrile in 15 mL of N,N-dimethylformamide is added 0.7 g of 1,2-bischloromethyl-3,4-dimethoxybenzene, 1.64 g of potassium carbonate and 0.025 g of potassium iodide. The solution is stirred at 90° C. for 24 hours and then cooled. The solution is poured into water and extracted with ethyl acetate. The organic layer is washed with brine, dried over sodium sulfate and the solvent removed at reduced pressure. The residue is purified three times via flash chromatography using methylene chloride/methyl alcohol (98:2). The yellow oil obtained is dissolved in diethyl ether and filtered through a pad of diatomaceous earth. This affords 0.5 g of the desired product as a dark glassy solid.

MS(FAB): m/z 539.

Calcd for $C_{31}H_{42}N_2SO_4$: C=69.11, H=7.86, N=5.20, S=5.95 Found C=68.96, H=7.96, N=4.95, S=5.92

EXAMPLE 87

5-[[(4-Methylphenyl)thio]methyl]-1,3-benzodioxole

To a solution of 28.5 g of p-thiocresol in 250 mL of water is added 8.8 g of sodium hydroxide. The solution is heated on a steam bath briefly with vigorous stirring and then cooled to room temperature. To this solution is added 250 of toluene, 39.7 g of a 50% by weight solution of 3,4-methylenedioxybenzyl chloride in methylene chloride and 3.3 g of tetrabutylammonium chloride. This solution is stirred at room temperature for one hour and then 4.4 g of sodium hydroxide is added. The resulting solution is stirred at room temperature overnight and then partitioned. The organic layer is washed with 1N sodium hydroxide, brine, and dried over sodium sulfate. The solvent is removed at reduced pressure and the residual brown oil is purified via column chromatography using hexane/chloroform (2:1). This affords 24 g of the desired product as a clear oil.

MS(CI): m/z 259 (MH⁺).

Calcd for $C_{15}H_{14}O_2S$: C=69.74, H=5.46, S=12.41 Found C=69.53, H=5.36, S=12.69

EXAMPLE 88

5-[6-Bromo-1-[(4-methylphenyl)thio]hexyl-1,3-benzodioxole

The procedure of Example 40 is repeated using 23.44 g of 5-[[(4-methylphenyl)thio]methyl]-1,3-benzodioxole and 24.7 mL of 1,5-dibromopentane. This affords 23 g of the desired product as a clear oil.

MS(CI): m/z 408(MH⁺).

Calcd for $C_{20}H_{23}BrO_2S$: C=58.96, H=5.69, Br=19.62, S=7.87 Found C=59.09, H=5.73, Br=19.65, S=7.80

EXAMPLE 89

2-[6-(1,3-Benzodioxol-5-yl)-6-[(4-methylphenyl]-thiohexyl]-1,2,3,4-tetrahydro-6,7-dimethoxyisoquinoline The procedure of Example 49 is repeated using 4.07 g of the 5-[6-bromo-1-[(4-methylphenyl)thio]hexyl- 1,3-benzodioxole and 4.6g of 4.6 g of 6,7-dimethoxy- 1,2,3,4-tetrahydroisoquinoline hydrochloride. This affords 4.2 g of the desired product as a yellow oil.

MS(CI): m/z 520(MH⁺).

Calcd for $C_{31}H_{37}NO_4S$: C=71.65, H=7.18, N=2.70, S=6.17 Found C=71.52, H=7.33, N=2.72, S=5.90

EXAMPLE 90

1-[[(4-Methylphenyl)thio]methyl]-4-(trifluoromethoxy)benzene

The procedure of Example 87 is repeated using 11.8 g of p-thiocresol and 9.6 g of 4-(trifluoromethoxy)benzyl chloride. This affords 10.9 g of the desired product as white crystals.

mp 74°–76° C.

MS(CI): m/z 299 (MH⁺).

Calcd for $C_{15}H_{13}F_3OS$: C=60.39, H=4.39, F=19.11, S=10.75 Found C=60.33, H=4.26, F=19.34, S=11.01

EXAMPLE 91

1-[6-Bromo-1-[(methylphenyl)thio)hexyl]-4-(trifluoromethoxy)benzene

The procedure of Example 40 is repeated using 9.95 g of 1-[[(4-methylphenyl)thio]methyl]-4-(trifluoromethoxy)benzene and 23.0 g of 1,5-dibromopentane. This affords 13.0 g of the desired product as a yellow gum.

MS(Hi res): m/z

Calcd for $C_{20}H_{22}F_3BrOS$ 446.0527 Found 446.0527

EXAMPLE 92

1,2,3,4-Tetrahydro-6,7-dimethoxy-2-[6-[(4-methylphenyl)thio]-6-[trifluoromethoxy)phenyl]hexyl-isoquinoline The procedure of Example 46 is repeated using 7.16 g of 1-[6-bromo-1-[(methylphenyl)thio]hexyl]-4-(trifluoromethoxy)benzene and 4.6 g of 6,7-dimethoxy- 1,2,3,4-tetrahydroisoquinoline hydrochloride. This affords 6.24 g of the desired product as a yellow gum.

MS(CI): m/z 560(MH$^+$).

Calcd for $C_{31}H_{36}F_3NO_3S$: C=66.52, H=6.48, N=2.50, F=10.18, S=5.73 Found C=66.38, H=6.46, N=2.47, F=10.36, S=5.84

EXAMPLE 93

1-Fluoro-4-[[(4-methylphenyl)thio]methyl]benzene

To a 10° C. solution of 1.93 g of 60% sodium hydride in 50 mL of N,N-dimethylformamide is added dropwise a solution of 4.16 g of p-thiocresol in 10 mL of N,N-dimethylformamide. The solution is stirred for 20 minutes at 5° C.; then 40 minutes at room temperature. The solution is cooled to 5° C. and 5.67 g of 4-fluorophenylbenzyl bromide in 10 mL of N,N-dimethylformamide is added dropwise. The solution is allowed to warm to room temperature overnight. The mixture is poured onto 50 mL of water and the solid collected by filtration. This affords after drying, 5.0 g of the desired product as a white solid.

Calcd for $C_{14}H_{13}FS$: C=72.38, H=5.64, F=8.18, S=Not analyzed Found C=72.48, H=5.66, F=8.37, S=Not analyzed

EXAMPLE 94

1-[[6-Bromo-1-(4-fluorophenyl)hexyl]thio]-4-methylbenzene

The procedure of Example 40 is repeated using 1.39 g of 1-fluoro-4-[[(4-methylphenyl)thio]methyl]benzene and 4.5 mL of 1,6-dibromohexane. This affords 0.49 g of the desired product as a yellow semisolid.

$^1$H NMR(CDCl$_3$):δ 7.25–6.9(m, 8H); 4.0(dd,1H); 3.35(t, 2H, CH$_2$Br); 2.2S(s,3H,ArCH$_3$); 1.8(m,4H); 1.3(m,6H).

EXAMPLE 95

2-[7-(4-Fluorophenyl)-7-[(4-methylphenyl)thio]heptyl]-1,2,3,4-tetrahydro-6,7-isoquinoline The procedure of Example 3 is repeated using 0.49 g of the 1-[[6-bromo-1-(4-fluorophenyl)hexyl]thio]-4-methylbenzene and 0.284 g of 6,7-dimethoxy- 1,2,3,4-tetrahydroisoquinoline hydrochloride. This affords 0.457 g of the desired product as a colorless oil.

$^1$H NMR(CDCl$_3$):δ 7.23–6.9(m,8H,Ar); 6.58(s,1H,Ar); 6.51(s,1H,Ar); 4.08(m, 1H), 3.83(d,6H,OCH$_3$); 2.88–2.42 (m,6H); 2.69(s,3H,CH$_3$); 1.95–1.25(m,10H).

EXAMPLE 96

1,2,3,4-Tetrahydro-6-methoxy-7-(phenylmethoxy)-isoquinoline hydrochloride

To a solution of 0.63 g of 3,4-dihydro-7-hydroxy- 6-methoxy-2(1H)-isoquinolinecarboxylic acid, 1,1-dimethylethyl ester in 10 mL of N,N-dimethylformamide is added 0.092 g of 60% sodium hydride in oil. The solution is stirred at room temperature for one hour and then 0.578 g of benzyl bromide is added. The solution is stirred at room temperature for 72 hours. The volatiles are removed at reduced pressure and the residue taken up in ethyl acetate. The solution is washed with water and the organic layer dried over magnesium sulfate. The solvent is removed at reduced pressure and the residue taken up in 20 mL of diethyl ether. This solution is cooled to 0° C. and 10 mL of 4.5 M hydrochloric acid in ethyl alcohol is added. The solvent is removed at reduced pressure and the residue taken up in a minimum amount of hot ethyl alcohol. After cooling to room temperature, an equal volume of diethyl ether is added. The white solids are collected and washed with diethyl ether. This affords 0.56 g of the desired product as a white solid, mp 217°–219° C.

MS(Hi res): m/z

Calcd for $C_{17}H_{20}NO_2Cl$ 269.1494 Found 270.1494 (MH$^+$)

Calcd for $C_{17}H_{20}NO_2Cl$: C=65.41, H=6.64, N=4.49, Cl=11.93 Found C=65.63, H=6.10, N=4.48, Cl=11.59

EXAMPLE 97

α-(3,4-Dimethoxyphenyl)-3,4-dihydro-6-methoxy-α-[(4-methylphenyl)thio]-7-(phenylmethoxy)-2(1H)-isoquinoline The procedure of Example 3 is repeated using 0.89 g of α-(5-chloropentyl)-3,4-dimethoxy-α-[(4-methylphenyl)thio]benzeneacetonitrile and 0.56 g of 1,2,3,4-tetrahydro-6-methoxy-7-(phenylmethoxy)isoquinoline hydrochloride. This affords 0.5 g of the desired product as a colorless gum.

MS(Hi res): m/z

Calcd for $C_{39}H_{44}N_2SO_4$ 636.3021 Found 636.3087

Calcd for $C_{39}H_{44}N_2SO_4$ $_{/12}$O: C=71.53, H=7.08, N=4.28, S=4.87 Found C=71.16, H=7.05, N=4.04, S=4.77

EXAMPLE 98

3,4-Dihydro-7-[[(1,1-dimethylethyl)dimethylsilyl]oxy]-6-methoxy-2(1H)-isoquinolinecarboxylic acid-1,1-dimethylethyl ester To a dry flask is added 6.7 g of 6-hydroxy- 7-methoxy-1,2,3,4-tetrahydroisoquinoline, 4.98 g di-t-butyl dicarbonate and 40 mL methylene chloride. The solution is cooled to 0° C. and 4.77 mL diisopropylethylamine is slowly added to the reaction mixture, followed by 0.010 g of p-dimethylaminopyridine. The mixture is warmed to room temperature and stirred for 15 hours. Following evaporation of the solvent, the crude product mixture is placed directly on a silica gel column (eluting with 5:1 hexane/ethyl acetate) yielding 8.1 g of the desired product as a white solid.

mp 46°–49° C.

MS(Hi res): m/z

Calcd for $C_{21}H_{35}NO_4Si$ 393.2335 Found 393.2307

Calcd for $C_{21}H_{35}NO_4Si$: C=64.08, H=8.96, N=3.56 Found C=63.81, H=8.97, N=3.48

EXAMPLE 99

3,4-Dihydro-7-hydroxy-6-methoxy-2(1H)-isoquinolinecarboxylic acid 1,1-dimethylethyl ester A 6.0 g portion of 3,4-dihydro-7-[[(1,1-dimethylethyl)dimethylsilyl]oxy]-6-methoxy-2(1H)-isoquinolinecarboxylic acid-1,1-dimethylethyl ester is dissolved in 30 mL tetrahydrofuran and cooled to 0° C. To this is added 22.8 mL of a 1.0M solution of tetra, butylammonium fluoride, while stirring. The reaction mixture is brought to room temperature, and stirred for three hours. The reaction is quenched with 10 mL saturated sodium bicarbonate solution and 10 mL water, followed by the addition of 20 mL diethyl ether. After separating the layers, the aqueous phase is extracted with 2×20 mL diethyl ether. The combined organic layers are washed with 20 mL brine, and dried over magnesium sulfate. Following removal of the solvent, the product is purified by silica gel chromatography (eluting with 2:1 hexane/ethyl acetate) to produce 4.15 g of the desired product as a white solid.

mp 80°–83° C.

MS(Hi res): m/z

Calcd for $C_{15}H_{21}NO_4$ 279.1470 Found 279.1469

Calcd for $C_{15}H_{21}NO_4$: C=64.50, H=7.58, N=5.01 Found C=64.47, H=7.61, N=5.19

EXAMPLE 100

3,4-Dihydro-6-methoxy-7-[[(trifluoromethyl)sulfonyl]-oxy]-2(1H)-isoquinolinecarboxylic acid 1,1-dimethyl ethyl ester To a dry flask, under argon, is added 2.54 g of 3,4-dihydro-7-hydroxy-6-methoxy-2(1H)-isoquinolinecarboxylic acid 1,1-dimethylethyl ester and 20 mL dry pyridine. The mixture is cooled to 0° C. and 1.68 mL triflic anhydride is slowly added. After warming up to room temperature and stirring for 15 hours, the reaction mixture is quenched with 70 mL water. A 100 mL portion of diethyl ether is added, and the layers are separated. The diethyl ether layer is washed with 2×30 mL 10% HCl, 2×20 mL water, and 30 mL brine. Following removal of the solvent, the residue is purified by silica gel chromatography (eluting with 3:1 hexane/ethyl acetate) to produce 3.21 g of the desired product as a white solid.

mp 100°–102° C.

Calcd for $C_{16}H_{20}NO_6F_3S$ 411.0963 Found 411.1016

Calcd for $C_{16}H_{20}NO_6F_3S$: C=46.71, H=4.90, N=3.40 Found C=46.88, H=5.12, N=3.33

EXAMPLE 101

1,2,3,4-Tetrahydro-6-methoxy-7-isoquinolinyl trifluoromethanesulfonic acid ester To a flask is added 8 mL of 4.5M hydrochloric acid/ethyl alcohol which is cooled to 0° C. Then a 0.400 g portion of 3,4-dihydro-6-methoxy-7-[[(trifluoromethyl)sulfonyl]-oxy]-2(1H)-isoquinolinecarboxylic acid 1,1-dimethyl ethyl ester dissolved in 1 mL diethyl ether is added. The reaction mixture is warmed to room temperature and stirred for an additional 30 minutes. Following evaporation of the solvent, 40 mL chloroform and 25 mL aqueous sodium bicarbonate are added to the residue. The layers are separated and the organic phase is dried over magnesium sulfate. The chloroform is evaporated, yielding 0.303 g of the desired compound as a yellow gum.

$^1$H NMR(CDCl$_3$) :δ 6.90(s,1H); 6.74(s,1H); 3.94(s,2H); 3.89(s,3H); 3.13(t,J=6,2H); 2.81(t,J=6,2H); 2.40(brs, 1H).

EXAMPLE 102

2-[6-Cyano-6(3,4-dimethoxyphenyl)-6-[(4-methylphenyl)thio]hexyl]-1,2,3,4-tetrahydro-5-methoxy-7-isoquinoline trifluoromethanesulfonic acid To 0.3 g of 1,2,3,4-tetrahydro-6-methoxy-7-isoquinolinyl trifluoromethanesulfonic acid ester is added 0.540 g of α-(5-iodopentyl)-3,4-dimethoxy-α-[(4-methylphenyl)thio] benzeneacetonitrile, 10 mL acetonitrile and finally, 0.51 mL diisopropylethylamine. The mixture is brought to reflux for 15 hours. After allowing the reaction to cool to room temperature, the solvent is concentrated in vacuo. The resulting residue is partitioned between 50 mL diethyl ether and 30 mL 1N sodium hydroxide. After separating layers, the aqueous layer is further extracted with 30 mL diethyl ether. The combined organic layers are washed with 20 mL water and brine successively, and dried over magnesium sulfate. Following removal of the solvent, the product is purified by silica gel chromatography (eluting with 95:5 methylene chloride/methyl alcohol) to produce 0.402 g of the desired product as a white foam.

MS(Hi res): m/z

Calcd for $C_{33}H_{37}N_2O_6F_3S_2$ 678.2045 Found 678.2270

Calcd for $C_{33}H_{37}N_2O_6F_3S2$: C=58.39, H=5.49, N=4.13, S=9.45 Found C=58.32, H=5.39, N=4.05, S=9.52

EXAMPLE 103

1,2-Bis(chloromethyl)-4-methoxy-5-(phenylmethoxy)-benzene

To a mixture of 12.0 g of 1-methoxy-2-(phenylmethoxy)benzene, 18.0 mL of 37% formaldehyde and 2.0 g of zinc iodide in 200 mL of diethyl ether is bubbled hydrogen chloride gas at a rate such that a gentle reflux is maintained. The addition of hydrogen chloride gas is stopped after 1.5 hours and the solution stirred for an additional 1.5 hours. The solution is poured into ice water and extracted with diethyl ether. The organic layer is washed with brine and dried over sodium sulfate. The volatiles are removed to afford 15.0 g of an oil. This oil is taken up in diethyl ether and passed through a short pad of hydrous magnesium silicate with 400 mL of diethyl ether. The volatiles are removed and the residual oil purified using 4% ethyl acetate in hexane. This affords 1.36 g of the desired product as a white fluffy solid.

mp 114°–116° C.

$^1$H NMR(CDCL$_3$):δ 7.46–7.31(m,5H,Ar); 6.91(s,1H,Ar); 5.15(s,2H,OCH$_2$Ph); 4.69(s,1H,CH$_2$Cl); 4.65(s,1H,CH$_2$Cl); 3.88 (s, 3H,OCH$_3$) .

EXAMPLE 104

2,3-Dihydro-5-methoxy-6-(phenylmethoxy)-2-(phenylmethyl]-1H-isoindole

The procedure of Example 26 is repeated using 1.0 g of bis(chloromethyl)-4-methoxy-5-(phenylmethoxy)benzene and 0.6 mL of benzyl amine. This affords 0.74 g of the desired product as a beige solid.

mp 94°–96° C.

MS(FAB): m/z 346 (M+H).

Calcd for $C_{23}H_{23}NO_2$ 0.05M CH$_2$Cl$_2$: C=79.16, H=6.66, N=4.01 Found C=78.96, H=6.76, N=3.87

EXAMPLE 105

2,3-Dihydro-α-methoxy-1H-isoindol-5-ol

To 35 mL of ethyl alcohol is added 0.5 g of 2,3-dihydro-5-methoxy-6-(phenylmethoxy)-2-(phenylmethyl)-1H-isoindole. The solution is warmed until everything is dissolved. The solution is cooled to room temperature and 0.13 g of 35% palladium hydroxide on carbon is added. The resulting mixture is shaken on a Parr apparatus at 50 pounds per square inch for 21 hours. The solution is filtered through a pad of diatomaceous earth and the pad washed with ethyl alcohol. The volatiles are removed to afford 0.209 g of the desired product as a tan solid.

EXAMPLE 106

α-(5-Bromopentyl)-3,4-dimethoxy-α-[(4-methylphenyl)thio]benzeneacetonitrile

To a solution of 7.0 g of 3,4-dimethoxyacetonitrile in 160 mL of anhydrous tetrahydrofuran is added 1.12 g of 50% sodium hydride in oil. After the solution is stirred at room temperature for 1.5 hours, 12.3 mL of 1,5-dibromopentane is added in one portion. The solution is stirred at room temperature for 3.5 hours and then poured into water. The mixture is extracted with diethyl ether (2×250 mL) and the organic layer is washed with brine and dried over magnesium sulfate. The volatiles are removed at reduced pressure and the residue purified via column chromatography using a gradient elution from hexane to 10% ethyl acetate in hexane. This affords 8.8 g of the desired product as a colorless oil.

MS(CI): m/z 448.45(MH$^+$).

Calcd for $C_{22}H_{26}BrNO_2S$: C=58.92, H=5.84, N=3.12, Br=17.82, S=7.15 Found C=58.80, H=5.75, N=2.96, Br=17.59, S=7.45

$^1$H NMR(CDCl$_3$):δ 7.25(d,2H,J=S,MePhH); 7.07(d,2H, J=8, MePhH); 6.96(q,1H, (MeO)2Ar-4-H); 6.88(d,1H, (MeO)2Ar- 2-H); 6.78(d,2H,J=8, (MeO)2Ar-6-H); 3.88, 3.84(2s,2H, 2ArOCH$_3$); 3.35(t,2H,6-CH$_2$Br); 2.32(s,3H,ArCH$_3$); 2.2(m,2H,3-CH$_2$); 1.84(m,2H,6-CH$_2$); 1.48,1.31(2m, 4H, 5-CH$_2$).

EXAMPLE 107

α-(3,4-Dimethoxyphenyl)-1,3-dihydro-5-hydroxy-6-methoxy-α-[(4-methylphenyl)thio]-2H-isoindole-2-heptanenitrile The procedure of Example 49 is used with 0.209 g of 2,3-dihydro-6-methoxy-1H-isoindol-5-ol (Example 105) and 0.57 g of α-(5-bromopentyl)-3,4-dimethoxy-α-[(4-methylphenyl)thio]benzeneacetonitrile. This affords 0.5 g of the desired product as a gray foam.

MS(Hi res): m/z

Calcd for $C_{31}H_{36}N_2SO_4$ 533.2474 Found 533.2460

EXAMPLE 108

5-(2-Chloroethoxy)-α-(3,4-dimethoxyphenyl)-1,3-dihydro-6-methoxy-α-[[4-methylphenyl)thio]-2H-isoindole-2-heptanenitrile The procedure of Example of 32 is used with 0.45 g of α-(3,4-dimethoxyphenyl)-1,3-dihydro-5-hydroxy- 6-methoxy-α-[(4-methylphenyl)thio]-2H-isoindole- 2-heptanenitrile and 0.65 g of 2-chloroethyl p-toluenesulfonate. This affords 0.367 g of the desired product as a light brown oil.

MS(Hi res): m/z

Calcd for $C_{33}H_{39}N_2SClO_4$ 595.2397 Found 595.2391(M+H)

EXAMPLE 109

α-(3,4-Dimethoxyphenyl)-1,3-dihydro-5-[2-(1H-imidazol-1-yl)ethoxy]-6-methoxy-α-[(4-methylphenyl)thio]-2H-isoindole-2-heptanenitrile To a solution of 0.11 g of imidazole in 6 mL of N,N-dimethylformamide, under argon, is added 0.036 g of 60% of sodium hydride in oil. After stirring for 40 minutes, a solution of 0.3 g of 5-(2-chloroethoxy)-α-(3,4-dimethoxyphenyl)-1,3-dihydro-6-methoxy-α-[(4-methylphenyl)thio]-2H-isoindole-2-heptanenitrile in 8 mL of toluene is added followed by 0.3 g of sodium iodide. The resulting solution is heated at 75° C. for 21 hours. The solution is cooled and and poured into water. The solution is extracted with ethyl acetate land the organic layer washed with brine and dried over sodium sulfate. The solvent is removed at reduce pressure and the residual oil purified via column chromatography using a gradient elution from 4% methyl alcohol in methylene chloride to 9% methyl alcohol in methylene chloride. This affords 0,196 g of the desired product as a beige oil.

EXAMPLE 110

α-(3,4-Dimethoxyphenyl)-1,3-dihydro-5-[2-(1H-imidazol-1-yl)ethoxy]-6-methoxy-α-[(4-methylphenyl)thio]-2H-isoindole-2-heptanenitrile dihydrochloride To a solution of 0.196 g of α-(3,4-dimethoxyphenyl)-1,3-dihydro-5-[2-(1H-imidazol-1-yl)ethoxy]-6-methoxy-α-[(4-methylphenyl)thio]-2H-isoindole-2-heptanenitrile in 0.5 mL of methylene chloride is added 5 mL of diethyl ether and then 0.17 mL of 4.5N hydrochloric acid in ethyl alcohol. An additional 15 mL of diethyl ether is added and the solution stirred vigorously for 1 hour. The white solid is collected by filtration, washed with diethyl ether and dried. This affords 0.166 g of the desired product as a white solid.

Calcd for $C_{36}H_{42}N_4SO_4$ 2HCl$_{1.5}$M: C=59.58, H=6.34, N=7.71, Cl=9.76, S=4.41 Found C=59.49, H=6.48, N=7.52, Cl=9.62, S=4.28

EXAMPLE 111

[(7-Bromo-1-phenylheptyl)thio]benzene

A solution of 20.02 g of benzylphenylthioether in 300 ml of diethyl ether is cooled, under nitrogen, in a dry ice bath (the starting thioether precipitates out of solution). Sixty-two ml of 1.7M t-butyllithium, in pentane, is added and after 30 minutes most of the precipitate is re-dissolved. The reaction mixture is warmed to 0° C. for 10 minutes, but it appears that more precipitate is being formed, therefore the reaction is recooled to −78° C. for 30 minutes. The resulting yellow solution is transferred, under nitrogen via canula to a cooled, −78° C., second flask charged with 38.5 ml of 1,6-dibromohexane in 400 ml of diethyl ether (200 ml of tetrahydrofuran needed to maintain a homogenous solution). After the addition, the reaction mixture is allowed to warm to room temperature over 4 hours. Ten ml of ethyl acetate and 10 ml of 2-propanol is added and the reaction is concentrated in vacuo. The white oily residue is dissolved in chloroform, washed with dilute hydrobromic acid and saturated sodium chloride, dried and concentrated in vacuo to give 74.6 g of crude product. The crude product was purified 3× by chromatography (hexane to chloroform to methyl alcohol) to give 29.26 g of pure product.

MS(CI): m/z 362(M$^+$) and 365(M$^+$+H).

Calcd for $C_{19}H_{23}BrS$: C=63.31; H=6.37; Br=21.27; S=9.09 Found C=63.05; H=6.49; Br=21.05; S=9.14

EXAMPLE 112

1,2,3,4-Tetrahydro-6,7-dimethoxy-2-[7-phenyl-7-(phenylthio)heptyl]isoquinoline

The free base from 4.60 g of 6,7-dimethoxy- 1,2,3,4-tetrahydroisoquinoline hydrochloride, 3.63 g of [(7-bromo-1-phenylheptyl)thio]benzene, 50 ml of acetonitrile and 2.61 ml of ethyl diisopropylamine is heated at reflux temperature for 29 hours. The solvent is evaporated over night and the residue is partitioned between chloroform and aqueous ammonium hydroxide. The organic layer is dried and concentrated in vacuo to give 5.81 g of crude product. The residue is purified by chromatography (silica gel: chloroform/methyl alcohol) to give 1.73 g of the desired product.

Calcd for $C_{30}H_{37}NO_2S$: C=75.75: H=7.84; N=2.94; S=6.74 Found C=75.40; H=7.56; N=2.74; S=6.96

MS(CI): m/z 476(M–H$^+$).

EXAMPLE 113

α-(5-Bromopentyl)-α-(cyclohexylthio)-3,4-dimethoxy-benzeneacetonitrile

To a solution of 7.57 g of product from Example 82 in 180 ml of anhydrous tetrahydrofuran, under argon, is added 1.3 g of 50% sodium hydride in oil. The mixture is stirred at room temperature for 1 hour; followed by the addition of 10.6 ml of 1,5-dibromopentane and the stirring is continued for 4 hours at room temperature. The reaction mixture is poured into 450 ml of water and extracted with diethyl ether. The organic layer is washed with saturated sodium chloride, dried, filtered and concentrated in vacuo to give 23 g of a crude oil. The oil is purified by chromatography (silica gel: hexane to 10% ethyl acetate/hexane) to give 8.9 g of the desired product.

$^1$H-NMR(CDCl$_3$) :δ 7.19–7.15(m, 1H,Ar); 7.08(d, 1H,Ar); 6.89–6.83(d,1H,Ar); 3.91(S,6H,4-OCH$_3$); 3.33(t, 2H,-CH$_2$Br); 2.65(M,1H); 2.18–1.95(m, 3H); 1.83–1.78 (m, 3H); 1.56–1.35 (m, 7H); 1.34–1.12(m,5H).

EXAMPLE 114

α-(Cyclohexylthio)-α-(3,4-dimethoxyphenyl)-3,4-dihydro-7-hydroxy-6-methoxy-2(1H)-isoquinoline-heptanenitrile A mixture, under argon, of 2.17 g of product from Example 113, 1.8 g of product from Example 28, 13.0 ml of N,N-diisopropyl ethylamine and 80 ml of acetonitrile is heated under reflux temperature for 8 hours. The reaction is cooled and concentrated in vacuo and dried under high vacuum for 1 hour. The crude residue is dissolved in 70 ml of tetrahydrofuran and 10.0 ml of 1M tetrabutyl ammonium fluoride in tetrahydrofuran is added and the mixture is stirred at room temperature, under argon, for 2.5 hours. The mixture is poured into water and extracted with ethyl acetate. The organic layer is washed with saturated sodium chloride, dried, filtered, and concentrated in vacuo to give 4.0 g of a brown oil. The oil is purified by chromatography (silica gel: 1%, 1.5% and 2% methyl alcohol/methylene chloride)to give 2.1 g of the desired product.

Calcd for $C_{31}H_{42}N_2SO_4$: C=69.11; H=7.86; N=5.20 Found C=68.93; H=7.82; N=5.08

EXAMPLE 115

7-(2-Chloroethoxy)-α-(cyclohexylthio]-α-(3,4-dimethophenyl)-3,4-dihydro-6-methoxy-2(1H)-isoquinolineheptanonitrile A mixture, under argon, of 2.0 g of product from Example 114, 15 ml of 1N sodium hydroxide, 5.4 ml of 2-chloroethyl-p-toluene sulfonate and 70 ml of 2-butanone is heated at reflux temperature for 18 hours. The mixture is cooled, concentrated in vacuo and the residue partitioned between ethyl acetate and water. The organic layer is washed with saturated sodium chloride, dried, and concentrated in vacuo to give an oil. The oil is purified by chromatography (silica gel: methylene chloride, 0.5%, 1.0% and 1.5% methyl alcohol/methylene chloride) to give 1.7 g of the desired product.

Calcd for $C_{33}H_{45}N_2SClO_4$ 0.1M $CH_2Cl_2$: C=65.20; H=7.47; N=4.59; S=5.25; Cl=6.98 Found C=65.32; H=7.66; N=4.53; S=5.34; Cl 7.14

EXAMPLE 116

α-(Cyclohexylthio)-α-(3,4-dimethoxyphenyl)-3,4-dihydro-7-(2-imidazol-1-ylethoxy)-6-methoxy-2(1H)-isoquinolineheptanonitrile dihydrochloride To a solution, under argon, of 0.59 g of imidazole in 16 ml of N,N-dimethylformamide is added 0.185 g of 50% sodium hydride in oil. The mixture is stirred at room temperature for 1hour; followed by the addition of 1.6 g of product from Example 115 in 20 ml of toluene containing 0.10 g of potassium iodide. The resulting reaction mixture is heated at 75° C. overnight. The solution is cooled, poured into water and extracted with ethyl acetate. The organic layer is washed with saturated sodium chloride, dried, and concentrated in vacuo to give an oil. The oil is purified by chromatography (silica gel: 2, 4, 6, 8 and 10% methyl alcohol/methylene chloride) to give 1.27 g of a beige foam. The foam is dissolved in 3.0 ml of ethyl alcohol and 1.2 ml of 4.5M hydrogen chloride in ethyl alcohol is added. The mixture As stirred and diethyl ether is added. The reaction mixture is kept in the refrigerator overnight. The supernatant is decanted, the oil triturated with diethyl ether and left in the refrigerator for 48 hours. The solid is collected, washed with diethyl ether and dried for 3 hours at 40° C. under high vacuum to give 1.29 g of the desired product as a white solid.

Calcd for $C_{36}H_{48}N_4SO_4$ 1.75M HCl 1M $H_2O$ C=60.50; H=7.30; N=7.84; S=4.49; Cl=8.68 Found C=60.10; H=7.14; N=7.75; S=4.33; Cl=8.48

EXAMPLE 117

(3,4-Dimethoxyphenyl)(2-pyridylthio]acetonitrile

To a 5° C. solution of 3,4-dimethoxyphenyl acetonitrile in 40 ml of tetrahydrofuran is added, dropwise over a period of 20 minutes, 30.0 ml of sodium bis(trimethylsilyl)amide. The resultion mixture is stirred at 0°–5° C. for 50 minutes. A solution of 3.33 g of 2,2'-dipyridyl disulfide in 10 ml of tetrahydrofuran is added, dropwise at 0°–5° C. The reaction is stirred at 5° C. for 40 minutes and then at room temperature for 1.5 hours. The reaction is poured into ice water and extracted with ethyl acetate. The organic layer is washed with saturated sodium chloride, dried and concentrated in vacuo to give an oil which solidified on standing. The solid is dissolved in 16 ml of hot ethyl acetate to which 12 ml of hexane is added and the mixture is left at room temperature for 0.5 hour followed by cooling overnight in the refrigerator. The crystals are collected and dried to give 2.75 g of the desired product.

mp 108°–110° C.

Calcd for $C_{15}H_{14}N_2SO_2$: C=62.92; H=4.93; N=9.78; S=11.20 Found C=62.76; H=4.95; S=9.74; S=11.17

EXAMPLE 118

7-Bromo-2-(3,4-dimethoxyphenyl)-2-(2-pyridylthio]heptanonitrile

The title compound is prepared by the procedure of Example 113 using 1.3 g of product from Example 117, 0.218 g of 50% sodium hydride, 2.15 g of 1,5-dibromopentane and 16 ml of dimethyl sulfoxide to give after chromatography 1.61 g of the desired product as a yellow oil.

Calcd for $C_{20}H_{23}N_2SBrO_2$: C=55.18; H=5.32; N=6.43; S=7.36; Br=18.35 Found C=55.39; H=5.33; N=6.32; S=7.16; Br=18.17

EXAMPLE 119

α-(3,4-Dimethoxyphenyl)-3,4-dihydro-6,7-dimethoxy-α-(2-pyridylthio)-2(1H)-isoquinoline-heptanonitrile A mixture, under argon, of 1.5 g of product from Example 118, 0.790 g of 6,7-dimethoxy-1,2,3,4-tetrahydroisoquinoline hydrochloride, 7 ml of N,N-diisopropyl ethylamine and 60 ml of acetonitrile is heated at reflux temperature overnight. The reaction is cooled and concentrated in vacuo to give an oil. The oil is purified by chromatography (silica gel: 1 and 2% methyl alcohol/methylene chloride) to give 1.1 g of the desired product as a glassy yellow solid.

Calcd for $C_{31}H_{37}N_3SO_4$: C=67.98; H=6.81; N=7.67; S=5.85 Found C=67.68; H=6.77; N=7.46; S=5.76

EXAMPLE 120

α-(Cyclohexylthio)α-(3,4-dimethoxyphenyl]-1,3-dihydro-5,6-dimethoxy-2(1H)-isoindoleheptanenitrile hydrochloride To 2.04 g of product from Example 86 in ethyl alcohol is added 1.2 ml of 4.5M ethanolic hydrochloride followed by diethyl ether until the solution becomes turbid. The mixture is cooled in the refrigerator over the week-end. The solid is collected and the filtrate is concentrated in vacuo, dissolved in ethyl alcohol, decolorized, filtered and concentrated to a low volume. Diethyl ether is added until turbid, argon gas is bubbled through the solution at room temperature. The flask is protected from light with aluminum foil and left at room temperature for 2 hours followed by cooling in the refrigerator overnight. The solid is collected to give 1.51 g of the desired product.

Calcd for $C_{31}H_{42}N_2SO_4$ HCl: C=64.73; H=7.53; N=4.87; S=5.57; Cl=6.16 Found C=64.39; H=7.75; N=4.74; S=5.43; Cl=6.00

EXAMPLE 121

α-[5-[[1,1-Dimethylethyl)dimethylsilyl]oxy]pentyl]-3,4-dimethoxybenzeneacetic acid methyl ester To a solution, −78° C. under argon, of 2.38 g of 3,4-dimethoxyphenyl acetic acid methyl ester in 30 ml of tetrahydrofuran is added 12.45 ml of 1.0M sodium hexamethylsidilazide. The solution is stirred at −78° C. for 5 minutes and then warmed to 0° C. for 1 hour. To this solution is added 3.5 g of (5-bromopentyl)(1,1-dimethylethyl)dimethyl silane. The reaction mixture is allowed to warm to room temperature and stirred for 12 hours. The mixture is diluted with diethyl ether and water, the layers are separated and the organic layer is washed with saturated sodium chloride, dried and concentrated in vacuo. The residue is purified by chromatography (silica gel: hexane/ethyl acetate, 5/1) to give 2.6 g of the desired product as a clear oil.

MS(Hi res): calcd 410.2488 found 410.2492

EXAMPLE 122

α-[5-[[(1,1-Dimethylethyl)dimethylsilyl]oxy]pentyl]-3,4-dimethoxyα-[(4-methylphenyl)thio]benzeneacetic acid methyl ester The title compound is prepared by the procedure of Example 121 using 1.5 g of product from Example 121 in 35 ml of tetrahydrofuran, 4.0 ml of 1.0M sodium hexamethyldisilazide, and 1.0 g of p-tolyldisulfide to give 0.9 g of the desired product.

EXAMPLE 123

α-(5-Hydroxypentyl)-3,4-dimethoxy-α-[(methylphenyl)thio]benzeneacetic acid methyl ester To a 0° C. solution of 0.9 g of product from Example 122 in 15 ml of tetrahydrofuran is added 1.86 ml of 1.0M tetrabutylammonium fluoride. The reaction is allowed to warm to room temperature for 1 hour followed by the addition of 5 ml of 0.1N sodium hydroxide. The reaction mixture is extracted with diethyl ether. The organic layer is dried and concentrated in vacuo. The residue is purified by chromatography (silica gel: ethyl acetate/hexane, 3/12) to give 0.67 g of the desired product.

EXAMPLE 124

α-[3,4-Dimethoxyphenyl)-1,3-dihydro-5,6-dimethoxy-α-[(4-methylphenyl)thio]-2H-isoindole-2-heptanoic acid methyl ester To a solution of 0.2 g of product from Example 123 in 5 ml of methylene chloride is added 0.092 g of p-toulenesulfonyl chloride. The solution is cooled to 0° C. and 0.15 ml of pyridine is added. The mixture is allowed to warm to room temperature and stirred for 5 hours. The solvent is removed with a stream of argon; and to the solvent is added 5 ml of acetonitrile, 0.5 ml of diisopropylethylamine and 0.087 g of 2,3-dihydro-5,6-dimethoxy-1H-isoindole. The solution is heated at reflux temperature under argon for 2 hours and then cooled to room temperature. The reaction mixture is concentrated in vacuo and the residue partitioned between ethyl acetate and water. The organic layer is washed with saturated sodium chloride, dried and concentrated in vacuo. The residue is purified by chromatography (silica gel: methylene chloride/methyl alcohol, 95/5) to give 0.12 g of the desired product.

MS(Hi res): Calcd 579.2654 Found 580.2736 (M+H).

We claim:

1. A compound of the formula:

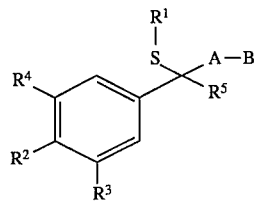

wherein $R^2$ is H, OH, O-alkyl($C_1$-$C_4$), F, Br, Cl, I, $NO_2$, $OCF_3$, alkyl($C_1$-$C_6$), or $N(R^{12})_2$;

$R^3$ is H, OH, O-alkyl($C_1$-$C_3$), straight or branched OSi—($C_1$-$C_4$)alkyl, F, Br, Cl, I, $NO_2$, alkyl($C_1$-$C_6$), $OCH_2CH_2Cl$, O-alkyl($C_2$-$C_5$)-heterocycle, O-alkyl($C_2$-$C_5$)$N(R^{12})_2$, $OSO_2CF_3$, $OCF_3$, or $N(R^{12})_2$;

or $R^2$ and $R^3$ taken together are methylenedioxy or ethylenedioxy;

$R^4$ is H, OH, O-alkyl($C_1$-$C_4$), F, Br, Cl, I, or alkyl($C_1$-$C_3$);

$R^5$ is H, CN, $CH_2OH$, $CO_2$($C_1$-$C_3$)alkyl, $CH_2NH_2$, $CH_2N(R^{12})_2$ or alkyl($C_1$-$C_3$);

$R^1$ is straight or branched ($C_1$-$C_{12}$) alkyl, cycloalkyl ($C_3$-$C_7$), bicycloalkyl($C_6$-$C_{10}$), tricycloalkyl($C_6$-$C_{10}$), a heterocycle or a moiety of the formula:

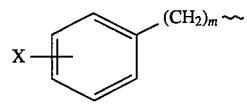

wherein m is an integer 0–3,

X is H, straight or branched ($C_1$-$C_4$)alkyl, I, Cl, Br, F, $NO_2$, or $N(R^{12})_2$;

A is straight or branched ($C_2$-$C_{12}$)alkyl, or a moiety selected from these of the formulae:

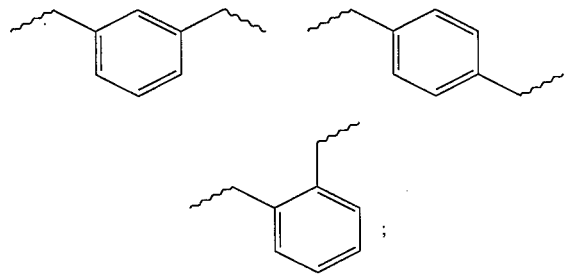

B is a moiety of the formula:

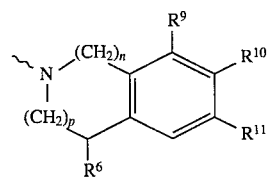

n and p are integers with n=1 and p=0;

$R^6$ is H, alkyl($C_1$-$C_4$), or a moiety of the formula:

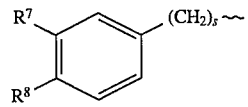

s is an integer with s=1–3, $R^7$ and $R^8$ are independently H, alkyl($C_1$-$C_4$), or O-alkyl($C_1$-$C_4$);

$R^9$ is H, O-alkyl($C_1$-$C_4$), F, Br, Cl, I, or alkyl($C_1$-$C_3$);

$R^{10}$ is H, O-alkyl($C_1$-$C_3$), OH, F, Br, Cl, I, alkyl($C_1$-$C_3$), $OCH_2CH_2Cl$, O-alkyl($C_2$-$C_5$)-heterocycle, S-alkyl($C_1$-$C_4$), $OSO_2CF_3$, $OCF_3$, $OCH_2$-phenyl, $NO_2$ or $N(R^{12})_2$;

$R^{11}$ is H, O-alkyl($C_1$-$C_4$), S-alkyl($C_1$-$C_4$), OH, F, Br, Cl, I, $OCF_3$, $OCH_2$phenyl, alkyl($C_1$-$C_3$) or O-aklyl ($C_2$-$C_5$)-heterocycle;

$R^{12}$ is alkyl($C_1$-$C_4$);

heterocycle is imidazole, pyrrole, 1,2,4-triazole, oxazole, isoxazole, furan, thiophene, pyridine, pyrimidine, or thiazole;

or a pharmaceutically acceptable salt thereof.

2. A compound according to claim 1, wherein $R^2$ is H, O-alkyl($C_1$-$C_4$), F, Br, Cl, I, $OCF_3$, or alkyl($C_1$-$C_6$);

$R^3$ is H, O-alkyl($C_1$-$C_3$), straight or branched OSi—($C_1$-$C_4$)alkyl, F, Br, Cl, I, $NO_2$, alkyl($C_1$-$C_6$), $OCH_2CH_2Cl$, O-alkyl($C_2$-$C_5$)-heterocycle, $OSO_2CF_3$, or $OCF_3$;

or $R^2$ and $R^3$ taken together are methylenedioxy or ethylenedioxy;

$R^4$ is H, O-alkyl($C_1$-$C_4$), F, Br, Cl, I, or alkyl($C_1$-$C_6$);

$R^5$ is H, CN, $CH_2OH$, $CO_2$($C_1$-$C_3$)alkyl, or alkyl($C_1$-$C_3$);

$R^1$ is straight or branched ($C_1$-$C_{12}$) alkyl, cycloalkyl($C_3$-$C_7$), bicycloalkyl($C_6$-$C_{10}$), tricycloalkyl($C_6$-$C_{10}$), a heterocycle or a moiety of the formula:

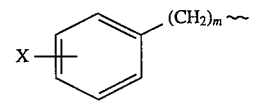

wherein m is an integer from 0–3,

X is H, straight or branched($C_1$-$C_4$)alkyl, I, Cl, Br, F, $NO_2$, or $N(R^{12})_2$;

A is straight or branched($C_2$-$C_{12}$)alkyl, or a moiety selected from those of the formulae:

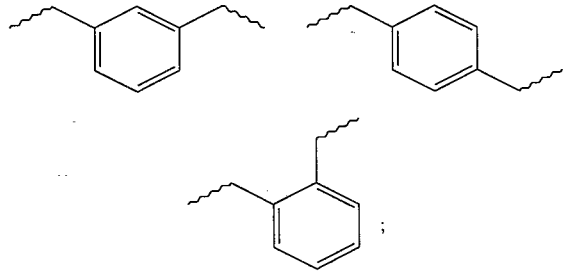

71

B is a moiety of the formula:

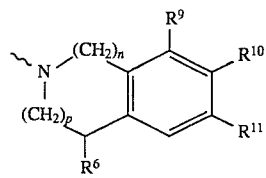

n and p are integers with n=1 and p=0;
R⁶ is H, alkyl(C₁–C₄), or a moiety of the formula:

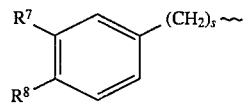

s is an integer with s=1–3;
$R^7$ and $R^8$ are independently H, alkyl(C₁–C₄), or O-alkyl(C₁–C₄);
$R^9$ is H, O-alkyl(C₁–C₄), F, Br, Cl, I, or alkyl(C₁–C₃);
$R^{10}$ is H, O-alkyl(C₁–C₃), OH, F, Br, Cl, I, alkyl(C₁–C₃), OCH₂CH₂Cl, O-alkyl(C₂–C₅)-heterocycle, OCH₂-phenyl or OSO₂CF₃;
$R^{11}$ is H, O-alkyl(C₁–C₄), OH, O-alkyl(C₂–C₅)-heterocycle, F, Br, Cl, I or alkyl(C₁–C₃);
$R^{12}$ is alkyl(C₁–C₄); heterocycle is imidazole, pyrrole, 1,2,4-triazole, oxazole, isoxazole, furan, thiophene, pyridine, pyrimidine, or thiazole; or a pharmaceutically acceptable salts thereof.

3. A compound according to claim 1, wherein
$R^2$ is H, O-alkyl(C₁–C₄) or alkyl(C₁–C₆);
$R^3$ is H, O-alkyl(C₁–C₃), OSi(t-C₄H₉)(CH₃)₂, alkyl(C₁–C₆), OCH₂CH₂Cl, OCH₂CH₂—N-imidazole or OSO₂CF₃;
or $R^2$ and $R^3$ taken together are methylenedioxy or ethylenedioxy;
$R^4$ is H, O-alkyl(C₁–C₄), or alkyl(C₁–C₆);
$R^5$ is H, CN, CH₂OH, CO₂(C₁–C₃)alkyl, or alkyl(C₁–C₃);
$R^1$ is straight or branched (C₁–C₁₂) alkyl, cycloalkyl (C₃–C₇), bicycloalkyl (C₆–C₁₀), tricycloalkyl(C₆–C₁₀), a heterocycle or a moiety of the formula:

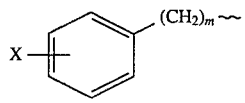

wherein
m is an integer from 0–3,
X is H, straight or branched (C₁–C₄) alkyl;
A is straight or branched (C₂–C₁₂)alkyl, or a moiety selected from those of the formulae:

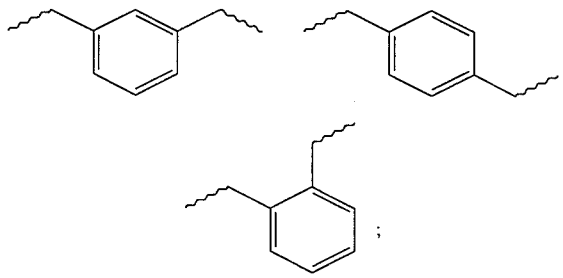

;

72

B is a moiety of the formula:

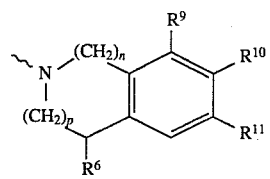

n and p are integers with n=1 and p=0;
R⁶ is H, alkyl(C₁–C₄) or a moiety of the formula:

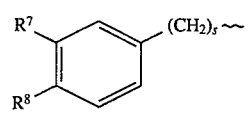

s is an integer with s=1–3;
$R^7$ and $R^8$ are independently H or O-alkyl(C₁–C₄)
$R^9$ is H or O-alkyl(C₁–C₄);
$R^{10}$ is H, O-alkyl(C₁–C₃), OH, F, Br, Cl, I, alkyl(C₁–C₃), OCH₂CH₂Cl, OCH₂CH₂—N-imidazole, OCH₂-phenyl or OSO₂CF₃;
$R^{11}$ is H, O-alkyl(C₁–C₄), OH, F, Br, Cl, I or alkyl(C₁–C₃);
$R^{12}$ is alkyl(C₁–C₄), heterocycle is imidazole, pyrrole, 1,2,4-triazole, oxazole, isoxazole, furan, thiophene, pyridine, pyrimidine, or thiazole; or a pharmaceutically acceptable salts thereof.

4. A compound according to claim 1, wherein
$R^2$ is H or O—CH₃;
$R^3$ is H, O—CH₃, OSi(t-C₄H₉)(CH₃)₂, OCH₂CH₂Cl, OCH₂CH₂—N-imidazole or OSO₂CF₃;
or $R^2$ and $R^3$ taken together are methylenedioxy or ethylenedioxy
$R^4$ is H or O—CH₃;
$R^5$ is H, CN, CH₂OH, CO₂CH₃, or alkyl(C₁–C₃);
$R^1$ is straight or branched (C₄–C₅) alkyl, cycloalkyl(C₅–C₆), adamantyl, 2-pyridiyl or a moiety of the formula:

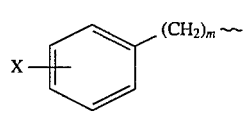

wherein
m is an integer 0–1;
X is H, straight or branched (C₁–C₄)alkyl;
A is straight or branched (C₂–C₁₂)alkyl, or a moiety of the formula:

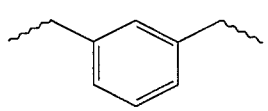

B is a moiety of the formula:

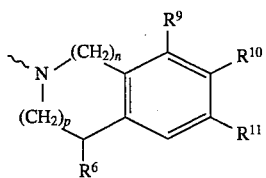

n and p are integers with n=1 and p=0;
$R^6$ is H, $CH_3$ or a moiety of the formula:

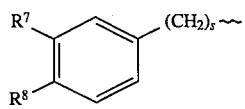

S=1;
$R^7$ and $R^8$ are independently H or O—$CH_3$;
$R^9$ is H or O-alkyl($C_1$–$C_4$);
$R^{10}$ is H, O—$CH_3$, OH, Cl, $OCH_2$ $CH_2Cl$, $OCH_2CH_2$—N-imidazole, $OCH_2$-phenyl or $OSO_2CF_3$;
$R^{11}$ is H, O—$CH_3$, OH, Cl;
$R^{12}$ is alkyl($C_1$–$C_4$); or a pharmaceutically acceptable salts thereof.

5. A compound according to claim 1, α-(3,4-dimethoxyphenyl)-1,3-dihydro-5,6-dimethoxy-α-[(4-methylphenyl)thio]-2H-isoindole-2-heptanenitrile.

6. A compound according to claim 1, α-(3,4-dimethoxyphenyl)-1,3-dihydro-5,6-dimethoxy-α-[(4-methylphenyl)thio]-2H-isoindole-2-heptanenitrile hydrochloride.

7. A compound according to claim 1, 2-[7-(3,4-dimethoxyphenyl)-7-[(4-methylphenyl)thio]heptyl]-2,3-dihydro-5,6-dimethoxy-1H-isoindole.

8. A compound according to claim 1, 5,6 dichloro-α-(3,4-dimethoxyphenyl)-1,3-dihydro-α-[4-methylphenyl)thio]-2-H-isoindole-2-heptanenitrile.

9. A compound according to claim 1, α-(cyclohexylthio)-α-(3,4-dimethoxyphenyl)-1,3-dihydro- 6,7-dimethoxy-2H-isoindole-2-heptanenitrile.

10. A compound according to claim 1, α-(3,4-dimethoxyphenyl)-1,3-dihydro-5-[2-(1H-imidazol- 1-yl)ethoxy]-6-methoxy-α-[(4-methylphenyl)thio]-2H-isoindole- 2-heptanenitrile dihydrochloride.

11. A compound according to claim 1, name of α-(3,4-dimethoxyphenyl)-1,3-dihydro-5,6-dimethoxy-α-[(4-methylphenyl)thio]-2H-isoindole-2-heptanoic acid methyl ester.

12. A compound according to claim 1, α-(cyclohexylthio)-α-(3,4-dimethoxyphenyl)-1,3-dihydro- 5,6-dimethoxy-2(1H)-isoindoleheptanenitrile hydrochloride.

13. A method of increasing the sensitivity of a tumor to an antineoplastic agent, which tumor is harbored in a subject and which tumor is resistant to said antineoplastic agent, comprising concurrently administering to said subject an antineoplastic agent and a potentiating agent, wherein said potentiating agent is a compound according to claim 1; said potentiating agent being administered in an amount effective to increase the sensitivity of said tumor to said anti-neoplastic agent.

* * * * *